(12) United States Patent
Akama et al.

(10) Patent No.: US 10,866,234 B2
(45) Date of Patent: Dec. 15, 2020

(54) METHOD FOR DETECTING ANALYTE

(71) Applicant: SYSMEX CORPORATION, Kobe (JP)

(72) Inventors: Kenji Akama, Kobe (JP); Seigo Suzuki, Ashiya (JP); Kenta Oda, Amagasaki (JP); Kentaro Shirai, Kobe (JP); Hana Kumamoto, Vernon Hills, IL (US)

(73) Assignee: SYSMEX CORPORATION, Kobe (JP)

( * ) Notice: Subject to any disclaimer, the term of this patent is extended or adjusted under 35 U.S.C. 154(b) by 468 days.

(21) Appl. No.: 15/695,426

(22) Filed: Sep. 5, 2017

(65) Prior Publication Data

US 2017/0370920 A1    Dec. 28, 2017

Related U.S. Application Data

(63) Continuation of application No. PCT/JP2016/055513, filed on Feb. 24, 2016.

(30) Foreign Application Priority Data

| Mar. 13, 2015 | (JP) | 2015-050205 |
| Aug. 28, 2015 | (JP) | 2015-169206 |
| Jan. 28, 2016 | (JP) | 2016-014744 |

(51) Int. Cl.
| *G01N 33/543* | (2006.01) |
| *G01N 15/14* | (2006.01) |
| *G01N 21/78* | (2006.01) |
| *G01N 21/64* | (2006.01) |
| *G01N 33/533* | (2006.01) |

(52) U.S. Cl.
CPC ....... *G01N 33/54306* (2013.01); *G01N 15/14* (2013.01); *G01N 21/6428* (2013.01); *G01N 21/78* (2013.01); *G01N 33/533* (2013.01); *G01N 33/543* (2013.01); *G01N 33/54313* (2013.01); *G01N 2021/6439* (2013.01)

(58) Field of Classification Search
None
See application file for complete search history.

(56) References Cited

U.S. PATENT DOCUMENTS

| 5,723,346 | A | * | 3/1998 | Frengen | G01N 33/54313 436/523 |
| 5,731,158 | A | | 3/1998 | Bobrow et al. | |
| 8,048,627 | B2 | | 11/2011 | Dressman et al. | |
| 8,236,574 | B2 | * | 8/2012 | Duffy | G01N 33/54306 436/518 |
| 9,377,388 | B2 | * | 6/2016 | Walt | B01J 19/0046 |
| 10,533,998 | B2 | * | 1/2020 | Link | B01F 5/0653 |
| 2005/0221339 | A1 | * | 10/2005 | Griffiths | B01F 5/0655 435/6.11 |
| 2006/0021666 | A1 | * | 2/2006 | Funatsu | B01L 3/50273 137/828 |
| 2008/0064113 | A1 | * | 3/2008 | Goix | G01N 35/1095 436/86 |
| 2008/0318249 | A1 | | 12/2008 | Powell et al. | |
| 2010/0075862 | A1 | * | 3/2010 | Duffy | G01N 33/54366 506/9 |
| 2010/0143908 | A1 | * | 6/2010 | Gillevet | C12Q 1/62 435/6 |
| 2010/0167945 | A1 | | 7/2010 | Singh et al. | |
| 2013/0053252 | A1 | * | 2/2013 | Xie | C40B 20/00 506/2 |
| 2013/0109019 | A1 | | 5/2013 | Murillo et al. | |
| 2013/0309675 | A1 | * | 11/2013 | Saito | 1/68 |
| 2013/0345088 | A1 | * | 12/2013 | Noji | G01N 21/6452 506/9 |
| 2014/0295430 | A1 | * | 10/2014 | Saito | C12Q 1/6804 435/6.11 |

FOREIGN PATENT DOCUMENTS

| JP | 2008-516251 A | 5/2008 |
| JP | 2013-531801 A | 8/2013 |
| JP | 2013-174616 A | 9/2013 |
| WO | WO 2006040551 | * 10/2005 |
| WO | 2013/051651 A1 | 4/2013 |
| WO | 2014/180853 A1 | 11/2014 |

OTHER PUBLICATIONS

Sepp et al. "Microbead display by in vitro compartmentalization: selection for binding using flow cytometry", FEBS Letters, vol. 532, No. 3, 2002, pp. 455-458.*

Rissin et al. "Single-molecule enzyme-linked immunosorbent assay detects serum proteins at subfebtomolar concentrations", Nature Biotechnology, vol. 28, No. 6, May 23, 2010, pp. 595-599.*

"Single-Molecule enzyme-linked immunosorbent assay detects serum proteins at subfemtomolar concentrations", Risin et al. Nat. Biotechnol. Jun. 2010; 28(6): 595-599.*

Armin Sepp et al: "Microbead display by in vitro compartmentalisation: selection for binding using flow cytometry", FEBS Letters, vol. 532, No. 3, 2002, pp. 455-458; Listed in the Japanese Office Action dated Feb. 18, 2020 in a counterpart Japanese patent application.

(Continued)

*Primary Examiner* — Ann Y Lam

(74) *Attorney, Agent, or Firm* — Sughrue Mion, PLLC

(57) ABSTRACT

The present invention relates to a method for detecting an analyte in a sample, comprising the steps of: forming on each of carrier particles a complex containing a first capture substance capable of binding to an analyte, one molecule of the analyte, a second capture substance capable of binding to the analyte, and a catalyst; immobilizing a reaction product on each of the carrier particles by reacting the catalyst in the complex with a substrate; and detecting the analyte by detecting the carrier particles on each of which the reaction product is immobilized.

20 Claims, 21 Drawing Sheets

(56) References Cited

OTHER PUBLICATIONS

David M Rissin et al: "Single-molecule enzyme-linked immunosorbent assay detects serum proteins at subfemtomolar concentrations", Nature Biotechnology, vol. 28, No. 6, May 23, 2010, pp. 595-599; Listed in the Japanese Office Action dated Feb. 18, 2020 in a counterpart Japanese patent application.
The Chinese Office Action dated Feb. 3, 2020 in a counterpart Chinese patent application No. 201680015139.0.
The Japanese Office Action dated Feb. 18, 2020 in a counterpart Japanese patent application No. 2017-506170.
Kotaro Konno et al., "Enzymatic activation of oleuropein: A protein crosslinker used as a chemical defense in the privet tree", Proc. Natl. Acad. Sci. USA, Aug. 1999, pp. 9159-9164, vol. 96.
Adrian Palmer et al., "Evaluation of novel polymeric High Sensitivity Fluorescent reporters in multiparameter flow cytometry", Sirigen, May 2011, No. 287.
George P. Anderson et al., "Amplification of microsphere-based microarrays using catalyzed reporter deposition", Biosensors and Bioelectronics, 2008, pp. 324-328, 24.
Stefaan Derveaux, "Development of a sensitive diagnostic multiplex platform based on digitally encoded microcarriers", Ghent University Faculty of Pharmaceutical Sciences, 2008, pp. 1-276.

\* cited by examiner

[FIG. 1]
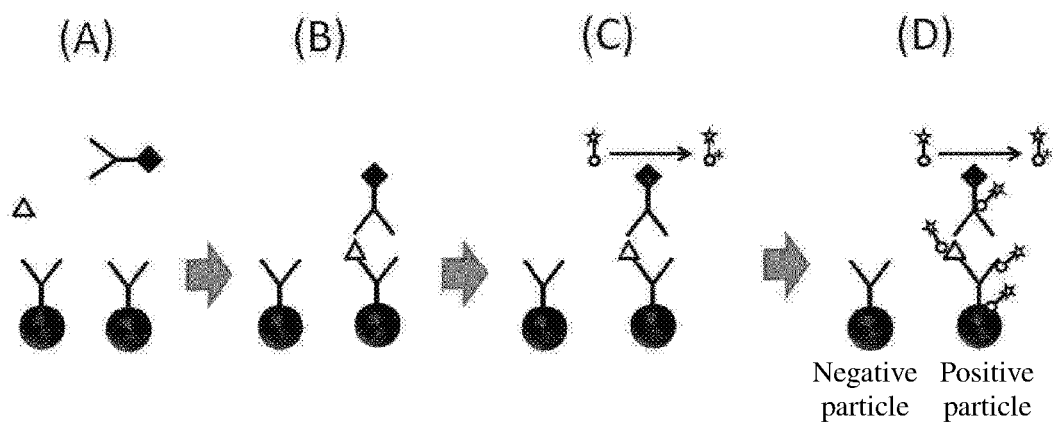
[FIG. 2]
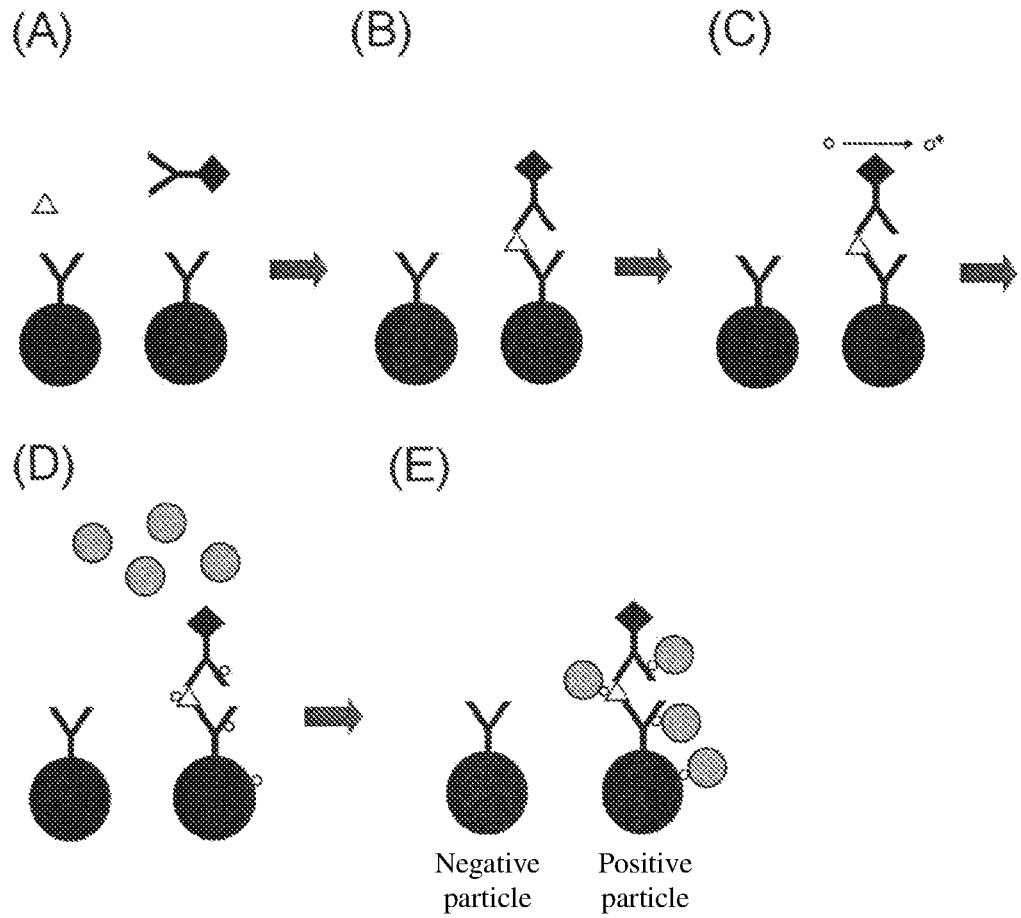

[FIG. 3]
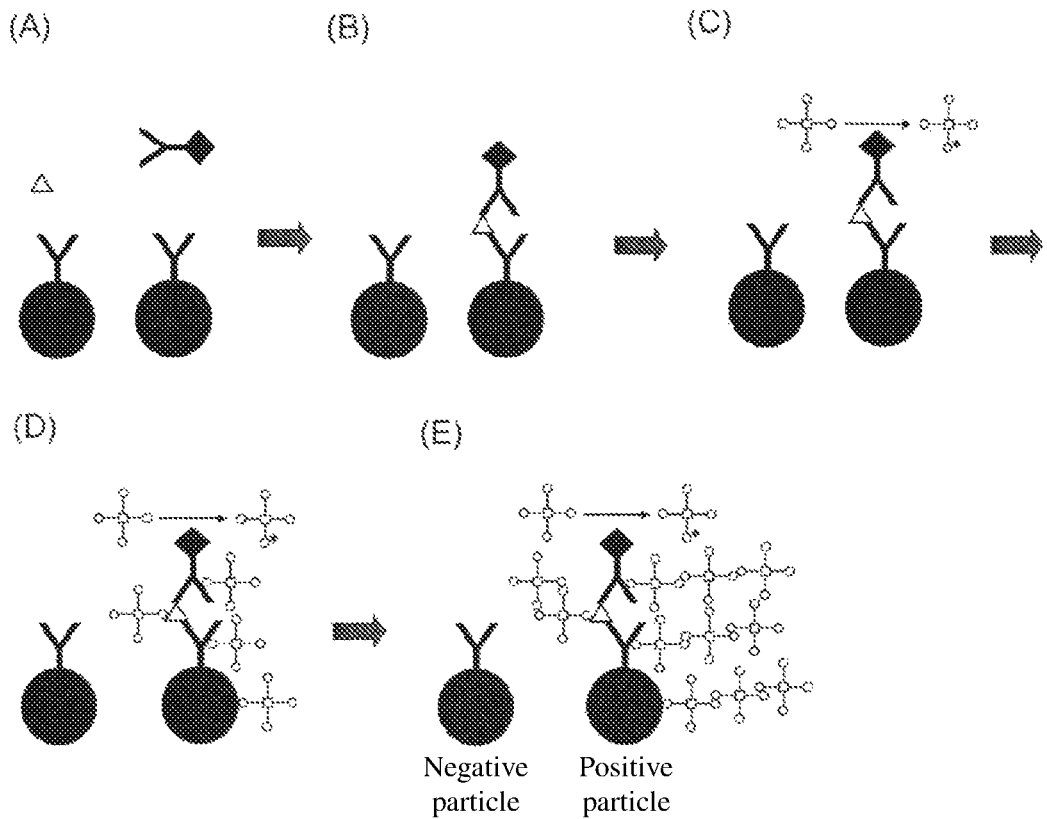
[FIG. 4]
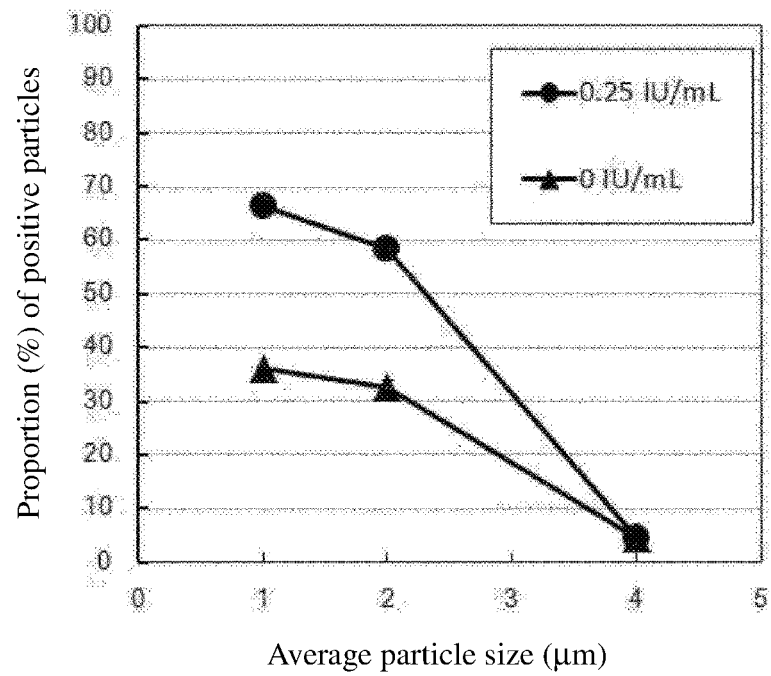

[FIG. 5]
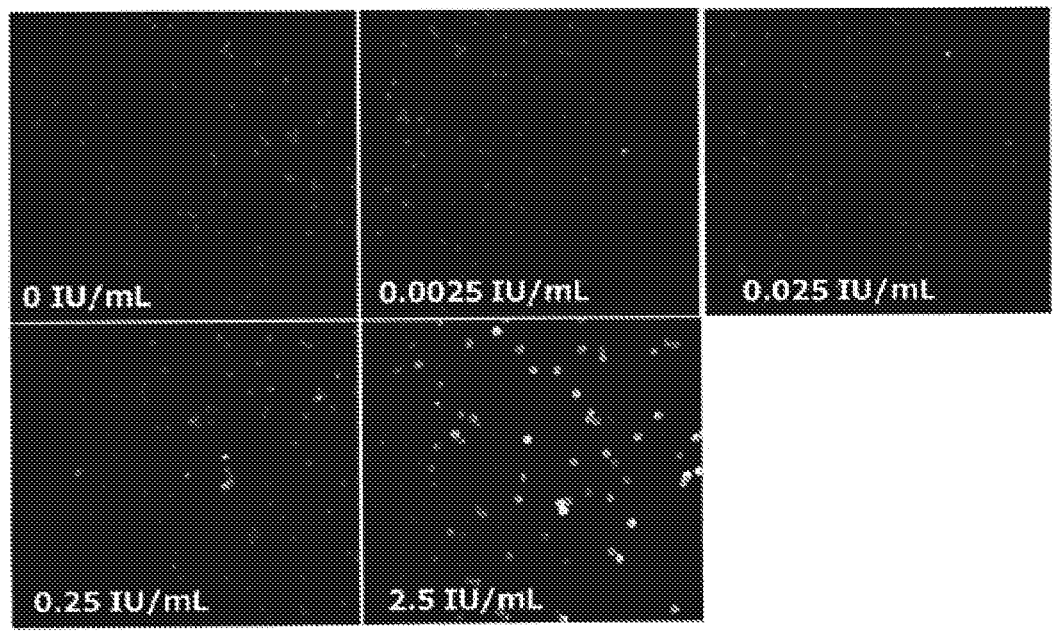
[FIG. 6]
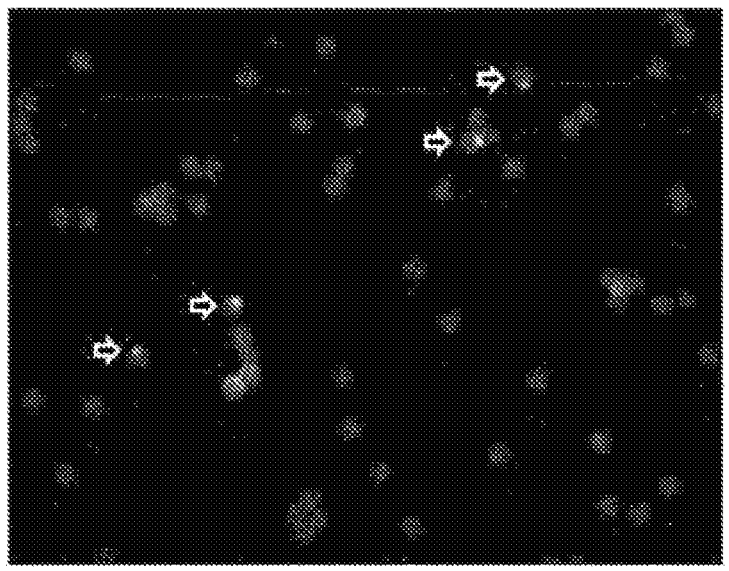

[FIG. 7]
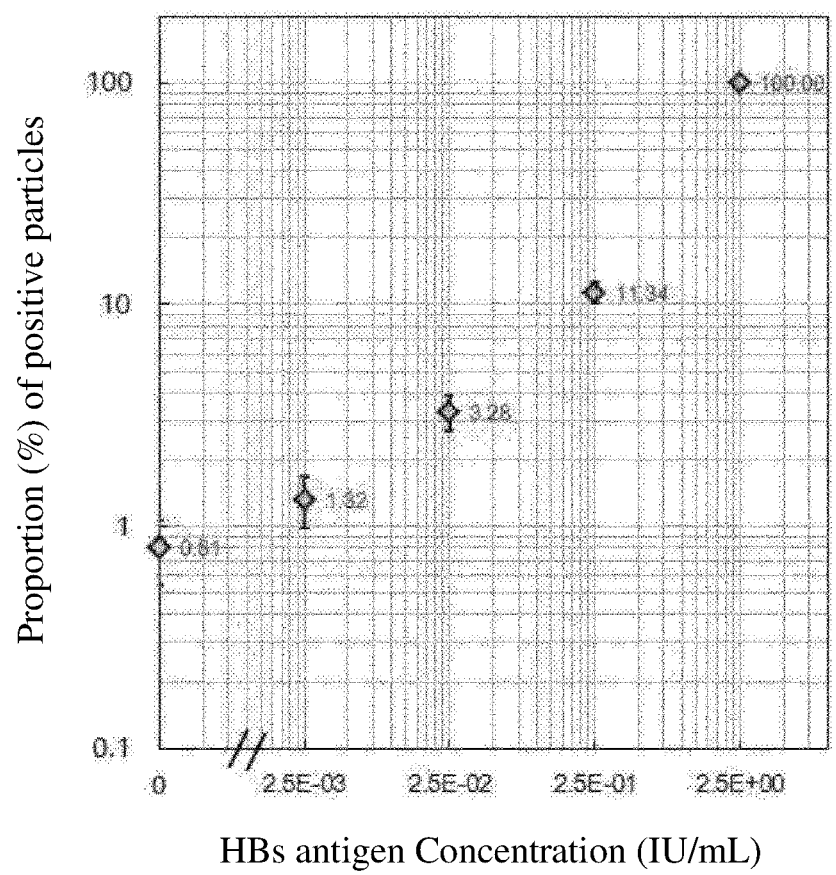
HBs antigen Concentration (IU/mL)

[FIG. 8]
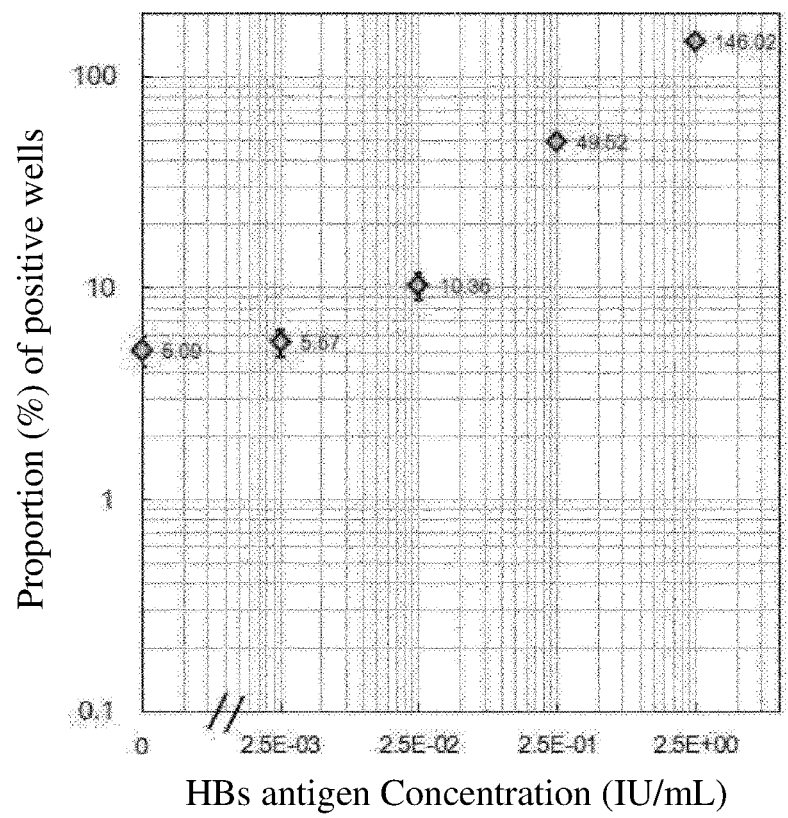
[FIG. 9A]
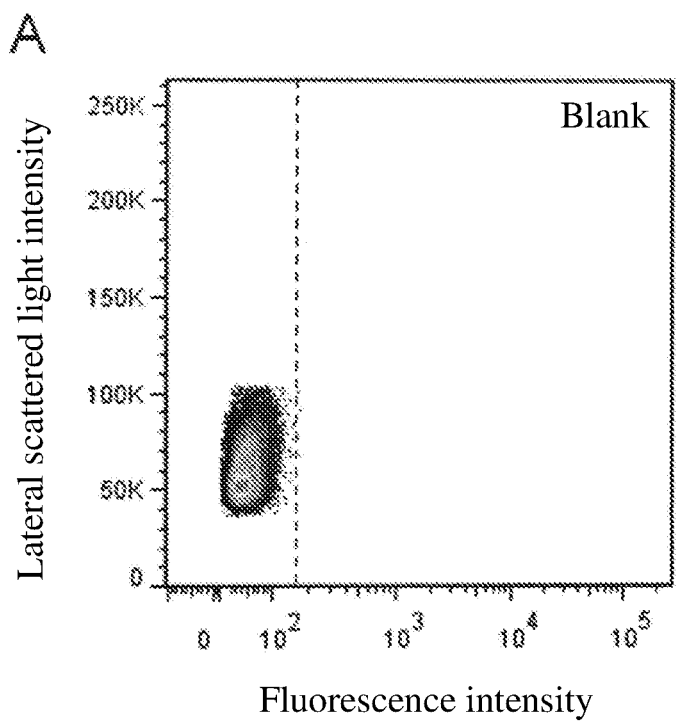

[FIG. 9B]
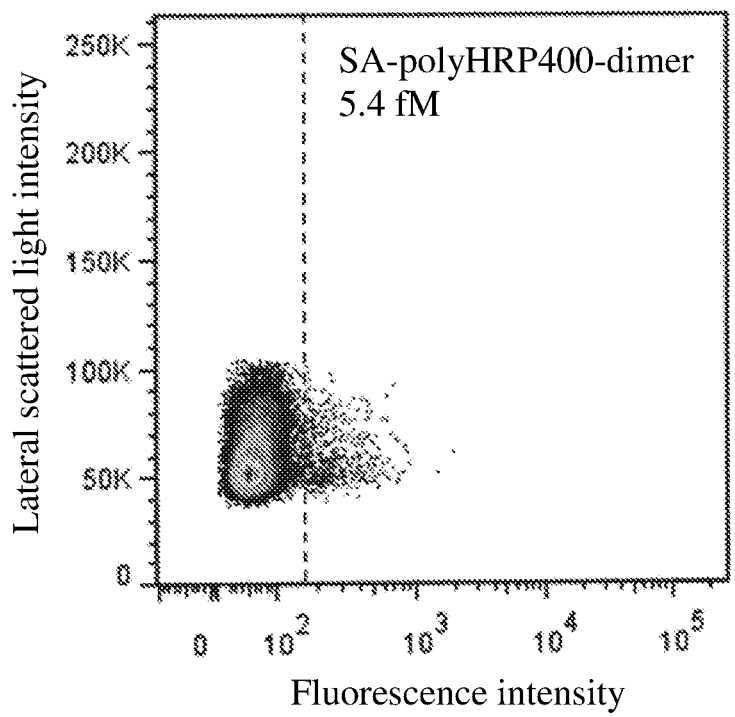
[FIG. 9C]
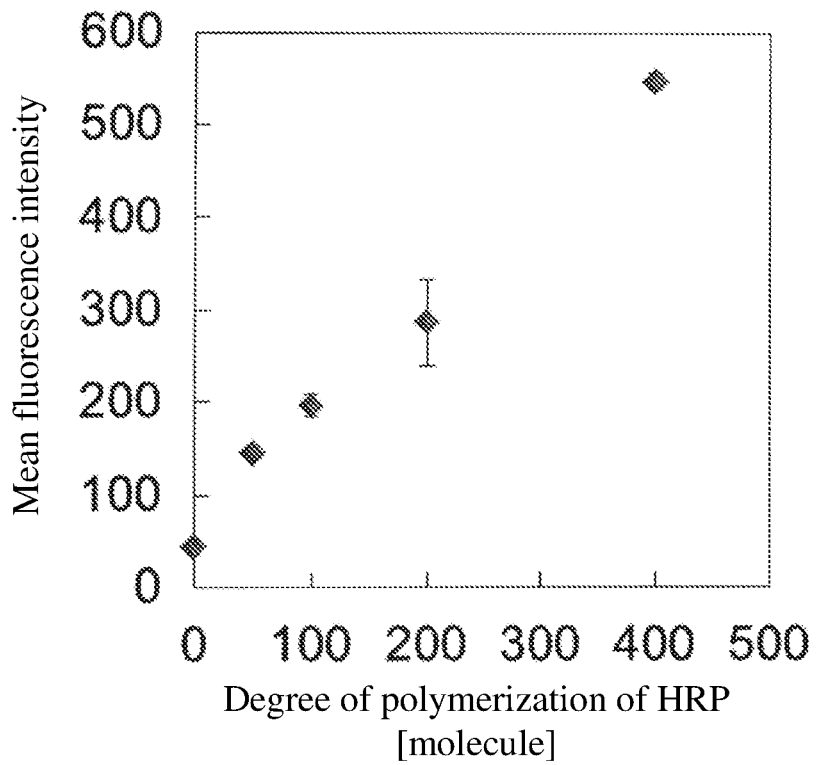

[FIG. 9D]
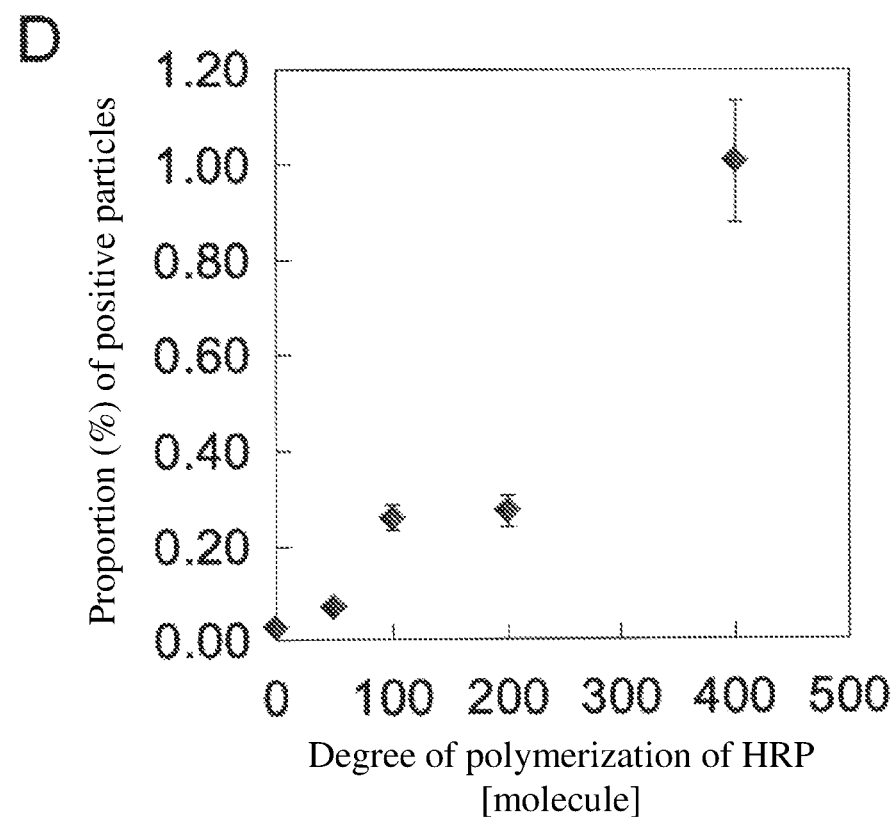

[FIG. 10]
0 IU/mL
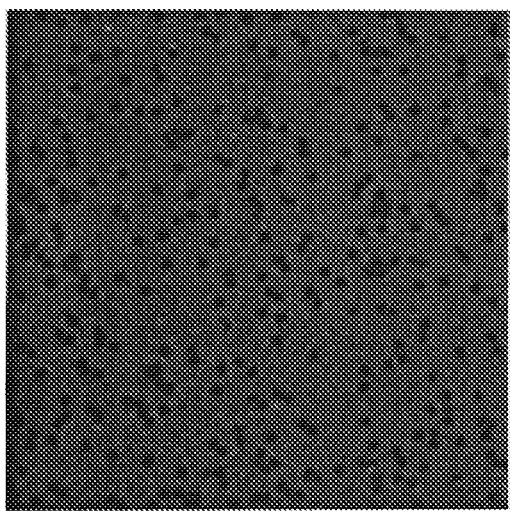
0.00025 IU/mL
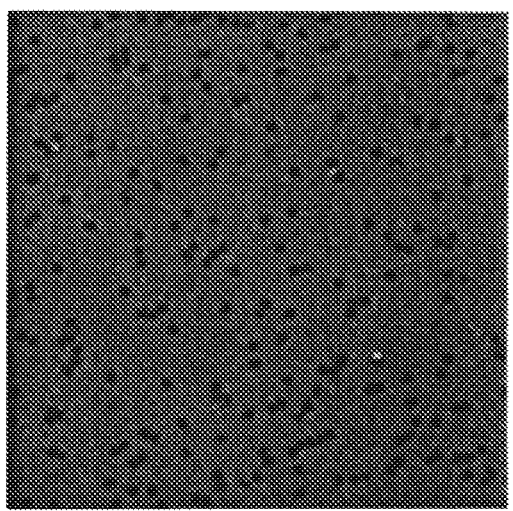
0.0025 IU/mL
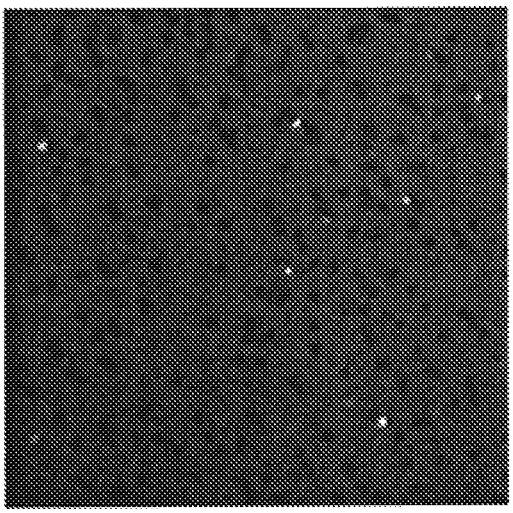
0.025 IU/mL
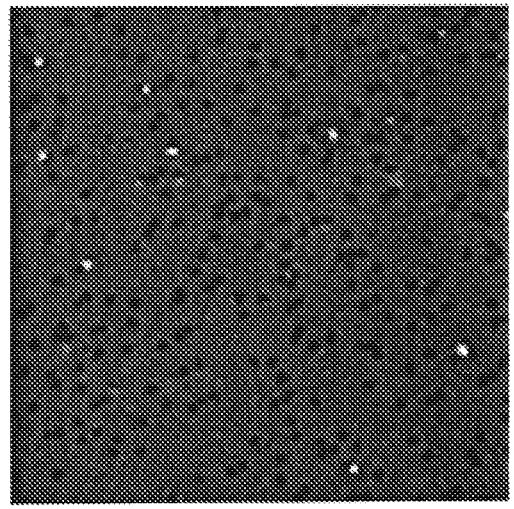

[FIG. 11]
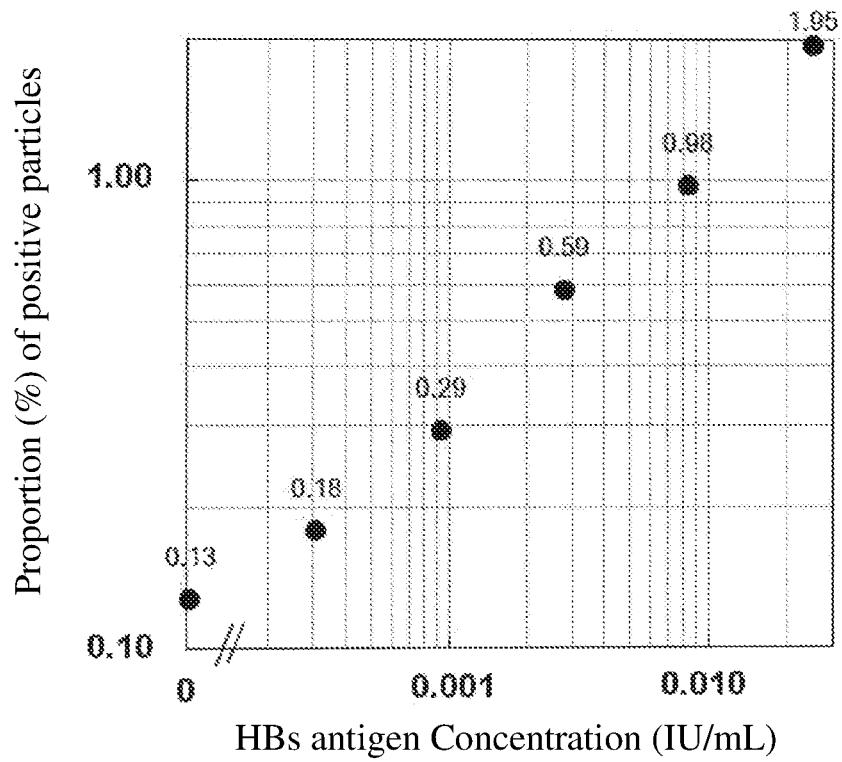
[FIG. 12A]
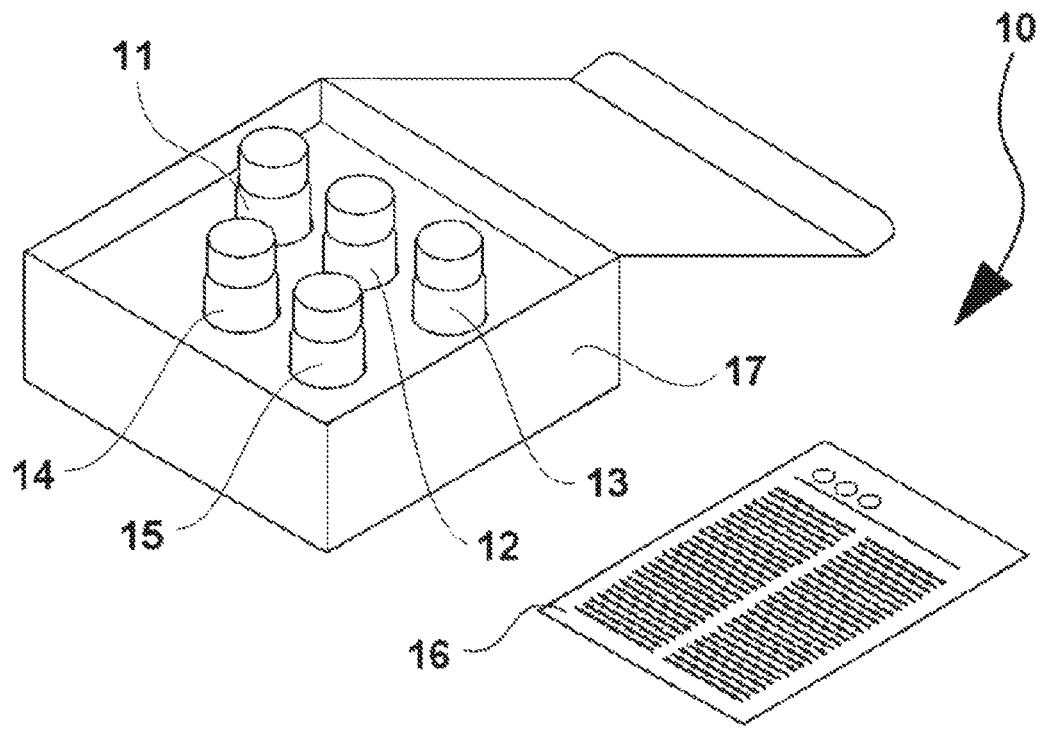

[FIG. 12B]
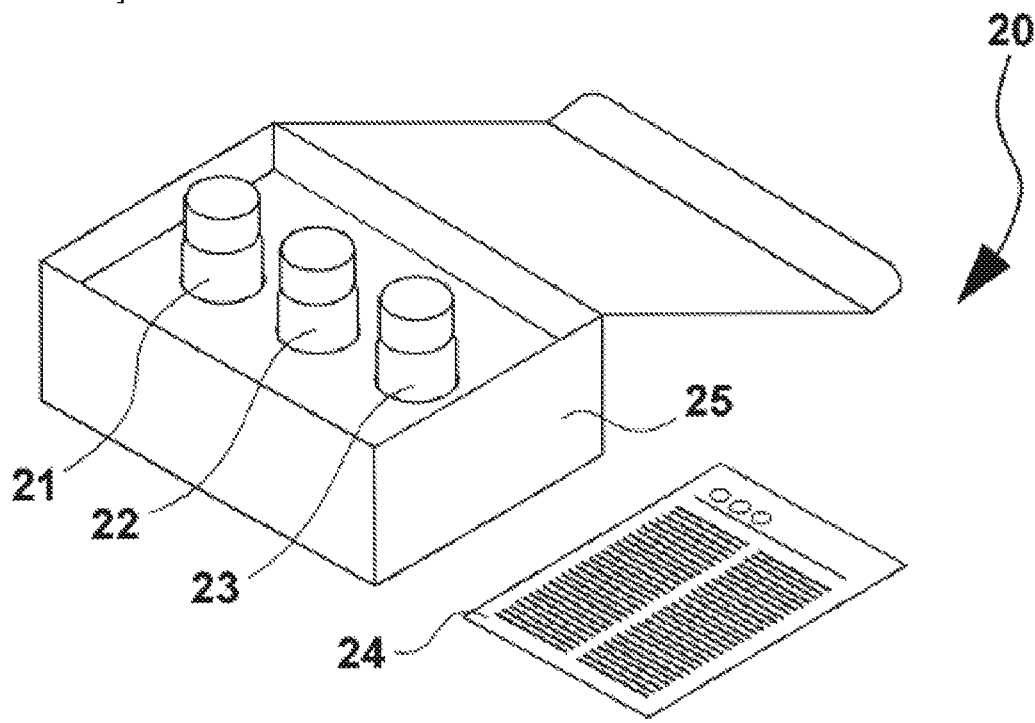
[FIG. 12C]
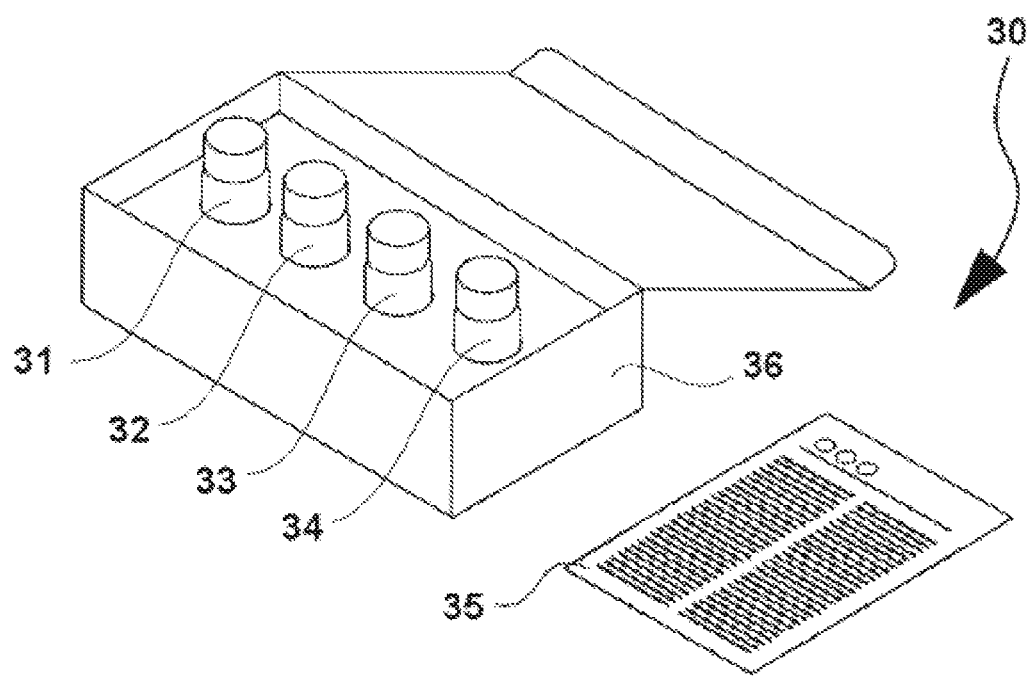

[FIG. 12D]
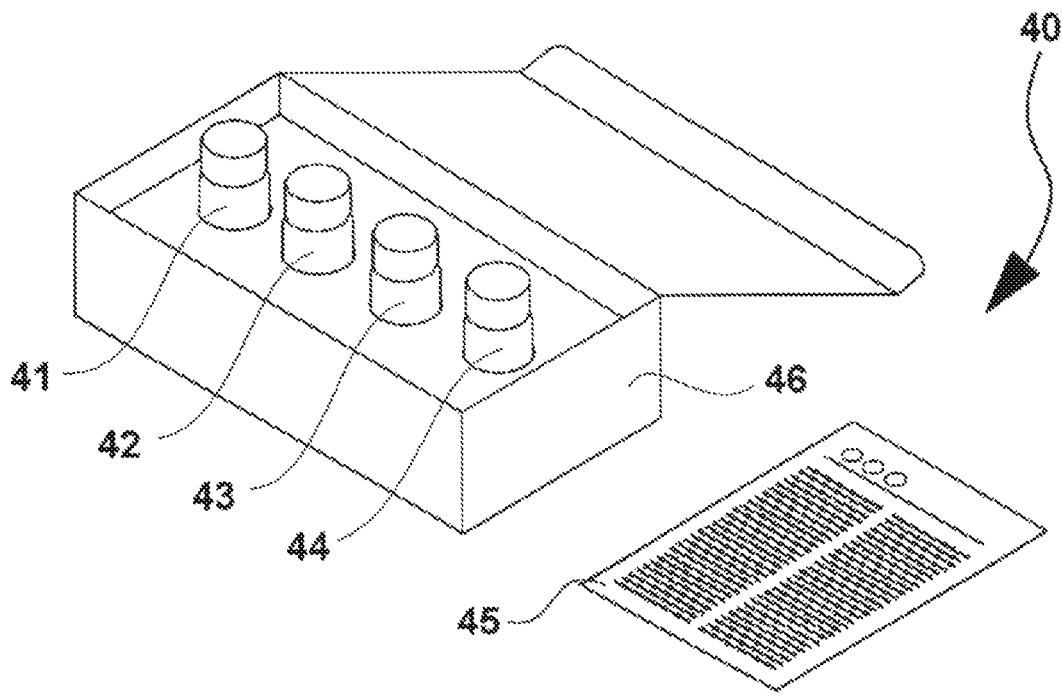
[FIG. 12E]
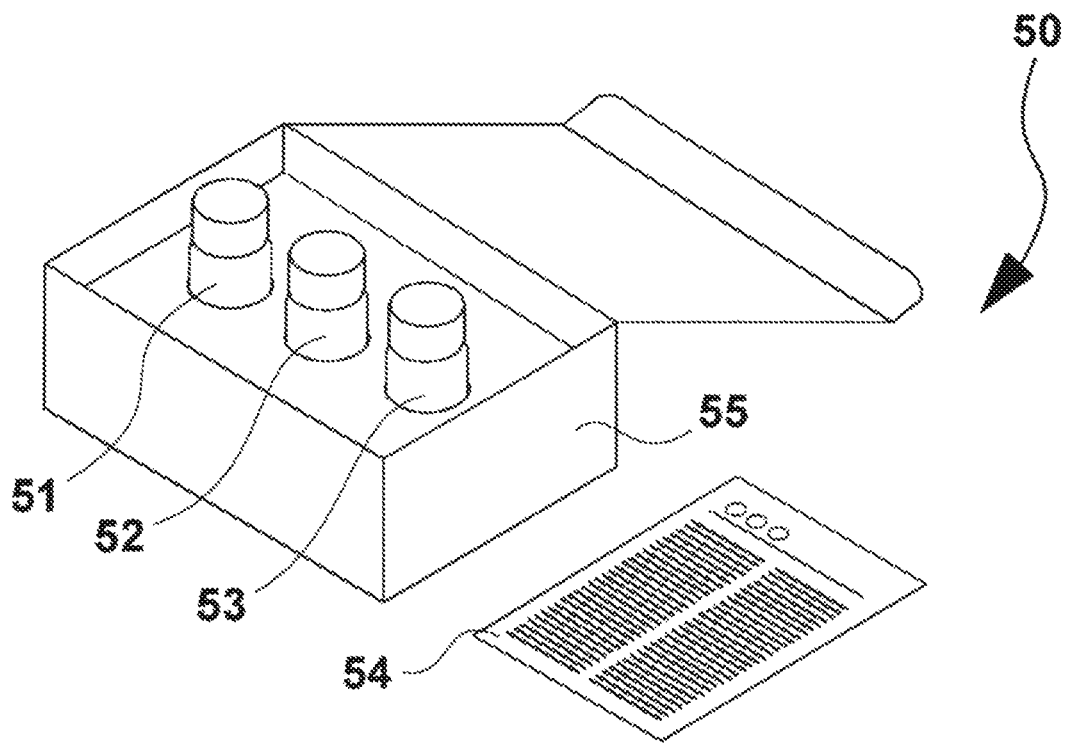

[FIG. 13]
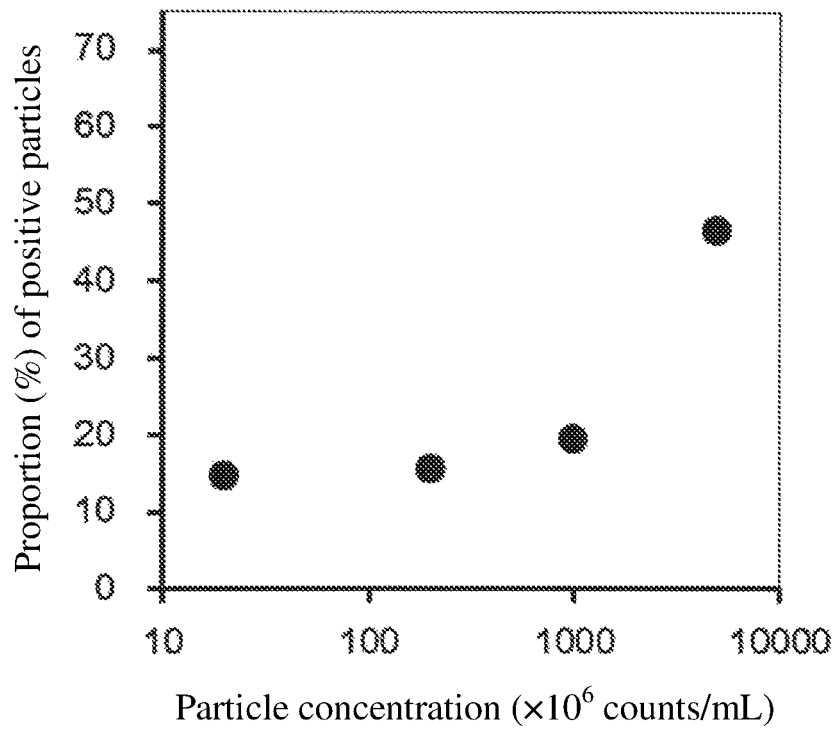
[FIG. 14]
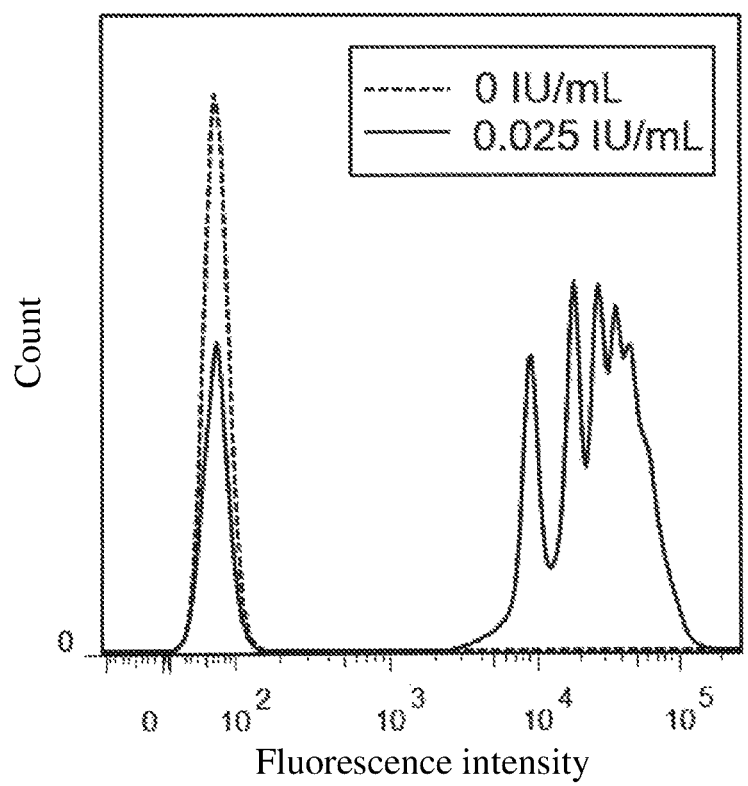

[FIG. 15]
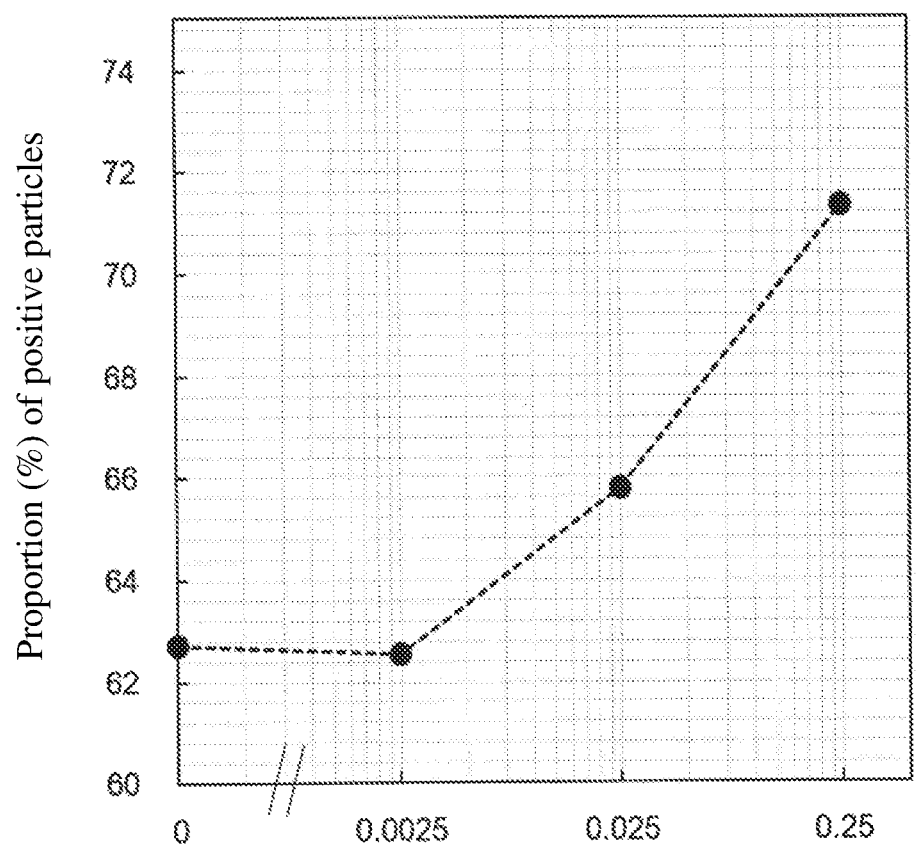
[FIG. 16A]
Average particle size of fluorescent particles: 160 nm
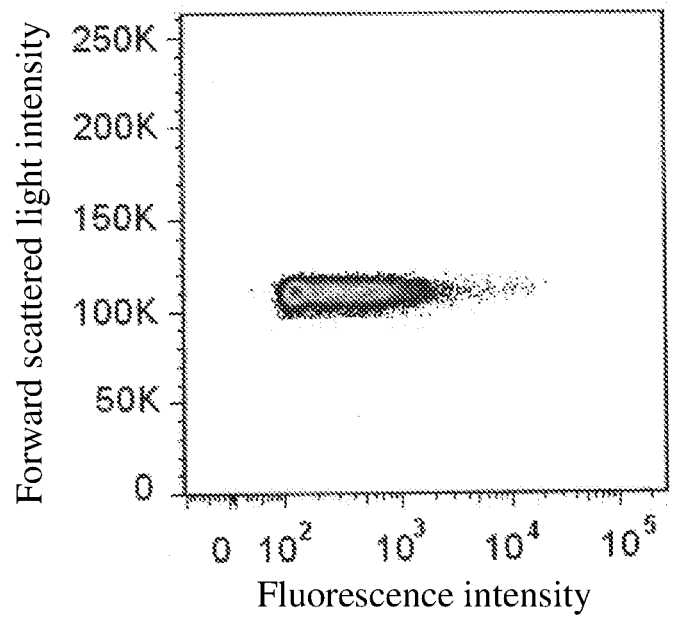

[FIG. 16B]
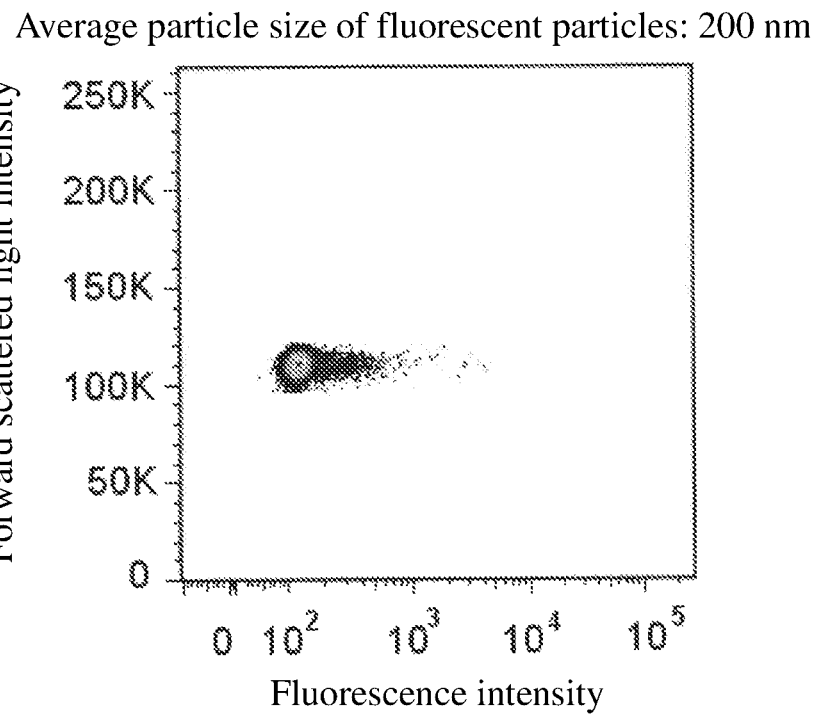
[FIG. 16C]
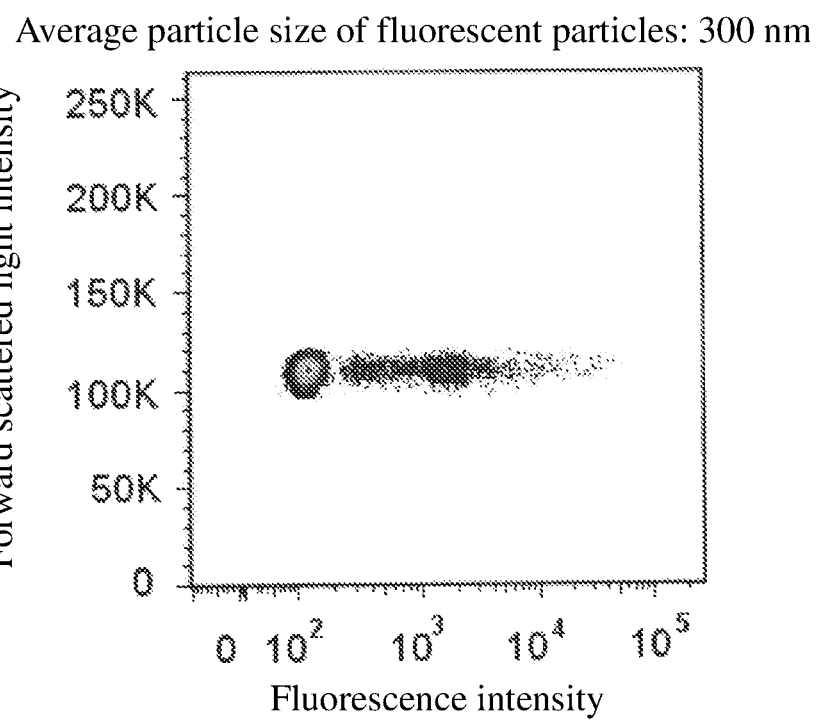

[FIG. 16D]
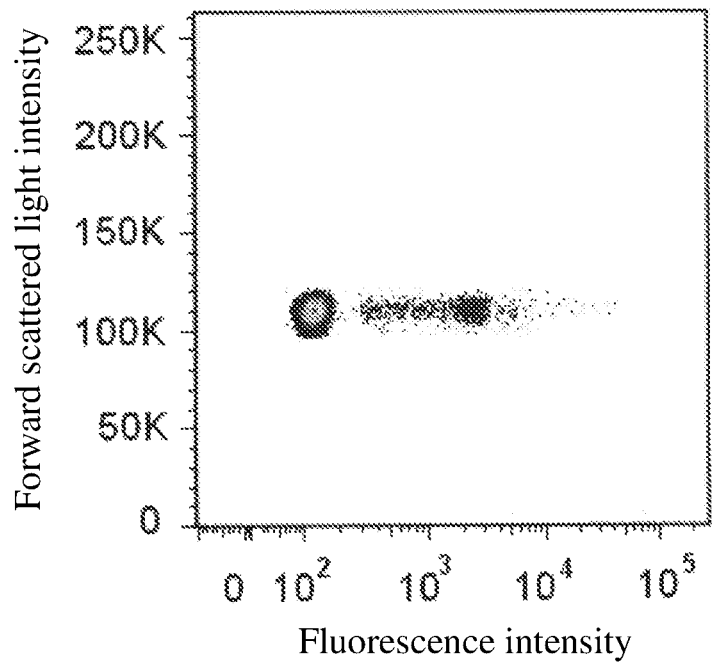
[FIG. 16E]
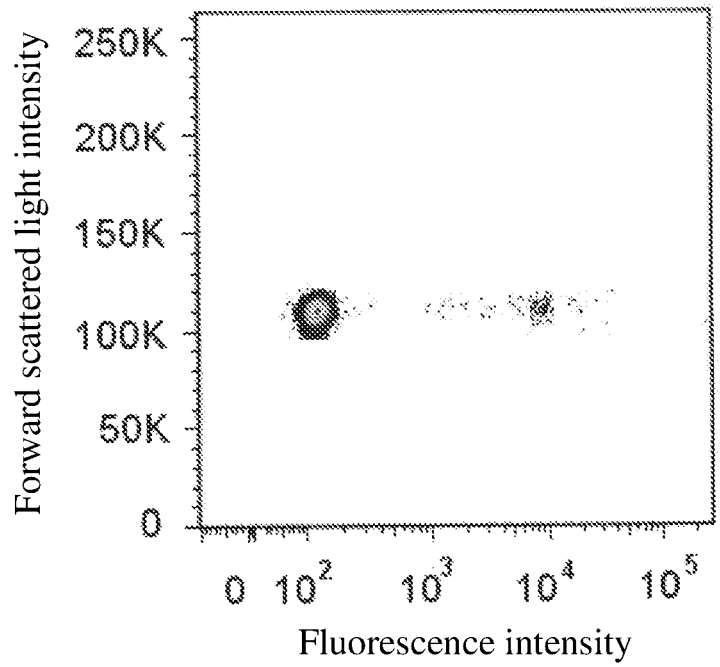

[FIG. 17A]
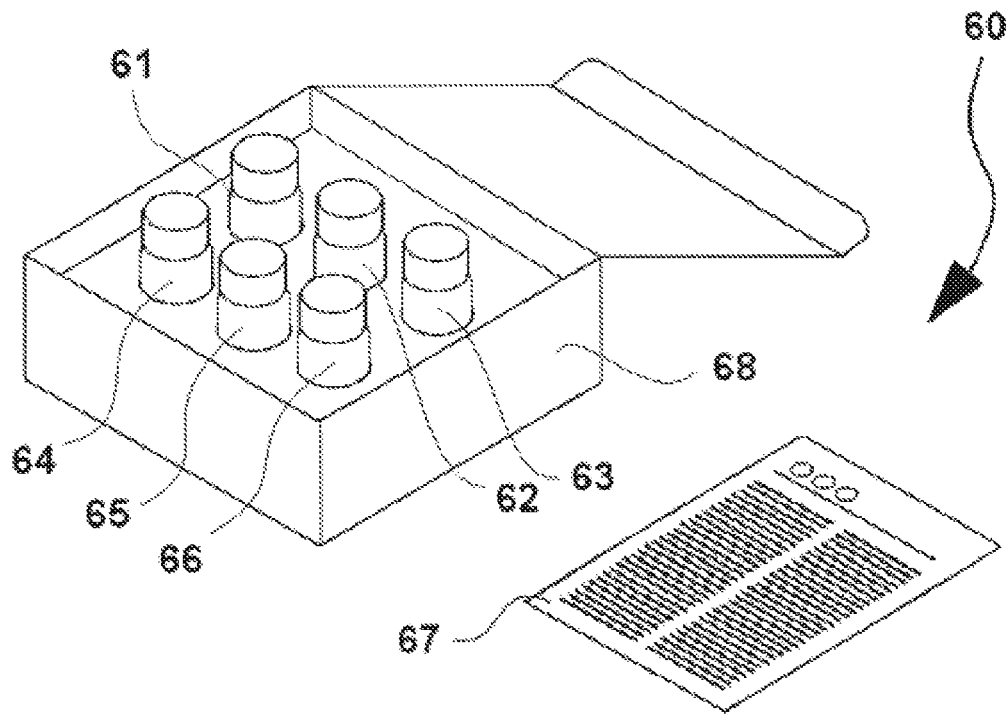
[FIG. 17B]
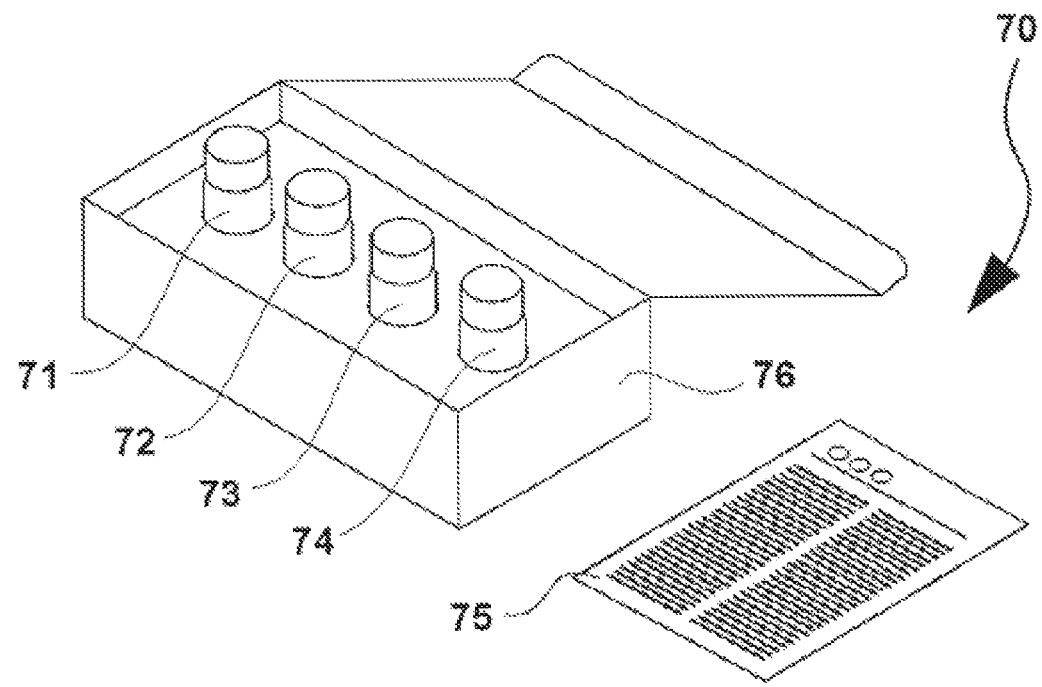

[FIG. 17C]
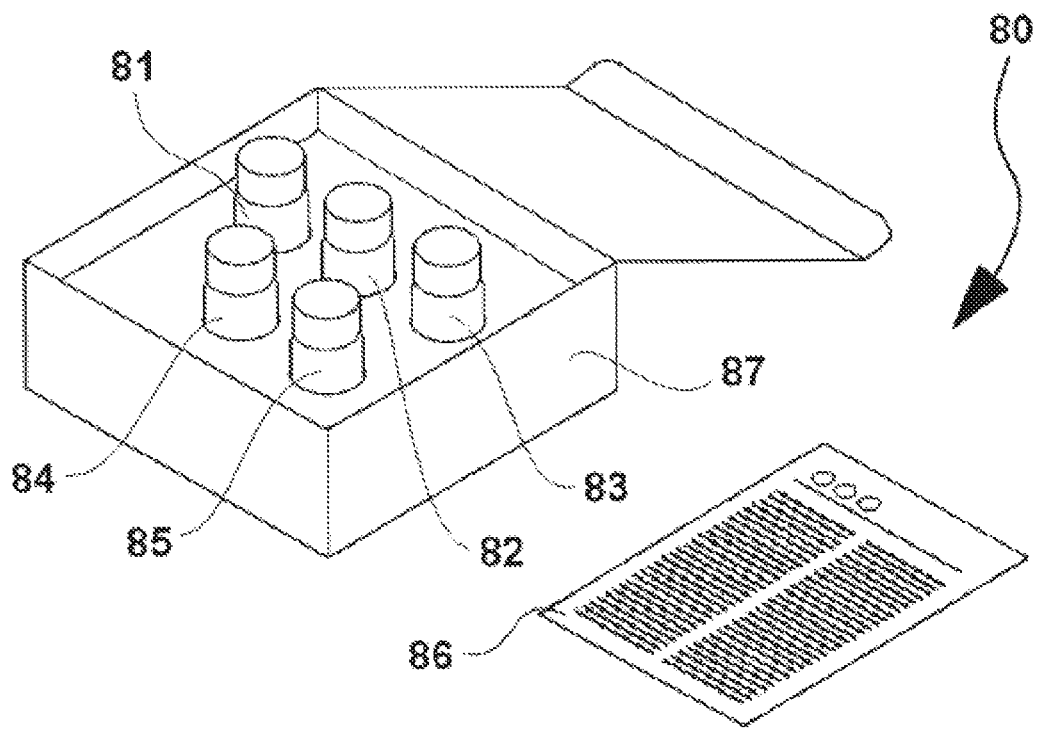
[FIG. 17D]
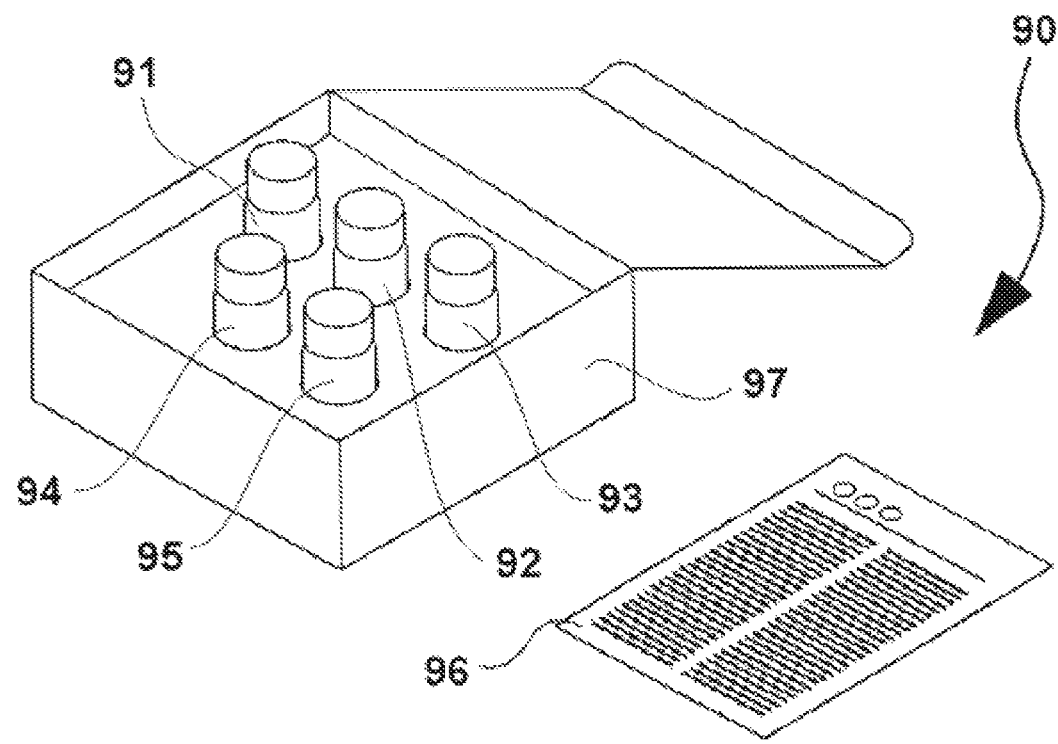

[FIG. 17E]
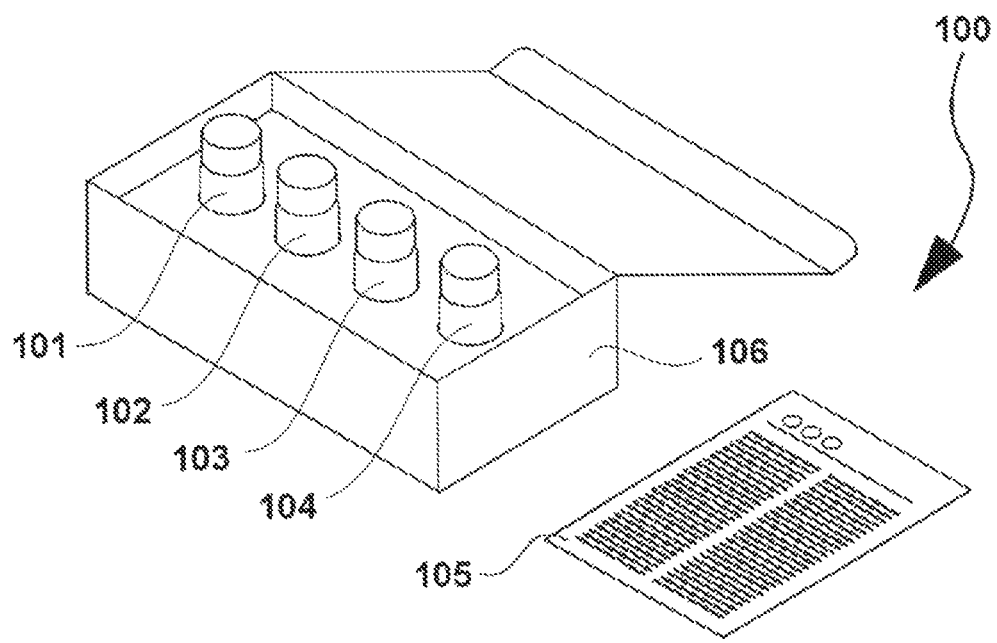

[FIG. 18]
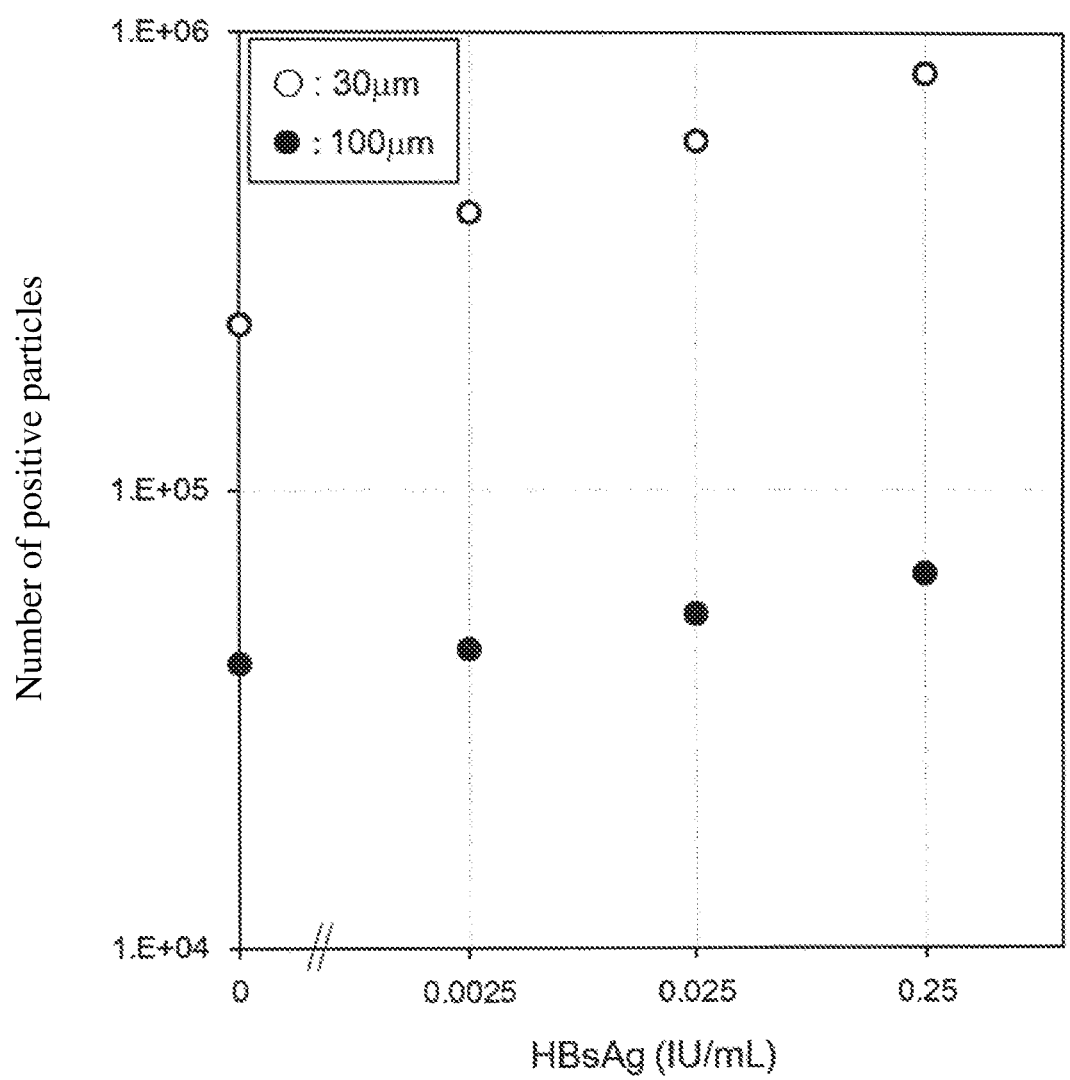

[FIG. 19A]
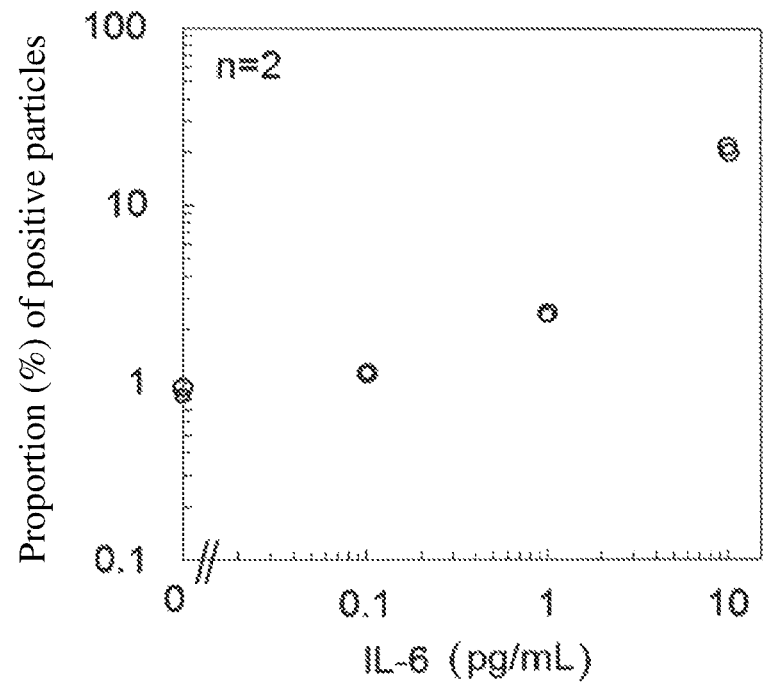
[FIG. 19B]
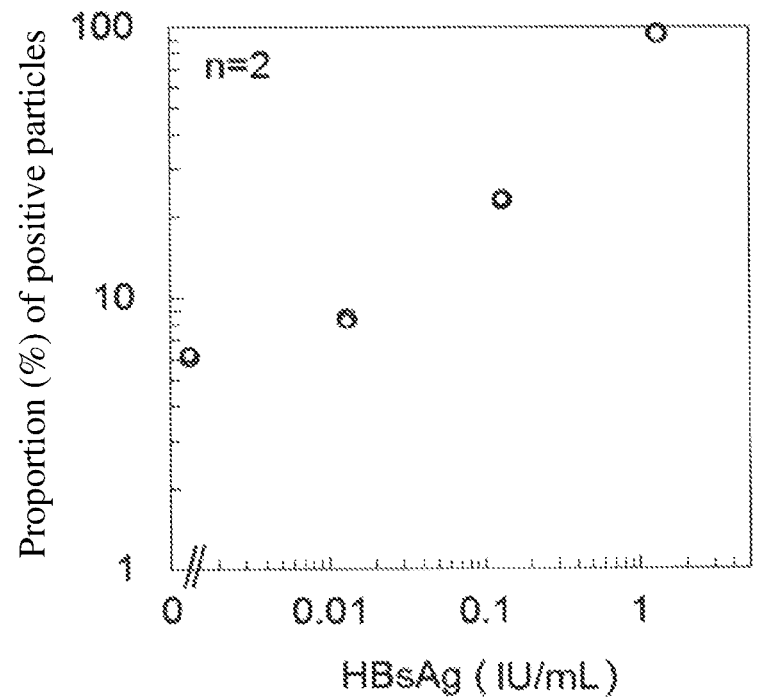

[FIG. 20]
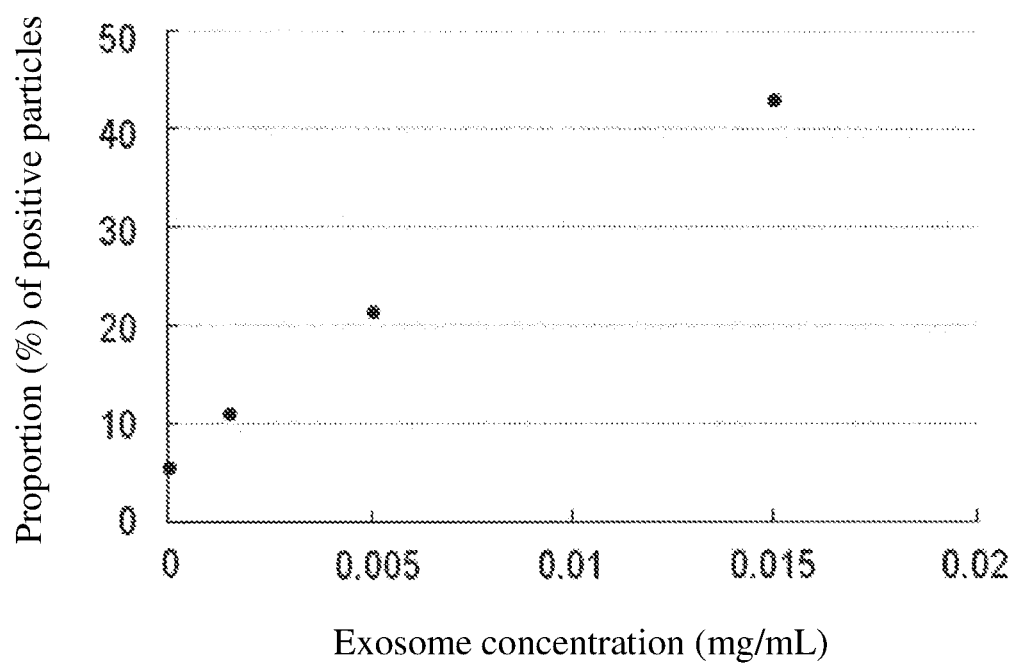

METHOD FOR DETECTING ANALYTE

TECHNICAL FIELD

The present invention relates to a method for detecting an analyte in a sample.

BACKGROUND ART

As a method for detecting an analyte in a sample, a digital detection method is known. The digital detection method is a method for detecting an analyte with high sensitivity by detecting an analyte individually at a time.

As an example of the digital detection method, the method described in US 2011/0212848 A is known. The method described in US 2011/0212848 A is called digital ELISA, and US 2011/0212848 A describes that an analyte can be detected individually at a time. According to this method, an immune complex containing a labeling enzyme and one molecule of the analyte is first formed on each of beads. After the addition of an enzyme substrate, the beads are enclosed one by one in a compartmentalized region such as microwell or droplet (hereinafter, also referred to simply as "compartment"). This compartment is spatially isolated from another compartment, and no compound exchange is performed between compartments. Therefore, an enzymatic reaction occurs, and fluorescence is generated in a compartment containing beads in each of which the immune complex is formed. On the other hand, no enzymatic reaction occurs, and fluorescence is not generated in a compartment containing beads in each of which no immune complex is formed. The analyte is digitally detected individually at a time based on a positive compartment where fluorescence is detected.

SUMMARY

In the digital detection method, a compartment containing one molecule of the analyte is required for detection as described above. In order to prepare a plurality of compartments containing one molecule of the analyte from a mixed solution containing a plurality of molecules of the analyte, a special device such as a device for forming a microwell or droplet is required, and the detection operation is complicated. It is an object of the present invention to provide a method capable of performing digital detection without performing the compartmentalization as described above.

The present invention provides a method for detecting an analyte in a sample. This method includes the following steps of forming on each of carrier particles a complex containing a first capture substance capable of binding to an analyte, one molecule of the analyte, a second capture substance capable of binding to the analyte, and a catalyst; immobilizing a reaction product on each of the carrier particles by reacting the catalyst in the complex with a substrate; and detecting the analyte by detecting the carrier particles on each of which the reaction product is immobilized.

BRIEF DESCRIPTION OF DRAWINGS

FIGS. 1(A) to 1(D) are schematic diagrams illustrating the method of the present embodiment. FIG. 1(A) shows a step of mixing a plurality of carrier particles on each of which a first capture antibody is immobilized, a sample containing an antigen, and a second capture antibody labeled with HRP. FIG. 1(B) shows complex formation on each of the carrier particles. FIG. 1(C) shows a catalytic reaction in which fluorescent tyramide is radicalized. FIG. 1(D) shows immobilization of fluorescent tyramide to each of the carrier particles.

FIGS. 2(A) to 2(E) are schematic diagrams illustrating the method of the present embodiment in the case of using detection particles (fluorescent particles). FIG. 2(A) shows a step of mixing a plurality of carrier particles on each of which a first capture antibody is immobilized, a sample containing an antigen, and a second capture antibody labeled with HRP. FIG. 2(B) shows complex formation on each of the carrier particles. FIG. 2(C) shows a catalytic reaction in which tyramide is radicalized. FIG. 2(D) shows immobilization of tyramide to each of the carrier particles and addition of fluorescent particles. FIG. 2(E) shows immobilization of the fluorescent particles to the carrier particles on each of which tyramide is immobilized.

FIGS. 3(A) to 3(E) are schematic diagrams illustrating the method of the present embodiment in the case of using a substrate (multi-substrate) containing a support and a plurality of substrate molecules. FIG. 3(A) shows a step of mixing a plurality of carrier particles on each of which a first capture antibody is immobilized, a sample containing an antigen, and a second capture antibody labeled with HRP. FIG. 3(B) shows complex formation on each of the carrier particles. FIG. 3(C) shows a catalytic reaction in which tyramide in a multi-substrate is radicalized. FIG. 3(D) shows immobilization of multi-substrates to each of the carrier particles. FIG. 3(E) shows a state in which multi-substrates are further bound to the multi-substrates immobilized on each of the carrier particles.

FIG. 4 is a graph showing the result of Example 2.

FIG. 5 shows microscopic images taken in Example 3.

FIG. 6 is an enlarged view of a microscopic image (HBs antigen concentration of 0.25 IU/mL) taken in Example 3.

FIG. 7 is a graph showing the result of Example 4.

FIG. 8 is a graph showing the result of Comparative Example 1.

FIG. 9A is a graph showing the fluorescence intensity distribution of blank magnetic particles.

FIG. 9B is a graph showing the fluorescence intensity distribution of magnetic particles to each of which HRP polymer (400-mer) is bound.

FIG. 9C is a graph showing the mean fluorescence intensity of positive beads in magnetic particles to which blank magnetic particles and HRP polymers having various degrees of polymerization are bound.

FIG. 9D is a graph showing the relationship between the ratio of positive particles and the degree of polymerization of HRP polymer.

FIG. 10 shows microscopic images (HBs antigen concentrations 0, 0.00025, 0.0025 and 0.025 IU/mL) taken in Example 6.

FIG. 11 is a graph showing the relationship between the ratio of positive particles and the concentration of HBs antigen.

FIG. 12A is a schematic diagram showing an example of the reagent kit of the present embodiment.

FIG. 12B is a schematic diagram showing an example of the reagent kit of the present embodiment.

FIG. 12C is a schematic diagram showing an example of the reagent kit of the present embodiment.

FIG. 12D is a schematic diagram showing an example of a reagent kit of the present embodiment.

FIG. 12E is a schematic diagram showing an example of the reagent kit of the present embodiment.

FIG. 13 is a graph showing the relationship between the ratio of positive particles and the concentration of carrier particles.

FIG. 14 is a graph (HBs antigen concentrations 0, and 0.025 IU/mL) showing the fluorescence intensity distribution of carrier particles on which fluorescent particles are immobilized.

FIG. 15 is a graph showing the relationship between the ratio of positive particles and the concentration of HBs antigen.

FIG. 16A is a graph showing the fluorescence intensity distribution of carrier particles on which fluorescent particles having an average particle size of 160 nm are immobilized.

FIG. 16B is a graph showing the fluorescence intensity distribution of carrier particles on which fluorescent particles having an average particle size of 200 nm are immobilized.

FIG. 16C is a graph showing the fluorescence intensity distribution of carrier particles on which fluorescent particles having an average particle size of 300 nm are immobilized.

FIG. 16D is a graph showing the fluorescence intensity distribution of carrier particles on which fluorescent particles having an average particle size of 400 nm are immobilized.

FIG. 16E is a graph showing the fluorescence intensity distribution of carrier particles on which fluorescent particles having an average particle size of 500 nm are immobilized.

FIG. 17A is a schematic diagram showing an example of the reagent kit of the present embodiment.

FIG. 17B is a schematic diagram showing an example of the reagent kit of the present embodiment.

FIG. 17C is a schematic diagram showing an example of the reagent kit of the present embodiment.

FIG. 17D is a schematic diagram showing an example of the reagent kit of the present embodiment.

FIG. 17E is a schematic view showing an example of the reagent kit of the present embodiment.

FIG. 18 is a graph showing the result of Example 12.

FIG. 19A is a graph showing the correlation between the concentration of IL-6 and the proportion (%) of positive particles to the number of particles contained in a population having an average particle size of 2.8 µm.

FIG. 19B is a graph showing the correlation between the concentration of HBs antigen and the proportion (%) of the number of positive particles to the number of particles contained in a population having an average particle size of 4.5 µm.

FIG. 20 is a graph showing the correlation between the exosome concentration and the proportion (%) of positive particles.

DESCRIPTION OF EMBODIMENTS

A sample applied to the method of the present embodiment is not particularly limited. Examples of the sample include biological samples such as blood and lymph fluid, excreta such as urine and feces, environmental samples such as river water, sea water and soil, and the like.

The detection in the present embodiment is preferably carried out in a solution, and thus, when the sample is not in a liquid state, it is preferable to prepare the sample in a liquid form by appropriately subjecting the sample to pretreatment. Here, the "liquid" sample is not limited to a solution in which a solute is completely dissolved in a solvent, but also includes a suspension in which fine solids such as cells are suspended, a sol, and the like. As a pretreatment method, a known method is appropriately selected according to the kind of an analyte. For example, when the sample is a solid tissue extracted from a living body, the solid tissue is homogenized in a pretreatment liquid containing a surfactant, and pretreatment such as separation and removal of crushed materials by centrifugation or the like can be performed. In this case, the supernatant after centrifugation can be applied to the subsequent step.

The liquid sample may be subjected to pretreatment. By extracting and purifying specific components by a known method, impurities can be removed, and an analyte can be detected with higher accuracy. For example, blood is subjected to pretreatment to be formed into a serum or plasma state, which can be used for the detection described later.

The kind of the analyte is not particularly limited as long as a capture substance described later for the analyte is present, or such a capture substance can be produced. In the case where the capture substance described later is an antibody, any substance having antigenicity can be an object to be detected. Examples thereof include, but are not particularly limited to, antibodies, proteins, nucleic acids, physiologically active substances, vesicles, bacteria, viruses, polypeptides, haptens, therapeutic drugs, metabolites of therapeutic drugs, and the like. The antibody can also be an antigen. Here, the polypeptides include not only proteins having a large number of amino acid residues but also polypeptides having a small number of amino acid residues, which are generally called peptide. Polysaccharides also include sugar chains present on the surface of a cell or protein, and lipopolysaccharides that are outer membrane components of bacteria. Examples of the physiologically active substance include, but are not particularly limited to, cell growth factors, differentiation-inducing factors, cell adhesion factors, enzymes, cytokines, hormones, sugar chains, lipids, and the like. The vesicle is not particularly limited as long as it is a small vesicle composed of a membrane. The vesicle may contain a liquid phase therein. Examples of the vesicle include extracellular vesicles such as exosome, microvesicle and apoptotic body, artificial vesicles such as liposome, and the like.

[Formation of Complex]

In the present embodiment, upon detection of an analyte in a sample, a complex containing one molecule of an analyte on a carrier particle is formed. The complex includes a first capture substance immobilized on a carrier particle, an analyte captured by the first capture substance, a second capture substance that captures the analyte, and a catalyst. By this complex formation, one molecule of the analyte is immobilized on the carrier particle. Hereinafter, a carrier particle that captures an analyte is referred to as a "positive particle", and a carrier particle that does not capture an analyte is referred to as a "negative particle".

As used herein, "immobilize" refers to the state in which a substance is directly or indirectly captured by a carrier particle. It includes the state in which a substance is directly captured by a carrier particle in any binding manner and the state in which a substance is indirectly immobilized via another substance immobilized on the carrier particle. For example, when avidin or streptavidin (hereinafter, also referred to as "avidin") is bound to a carrier particle and an antibody labeled with biotin is bound to the carrier particle, this biotin-labeled antibody is indirectly immobilized on the carrier particle. Furthermore, an antigen bound to the biotin-labeled antibody is also indirectly immobilized on the carrier particle. Besides binding between avidin and biotin, it is also conceivable to immobilize a substance via a linker known in the art.

The first capture substance and the second capture substance, as well as a third capture substance and a fourth capture substance described later (hereinafter, also collectively referred to as "capture substance") are not particularly limited as long as they are substances that specifically bind to the analyte. For the binding between the capture substance and the analyte, various modes are conceivable depending on the kind of the analyte. For example, conceivable are binding utilizing antigen-antibody reaction, binding utilizing complementary chain formation of nucleic acid, binding between a receptor and a ligand, and the like. Therefore, the capture substance can be appropriately selected depending on the kind of the analyte, such as an antibody, an antigen, an oligonucleotide probe, a receptor, a ligand which binds to the receptor, and an aptamer. When the capture substance and the analyte are nucleic acids, it is preferable that the capture substance is a single-stranded nucleic acid.

It is preferable that the first capture substance and the second capture substance bind to different positions of the analyte. This is because, when the substances bind to the same position, there is a possibility that the binding of the first capture substance and the binding of the second capture substance compete with each other, and thus both the first capture substance and the second capture substance cannot bind to the analyte. For example, when the capture substance is an antibody and the analyte is an antigen, it is preferable that the epitope of the analyte to which the first capture substance binds is different from the epitope of the analyte to which the second capture substance binds. When the capture substance and the analyte are nucleic acids, it is preferable that the base sequence of the analyte to which the first capture substance binds is different from the base sequence of the analyte to which the second capture substance binds. The first capture substance and the second capture substance may be the same kind of substances or different kinds of substances. Examples of being the same kind of substances include a case where all the capture substances are antibodies. Examples of being the different kinds of substances include a case where the first capture substance is an aptamer and the second capture substance is an antibody. The relationship between the first capture substance and the second capture substance described herein applies to a third capture substance and a fourth capture substance described later as well.

As used herein, the "antibody" includes monoclonal antibodies, polyclonal antibodies, and fragments of antibodies such as Fab and F(ab')2. The "nucleic acid" as a capture substance includes not only DNA and RNA, but also artificial nucleic acids such as Peptide Nucleic Acid (PNA), Locked Nucleic Acid (LNA) and Bridged Nucleic Acid (BNA). Alternatively, the nucleic acid may contain a plurality kinds of them.

The kind of the catalyst is not limited, but is selected in consideration of the kind of a substrate described later. The catalyst is preferably an enzyme. Examples of the enzyme include peroxidase, alkaline phosphatase (ALP), glucosidase, polyphenol oxidase, and the like. As the peroxidase, horseradish peroxidase (HRP) is preferably used. As the glucosidase, β-glucosidase is preferably used.

The catalyst may be a monomer or a polymer obtained by polymerizing a plurality of molecules. Whether to use the monomer or polymer catalyst may be determined depending on the substance used as a label described later, particularly depending on the intensity of a signal generated by the substance. When the catalyst is a polymer, one complex will contain a large number of catalysts. Since more reaction products can be produced with one complex, a signal generated from the carrier particle is amplified. The number of monomers contained in the polymer (hereinafter, also referred to as "degree of polymerization") is not particularly limited. For example, a catalyst having a degree of polymerization of the polymer of 2 or more and several hundreds or less, and preferably 50 or more and 400 or less can be used.

The catalyst may be previously bound to the second capture substance, or may be bound to the second capture substance at the time of mixing the second capture substance and the analyte. For example, when the second capture substance is modified with biotin and avidin is bound to the catalyst, the catalyst is bound to the second capture substance when the second capture substance is mixed with the analyte.

In the present embodiment, it is preferable to use a carrier particle having a small particle size. The reason is as follows. In the method of the present embodiment, a reaction product is immobilized on a carrier particle by the reaction between the catalyst and the substrate described later. Here, when the particle size of the carrier particle is large, the ratio of the area of the region to which the reaction product is bound to the surface area of the carrier particle is small. Then, there is a possibility that a positive particle is misidentified as a negative particle, depending on the direction in which the particle is observed, the magnitude of a signal from a label described later, and the like. On the other hand, when the particle size of the carrier particle is small, the surface area of the particle becomes small, and thus the ratio of the area of the region to which the reaction product is bound is high. Therefore, it is possible to reduce the possibility of misidentifying a positive particle as a negative particle.

In the present embodiment, it is preferable to use carrier particles having an average particle size of 100 μm or less. More preferably, the average particle size is 90 μm or less, 80 μm or less, 70 μm or less, 60 μm or less, 50 μm or less, or 40 μm or less. Particularly preferably, the average particle size is 30 μm or less, 25 μm or less, 20 μm or less, 15 μm or less, 10 μm or less, 5 μm or less, 4 μm or less, or 3 μm or less. From the viewpoint of the detection limit of a detection method described later and ease of handling in experimental operation, the average particle size is preferably 100 nm or more, and more preferably 200 nm or more. The average particle size of the carrier particles is a volume-based median diameter measured with a particle size distribution measuring apparatus by laser diffraction/scattering method. Examples of the particle size distribution measuring apparatus include "Microtrac MT3000 II" manufactured by NIKKISO CO., LTD., and the like. As used herein, the "particle size" means a diameter.

The material of the carrier particles is not particularly limited. Metal particles, resin particles, silica particles and the like can be used. Specific examples of the metal particles include gold, silver, copper, iron, aluminum, nickel, manganese, titanium, oxides thereof, and the like. Further, alloys thereof may be used. Specific examples of the resin particles include polystyrene particles, latex particles, and the like. The carrier particles may be magnetized particles (hereinafter also referred to as "magnetic particles").

The surface of the carrier particle is preferably treated with a blocking agent. Treatment with a blocking agent suppresses nonspecific adsorption of substances contained in the sample or reagent on the surface of the carrier particles. As the blocking agent, a known substance such as albumin, casein or skim milk can be used.

The shape of the carrier particle is not particularly limited. According to a method commonly used in the art as the method for producing particles each g a small particle size as described above, the shape is close to a sphere, but it is not necessary to be an exact sphere. It may be a shape closed to a rectangular parallelepiped, a cube, or a triangular pyramid.

The complex is formed by mixing a sample containing an analyte, a reagent containing a plurality of carrier particles (hereinafter, also referred to as a arrier particle reagent"), a first capture substance, a second capture substance, and a catalyst. The order of mixing is not particularly limited.

The carrier particle reagent is preferably a liquid reagent. The carrier particle reagent may be obtained by dispersing or suspending the carrier particles in an aqueous solvent such as water or a buffer solution. The component of the solvent is not particularly limited as long as it does not substantially inhibit complex formation or catalytic reaction.

The carrier particle concentration (number of carrier particles/volume of enzyme reaction solution) during the enzymatic reaction is preferably $5 \times 10^4$ counts/mL or more and less than $5 \times 10^9$ counts/mL, more preferably $5 \times 10^4$ counts/mL or more and $1 \times 10^9$ counts/mL or less, and particularly preferably $1 \times 10^5$ counts/mL or more and $1 \times 10^8$ counts/mL or less. Here, the carrier particle concentration relates to an average distance between carrier particles. For example, when tyramide described below is used as a substrate, the diffusion distance of radicalized tyramide is estimated to be several tens nm. Therefore, the average distance between carrier particles during the enzymatic reaction may be 100 times or more, preferably 1000 times or more, and more preferably 10000 times or more the diffusion distance of radicalized tyramide. That is, the average distance between carrier particles is 3 μm or more, preferably 30 μm or more, and more preferably 300 μm or more. Theoretically, when the average distance between carrier particles is 3 μm or more, the radicalized tyramide does not reach carrier particles not involved in the production of the radicalized tyramide.

The relationship between the carrier particle concentration and the distance between carrier particles will be described based on Table 1 below. In a digital detection method, $5 \times 10^4$ or more and $1 \times 10^7$ or less carrier particles are usually used. In addition, the amount of a reaction solution in a digital detection method is usually 1 μL or more and 1000 μL or less. When the distance between carrier particles in the case where the carrier particles are uniformly dispersed is calculated from the number of the carrier particles and the amount of the reaction solution, for example, the results are shown in Table 1. As shown in Table 1, the maximum value of the carrier particle concentration at which the distance between carrier particles is 3 μm or more is estimated to be $1 \times 10^9$ counts/mL.

TABLE 1

| Number of particles | Liquid volume (μL) | Concentration (counts/mL) | Average interparticle distance (μm) |
|---|---|---|---|
| $5 \times 10^4$ | 1 | $5 \times 10^7$ | 24 |
|  | 10 | $5 \times 10^6$ | 85 |
|  | 100 | $5 \times 10^5$ | 280 |
|  | 1000 | $5 \times 10^4$ | 895 |
| $1 \times 10^6$ | 1 | $1 \times 10^9$ | 3 |
|  | 10 | $1 \times 10^8$ | 16 |

TABLE 1-continued

| Number of particles | Liquid volume (μL) | Concentration (counts/mL) | Average interparticle distance (μm) |
|---|---|---|---|
|  | 100 | $1 \times 10^7$ | 59 |
|  | 1000 | $1 \times 10^6$ | 196 |
| $1 \times 10^7$ | 1 | $1 \times 10^{10}$ | −0.01 |
|  | 10 | $1 \times 10^9$ | 3 |
|  | 100 | $1 \times 10^8$ | 16 |
|  | 1000 | $1 \times 10^7$ | 59 |

In the present embodiment, since an excessive amount of the carrier particles is mixed with respect to the number of molecules of the analyte, in theory, one molecule of the analyte is captured per one carrier particle. The capture of the analyte on the carrier particle is thought to occur according to the Poisson distribution. Based on this, the number of the carrier particles to be added to the reaction system is preferably 10 times or more, and more preferably 100 times or more the expected number of molecules of the analyte. On the other hand, when the number of the carrier particles is too large, detection takes time. From this viewpoint, the number of the carrier particles can be $10^8$ times or less the number of molecules of the analyte.

[Reaction between Catalyst and Substrate]

After forming the complex on the carrier particle, a substrate is caused to react with the catalyst in the complex. This reaction is preferably performed in a solution containing carrier particle on each of which the complex is immobilized, and the substrate. This makes it possible to perform the reaction between the catalyst in the complex and the substrate in a state in which the carrier particles are dispersed in the solution. By dispersing the carrier particles, the distance between the carrier particles is maintained. Therefore, a reaction product is immobilized on a carrier particle that immobilizes the catalyst that has produced the reaction product, but is not substantially immobilized on another carrier particle, that is, a carrier particle that does not immobilize the catalyst that has produced the reaction product. That is, in the method of the present embodiment, each carrier particle is not compartmentalized in the step of immobilizing the reaction product on the carrier particle. This makes it possible to digitally detect one molecule of the analyte without performing compartmentalization. When the reaction product is radicalized tyramide, it is preferable that the distance between carrier particles is kept at least 3 μm by dispersing carrier particles. As described above, the distance of 3 μm is about 100 times the scattered distance of the radicalized tyramide, which is a sufficiently long distance. Therefore, when the distance between carrier particles is 3 μm or more, the radicalized tyramide will be substantially immobilized only on the carrier particle immobilizing the catalyst (HRP) that has produced the radicalized tyramide.

When the carrier particles are particles precipitated in a solution, it is preferable to disperse the carrier particles in the solution while causing the catalyst to react with the substrate. A means for dispersing the carrier particles is not particularly limited, and examples thereof include stirring, shaking, mixing by inversion, and the like.

The substrate is preferably has a label (hereinafter, a substrate having a label is also referred to as a "labeled substrate"). In this case, a reaction product having a label is generated by a catalytic reaction. In the case of using a substrate having no label, the label can be also added to the reaction product after the catalytic reaction. For example, first, a substrate having avidin is caused to react with a catalyst to produce a reaction product having avidin. Next, a labeled substance having biotin is bound to this reaction product having avidin. It is also possible to use a substrate having biotin in place of the substrate having avidin, and to use a labeled substance having avidin in place of the labeled substance having biotin. In this way, after the production of the reaction product, the label can also be immobilized on the reaction product.

The kind of the substrate depends on the kind of the catalyst. When HRP is used as the catalyst, tyramide can be used as the substrate. Tyramide is a p-phenol derivative having an amino group, and is radicalized by the catalytic action of HRP in the presence of hydrogen peroxide. Here, a radical refers to a compound having an unpaired electron. Since a radical is highly reactive, it reacts immediately with other substances in the vicinity and become stable. The radicalized tyramide produced by HRP binds nonspecifically to an aromatic compound in the vicinity. This aromatic compound is, for example, a blocking agent immobilized on a carrier particle, a first capture substance, an analyte, a second capture substance, and a tyrosine residue or tryptophan residue contained in a catalyst. As described above, a radical of the radicalized tyramide has a short lifetime, and thus is substantially immobilized only on the carrier particle immobilizing HRP that has produced the radicalized tyramide, and does not bind to another carrier particle. Accordingly, a large number of tyramides are immobilized on the carrier particles on each of which the analyte is captured. A large number of labels can be immobilized on carrier particles by adding a label to tyramide prior to the catalytic reaction or by binding a label to tyramide immobilized on the carrier particle after the catalytic reaction. On the other hand, when the analyte is not captured, HRP is not also captured, and thus substantially no radicalized tyramide is produced, and a label is not also immobilized. When HRP is used as the catalyst and tyramide is used as the substrate, radicalized tyramide is produced as a product of the catalytic reaction. This radicalized tyramide binds to an aromatic compound in the vicinity and loses unpaired electrons to become tyramide. Here, the "reaction product" includes not only the radicalized tyramide produced after the catalytic reaction, but also tyramide which has lost unpaired electrons after the catalytic reaction and binding to the aromatic compound.

When ALP is used as the catalyst, a chromogen such as Fast red can be used as the substrate. When Fast red reacts with ALP to release a phosphate group, it is possible to bind to naphthol, and shows reddish brown color. Fluorescence also occurs. In this case, naphthol is immobilized directly or indirectly on a carrier particle on a carrier particle. This causes Fast red releasing a phosphate group to immobilize on a carrier particle via naphthol.

When β-glucosidase or polyphenol oxidase is used as the catalyst, oleuropein can be used as the substrate. Oleuropein has a glutaraldehyde-like structure in the secoiridoid glycoside part by enzymatic reaction. The reaction product will have a plurality of aldehyde groups within the compound. An aldehyde group has a strong reactivity with a primary amine. This reaction is described in Konno et al., Proceedings of National Academy of Science, 96, 9154-64 (1999). An aldehyde group of the reaction product is bound to a primary amine of an amino acid residue immobilized on a carrier particle, so that the reaction product is immobilized on the carrier particle. A label having a primary amine is bound to the aldehyde not used for binding with the carrier particle, so that the label can be immobilized on the carrier particle.

The label is not particularly limited as long as it is a substance that generates a detectable signal. The detectable signal is preferably an optical signal. For example, a change in intensity or wavelength of light generated from a reaction solution can be used as a signal. Specifically, examples of the detectable signal include signals that are often used in the art, such as fluorescence, color development, and light emission. Examples of the substance that generates a signal include fluorescent substances, light-emitting substance, chromogenic substances, and the like.

When a fluorescent substance is used as the label, it is preferable that the fluorescent substance includes an aromatic π conjugated polymer structure from the viewpoint of fluorescence intensity. Here, the aromatic π conjugated polymer structure intends a polymer structure composed of a π conjugated system having an aromatic ring as a main chain. Such a polymer structure is described in U.S. Pat. Nos. 8,158,444 and 8,575,303. In a fluorescent substance containing an aromatic π conjugated polymer structure, when the polymer structure portion is excited by excitation light, the excitation energy moves from the polymer structure to the fluorescent substance, due to Forster (or fluorescence) resonance energy transfer (FRET). Accordingly, the fluorescent substance is indirectly excited to generate fluorescence. It is known that the intensity of the fluorescence generated at this time is amplified more than the case where the fluorescent substance is directly excited alone. That is, the aromatic π conjugated polymer structure plays a role of a molecular antenna for collecting excitation light.

The fluorescent substance is not particularly limited, and may be selected from known fluorescent dyes used in technical fields such as molecular biology and immunology. Examples of the fluorescent dyes include fluorescein, rhodamine, Texas Red, tetramethylrhodamine, carboxyrhodamine, phycoerythrin, 6-FAM (trademark), Cy (registered trademark) 3, Cy (registered trademark) 5, Alexa Fluor (registered trademark) series, and the like.

Preferably, the fluorescent substance including the aromatic π conjugated polymer structure is represented by the following formula (I):

[Chemical Formula 1]

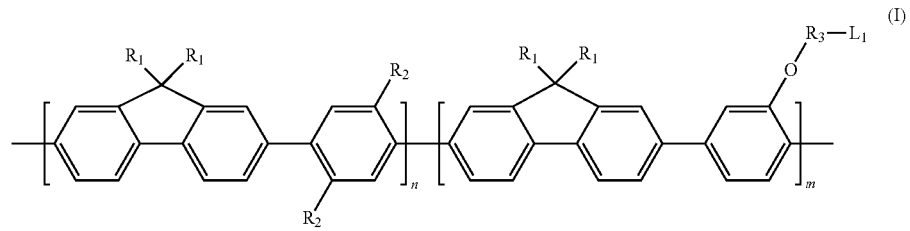

wherein, $R_1$s are each independently —$(CH_2)_x(OCH_2CH_2)_y$—, —$(CH_2)_x(OCH_2CH_2)_yOCH_3$, —$(CH_2CH_2O)_y(CH_2)_x$—, a ω-ammonium alkyl salt, a ω-ammonium alkoxy salt, a ω-sulfonate alkyl salt or a ω-sulfonate alkoxy salt;

$R_2$s are each independently a hydrogen atom, a halogen atom, hydroxy, alkoxy, cyano, —$(CH_2)_x(OCH_2CH_2)_y$—, —$(CH_2)_x(OCH_2CH_2)_yOCH_3$, —$(CH_2CH_2O)_y(CH_2)_x$—, a ω-ammonium alkyl salt, a ω-ammonium alkoxy salt, a ω-sulfonate alkyl salt or a ω-sulfonate alkoxy salt;

$R_3$ is —$(CH_2)_a$— or —$(CH_2CH_2O)_b(CH_2)_c$—;

$L_1$ is a fluorescent substance;

m and n are the same or different from each other, and are an integer of 1 or more and 10,000 or less, preferably an integer of 1 or more and 5000 or less, and more preferably an integer of 1 or more and 1,000 or less;

xs are each independently an integer of 0 or more and 20 or less, and preferably an integer of 0 or more and 10 or less;

ys are each independently an integer of 1 or more and 50 or less, and preferably an integer of 1 or more and 24 or less;

as are each independently an integer of 1 or more and 20 or less, and preferably an integer of 1 or more and 10 or less;

bs are each independently an integer of 1 or more and 50 or less, and preferably an integer of 1 or more and 24 or less; and cs are each independently an integer of 0 or more and 20 or less, and preferably an integer of 0 or more and 10 or less.

As used herein, an "alkyl" refers to a linear, branched or cyclic saturated hydrocarbon group having 1 to 24 carbon atoms which may be unsubstituted or substituted in at least one position, and includes polycyclic compounds. Examples of the alkyl group include unsubstituted or substituted methyl, ethyl, n-propyl, isopropyl, n-butyl, s-butyl, t-butyl, n-pentyl, isopentyl, neopentyl, n-hexyl, n-heptyl, n-octyl, n-decyl, hexyloctyl, tetradecyl, hexadecyl, eicosyl, tetracosyl, and the like, and cycloalkyl groups such as cyclopropyl, cyclobutyl, cyclopentyl, cyclohexyl, cycloheptyl, cyclooctyl, adamantyl, and norbornyl. A "lower alkyl" refers to an alkyl group having 1 to 6 carbon atoms, and preferably 1 to 4 carbon atoms. Examples of a substituent in the substituted alkyl group include hydroxyl, cyano, alkoxy, =O, =S, —$NO_2$, —SH, halogen, haloalkyl, heteroalkyl, carboxylalkyl, amine, amide, and thioether.

An "alkoxy" denotes an "—O-alkyl" group, and the alkyl is as defined above. A "lower alkoxy" group intends an alkoxy group having 1 to 6 carbon atoms, and preferably 1 to 4 carbon atoms.

A "halogen atom" represents fluorine, chlorine, bromine, or iodine. Preferably, the halogen atom is fluorine.

A fluorescent substance having an aromatic π conjugated polymer structure is commercially available, and for example, a series of Brilliant Violet (trademark) (Sirigen Ltd) is available. Among them, Brilliant Violet (trademark) 421 is particularly preferable.

Binding of a reaction product to a carrier particle is started immediately after the reaction between a catalyst and a substrate. The excess amount of substrate added to the reaction system turns into a reaction product by a catalyst and accumulates in a carrier particle. Accordingly, even when only one molecule of an analyte is immobilized, a large amount of a reaction product is immobilized on a carrier particle, and the detection sensitivity is improved.

In the present embodiment, a detection particle may be used as one kind of label. By immobilizing a detection particle on a carrier particle as well, the optical properties of the carrier particles can be changed as described later. Therefore, in the method of the present embodiment, a detection particle may be further immobilized on a carrier particle on which a complex is formed. Preferably, a detection particle is immobilized via a reaction product on a carrier particle on which the reaction product is immobilized. Specifically, a detection particle may be immobilized on a carrier particle by causing a catalyst to react with a substrate to which the detection particle is previously bound. Alternatively, after the reaction between a catalyst and a substrate, a detection particle may be bound to a reaction product immobilized on a carrier particle. For example, first, a substrate having biotin is caused to react with a catalyst to immobilize a reaction product having biotin on a carrier particle. Next, a detection particle having avidin is bound to the reaction product having biotin. It is also possible to use a substrate having avidin in place of the substrate having biotin, and to use a detection particle having biotin in place of the detection particle having avidin. In this way, the detection particle can be immobilized on the carrier particle. In the present embodiment, an analyte can be detected by detecting the carrier particle on which the detection particle is immobilized via the reaction product.

The material of the detection particles is not particularly limited, and particles prepared by metal and a compound thereof, resin, silica or the like can be used likewise the carrier particles. The detection particles may be particles each containing a substance that emits a detectable signal, such as a fluorescent substance or a light-emitting substance. As such detection particles, particles each containing a fluorescent substance (hereinafter, also referred to as "fluorescent particles") are preferable. Fluorescent particles themselves are known in the art. For example, series of Estapor (registered trademark) Fluorescent Microspheres (Merck KGaA), and the like are generally available. Fluorescent particles are larger in size and generate a larger signal (e.g., fluorescence intensity) than fluorescent dyes. Therefore, when fluorescent particles are used as the detection particles, the detection accuracy of an analyte is improved.

The average particle size of the detection particles is preferably 5% or more, and more preferably 10% or more smaller than the average particle size of the carrier particles. For example, when the average particle size of the carrier particles is 1 μm, the average particle size of the detection particles is preferably 50 nm or more, and more preferably 100 nm or more. The larger the particle size of the detection particle is, the clearer the distinction between positive particles and negative particles tends to be. However, when the particle size of the detection particle is too large, there is a possibility that the detection particle is easily separated from the carrier particle. Therefore, the average particle size of the detection particles is preferably smaller than the average particle size of the carrier particles.

In the present embodiment, a complex containing a support and a plurality of substrate molecules (hereinafter, also referred to as a "multi-substrate") may be used as a substrate. The support may be any substance capable of holding a plurality of substrate molecules in a state capable of reacting with the catalyst. The number of the substrate molecules is not particularly limited, and can be appropriately determined according to the kind of the support, the mode of holding, and the like.

As the multi-substrate, a support on which a plurality of substrate molecules is immobilized can be used. The substrate molecules may be immobilized on a support via a linker known in the art, or may be immobilized on a support via binding between avidin and biotin, or the like. For example, a plurality of substrate molecules having biotin may be caused to react with a support to which a plurality of avidins is bound, and a plurality of substrate molecules may be immobilized on the support via binding between biotin and avidin. It is also possible to use a plurality of substrate molecules having avidin in place of the plurality of substrate molecules having biotin, and to use a support having a plurality of biotins in place of the support having avidin.

In the present embodiment, a support that generates a detectable signal may be used. When the substrate molecule does not have the above label, positive particles can be detected by detecting a signal from the support. When the substrate molecule has a label, positive particles can be detected by detecting at least one of a signal from the support and a signal from the label. The support that generates a signal preferably contains a fluorescent substance or a light-emitting substance. Among them, a support containing a fluorescent substance is particularly preferable. Alternatively, the support itself may be a fluorescent substance. As a support that generates a fluorescent signal, for example, the fluorescent particles above, fluorescent proteins, a series of Qdot (registered trademark) nanocrystals (Invitrogen), and the like are generally available. Qdot (registered trademark) nanocrystals are fluorescent substances each having a particle size of 10 to 20 nm containing a semiconductor material (cadmium mixed with selenium or tellurium) as a core.

The kind of the substrate molecule of the multi-substrate depends on the kind of a catalyst as described above. The substrate molecule contained in the multi-substrate may be of one kind or of two or more kinds. In the case of using a support which does not generate a signal, it is preferable that the substrate molecule has the above label. When the catalyst is HRP, tyramide is preferred as the substrate molecule. As described later, a multi-substrate having a plurality of tyramides can provide many scaffolds to which radicalized tyramides as a reaction product bind. Thus, a signal stronger than the case of using one molecule of substrate is obtained.

As shown in FIG. 1, when one molecule of tyramide is used as a substrate, a radicalized tyramide produced by the reaction with a catalyst can bind to a blocking agent, a first capture substance, a second capture substance, an analyte and a catalyst on a carrier particle. On the other hand, when a multi-substrate having a plurality of tyramides is used, radicalized tyramides can also bind to a multi-substrate itself as shown in FIG. 3. For example, when at least one tyramide molecule among a plurality of tyramide molecules of a multi-substrate is radicalized by a catalyst, the one tyramide molecule reacts with a complex on a carrier particle or the carrier particle to be immobilized. At this time, radicalized tyramides in another multi-substrate can bind to the complex on the carrier particle or the tyramide molecule not immobilized on the carrier particle. This is because tyramide itself is also an aromatic compound. That is, it is possible to increase a site where the radicalized tyramide reacts by using a multi-substrate. Therefore, by using a multi-substrate, more reaction products can be immobilized on the carrier particle than the case of using one tyramide molecule. At this time, a stronger signal is generated when the tyramide has a label or the support has a signal generating substance.

[Detection]

As used herein, the "detection" includes qualitative detection, quantitative detection, and semi-quantitative detection. The "semi-quantitative detection" indicates the content (or concentration) of an analyte in a sample stepwisely, such as "negative", "weak positive", "positive", and "strong positive".

As described above, when a label binds to a carrier particle, the optical properties of the carrier particles change. The optical properties refer to, for example, the wavelength of light emitted by the carrier particle. In the present embodiment, since a fluorescent substance, a light-emitting substance or the like is used as a label, the optical properties include fluorescence, light emission or the like of a specific wavelength. In a detection step, an analyte is detected by detecting the optical information of the carrier particle. As the optical information, the intensity of light of a specific wavelength emitted from the carrier particle can be used. For example, in the case of detection by a flow cytometer described later, it is possible to use a peak value, integrated value and the like of a detected light signal as intensity of light. In the present embodiment, since a fluorescent substance, a light-emitting substance or the like is used as a label, the optical information includes fluorescence intensity, light emission intensity, or the like.

Even when a detection particle is bound to the carrier particle, the optical properties of the carrier particles change. For example, the optical properties include scattering of light that occurs when irradiating the carrier particle with light. The detection particle is immobilized on the carrier particle, so that the overall size and the surface area are increased, and thus scattered light generated by light irradiation to the carrier particle changes. In this case, the optical information includes scattered light intensity. When the detection particle is a particle containing a fluorescent substance, a light-emitting substance, or the like, the optical properties may include fluorescence, light emission or the like of a specific wavelength. In this case, the optical information includes fluorescence intensity, light emission intensity, and the like. As described above, an analyte is detected by detecting the optical information of the carrier particle on which the detection particle is immobilized.

The method for detecting carrier particles is not particularly limited as long as it is a method capable of detecting carrier particles one by one. For example, carrier particles can be detected using a microscope, a flow cytometer, an image sensor, or the like.

An image sensor is a detection system that includes a semiconductor element that convers incident light into an electric signal and does not use an optical system such as a lens. Examples of the image sensor include a CMOS image sensor, a CCD image sensor, and the like.

A flow cytometer refers to a device capable of counting fine particles such as carrier particles. The flow cytometer includes a flow cell having a thin tube and a detector. A suspension containing carrier particles is introduced into a flow cell, and each of the carrier particles passing through the flow cell is detected by a detector. The detector includes, for example, a light source that irradiates the carrier particles passing through the flow cell with light, and a light receiving element that detects optical information such as fluorescence and scattered light generated when the carrier particles are irradiated with light. In a further embodiment, the detector photographs each of the carrier particles passing through the flow cell. A flow cytometer having a function of imaging is called an imaging flow cytometer. In the case of imaging a fluorescence image with an imaging flow cytometer, a detector includes a light source that irradiates carrier particles with excitation light.

In the case of using a microscope or an image sensor, it is possible to image the visual field and detect each of carrier particles using the imaged data. The carrier particles at the time of imaging may stand still or flow.

In the case of using a flow cytometer, it is possible to introduce carrier particles into a flow cell and detect optical information such as fluorescence and scattered light generated from each of the carrier particles passing through the flow cell. It is also possible to detect electrical information such as electric resistance generated when each of the carrier particles passes through the flow cell. In the case of using an imaging flow cytometer, it is possible to image each of the carrier particles passing through a flow cell and detect each of the carrier particles using the imaged data.

In the detection, a signal, that is, the optical information of each carrier particle may be measured, and the measured value may be compared with a preset predetermined threshold value. As a result of the comparison, it is preferable to detect carrier particles whose measured value is equal to or greater than a predetermined threshold as positive particles. This is because it is conceivable, for example, that the carrier particle themselves have a background signal depending on the material of the carrier particles. For example, in the case of detecting fluorescence, the carrier particles themselves may have autofluorescence, thus it is preferable to perform the above comparison step.

The predetermined threshold value is not particularly limited as long as it is a value that can accurately discriminate between positive particles and negative particles. For example, it is possible to measure a plurality of signals of positive particles and a plurality of signals of negative particles, and to set to a value at which positive particles and negative particles can be most accurately discriminated. In order to suppress false negatives, the minimum value of the plurality of signals of positive particles may be set as a predetermined threshold value. In order to suppress false positives, the maximum value of the plurality of signals of negative particles may be set as a predetermined threshold value.

When a fluorescent substance is used as a label, a fluorescence microscope can be used. It is possible to image the visual field with a fluorescence microscope, measure fluorescence intensity generated from each of carrier particles by analyzing the imaged data, and detect carrier particles each having a fluorescence intensity equal to or greater than a predetermined threshold as positive particles. In the case of using a flow cytometer, carrier particles are first passed through a general-purpose flow cytometer. When a fluorescent substance is used as a label, it is possible to irradiate each of carrier particles with excitation light from a light source of the flow cytometer, receive a fluorescence signal by a light receiving element, and detect carrier particles based on the intensity of the fluorescence signal (for example, peak value).

According to the above detection method, the number of positive particles can be counted. In theory, since only one molecule of an analyte is immobilized on one positive particle, the number of positive particles is substantially the same as the number of molecules of the analyte.

The sum of the areas generating signals of positive particles may be calculated, not counting the number of positive particles. In the case of detecting fluorescence as a signal, the "area of positive particles" may be the area of the portion where fluorescence of positive particles is generated. In this case, the sum of the areas of positive particles can be calculated as the sum of the areas of the portions emitting fluorescence equal to or greater than a certain intensity. The "area" may be a surface area of particle, or may be an area on a two-dimensional image acquired by imaging a particle.

Since the sum of the areas of positive particles correlates with the number of molecules of an analyte, it is possible to quantitatively determine the analyte based on the sum. The ratio of the sum of the areas of negative particles to the sum of the areas of positive particles, the ratio of the sum of the areas of all particles to the sum of the areas of positive particles, and the like can also be used for the quantitative determination of the analyte. The "area of negative particles" and the "area of all particles" may be a surface area of a particle, or may be an area on a two-dimensional image acquired by imaging a particle. The same is true in the case of detecting light emission.

Upon the detection, all of carrier particles added to a sample may be subjected to the detection, or a part of carrier particles added to a sample may be subjected to the detection. For example, in the case of detection with a flow cytometer, it is conceivable to introduce a part of carrier particles subjected to the reaction into a flow cell for detection. In the case of detection with a microscope or an image sensor, it is conceivable to perform the detection based on imaging data of a part of visual field.

It is preferable to count the number of the carrier particles subjected to detection (hereinafter, also referred to as "all carrier particles"). For example, when a flow cytometer is used, the carrier particles can be easily counted based on information such as fluorescence, electrical resistance, and scattered light. In the case of using a microscope or an image sensor, all carrier particles can be counted by image processing after imaging the visual field. As described later, when the number of negative particles is counted, the number of all carrier particles may be calculated by adding the number of negative particles and the number of positive particles.

Furthermore, the number of negative particles may be calculated. For example, it can be calculated by subtracting the number of positive particles from the number of all carrier particles counted by the above method. In the case of using a flow cytometer, carrier particles having a signal less than a predetermined threshold value can be counted as negative particles. In the case of using a microscope, the number of negative particles can be counted by image processing after imaging.

The concentration of the analyte is calculated based on the number of positive particles. For example, the number of positive particles is defined as the number of molecules of the analyte contained in a sample, and the concentration and the like can be calculated. Further, the concentration can be calculated by using the proportion of positive particles in all carrier particles, the value of ratio between positive particles and negative particles, and the like. Preferably, the detection method of the present embodiment is carried out using a standard sample containing an analyte having a known concentration, a calibration curve is prepared, and the analyte is subjected to quantitative determination based on the calibration curve.

When a part of carrier particles added to a sample is subjected to detection, the number of molecules of the analyte can be calculated by considering what degree of the carrier particles added to the sample was subjected to the detection. For example, the number of molecules of the analyte can be calculated using the value obtained by multiplying the proportion of positive particles in all carrier particles by the number of the carrier particles added to the sample.

In the method of the present embodiment, compartmentalization of carrier particles is not performed. As described above, compartmentalization means that carrier particles are spatially isolated so that no compound exchange is performed between compartments. An example of a conventional digital detection method of performing compartmentalization includes a method of storing carrier particles one by one in a well and sealing each well with a hydrophobic solvent (see, for example, US 2013/345088 A). Another example includes a method of preparing a plurality of droplets in an oil phase and enclosing carrier particles one by one in each droplet (see, for example, U.S. Pat. No. 8,236,574). According to these methods, a reaction system including one carrier particle and one molecule of an analyte is constructed in each compartment, and a solvent containing the analyte in the compartment generates a signal. The number of the compartments generating a signal is counted, and the analyte is subjected to quantitative determination based on the counting results. In these conventional methods, since a signal is generated from the solvent, digital detection is impossible unless the carrier particles are compartmentalized. In the method of the present embodiment, substantially, a reaction product having a label is immobilized only on a carrier particle on which a catalyst that has produced the reaction product is immobilized, and only the carrier particle on which the analyte is immobilized changes in optical properties. No signal is substantially detected from the solvent. Therefore, digital detection can be performed without compartmentalization. According to the method of the present embodiment, a special device or instrument for compartmentalization is unnecessary, and the detection operation can be simplified. In the present embodiment, the detection step may be performed in a solution containing a plurality of carrier particles. In this case, each carrier particle is not compartmentalized in the solution.

Here, the method of the present embodiment in the case of detecting an antigen as an analyte, the method using an antibody as a capture substance (hereinafter, also referred to as "capture antibody"), HRP as a catalyst, tyramide labeled with a fluorescent substance as a labeled substrate (hereinafter, also referred to as "fluorescent tyramide"), will be described with reference to the schematic diagram of FIG. 1. In FIG. 1, a carrier particle is represented by a black circle; an antibody is represented by a Y shape; an antigen is represented by a hollow triangle; HRP is represented by a black diamond; a substrate is represented by a white circle; a fluorescent substance is represented by a star; and a radical is represented by an asterisk (*).

When a plurality of carrier particles on each of which a first capture antibody is immobilized, a sample containing an antigen, and a second capture antibody labeled with HRP are mixed with one another (FIG. 1(A)), a complex containing one molecule of antigen and capture antibodies on the carrier particle is formed (FIG. 1(B)). Next, fluorescent tyramide is mixed. The fluorescent tyramide added in an excess amount is successively radicalized by HRP (FIG. 1(C)). The radicalized fluorescent tyramide is immobilized on a complex containing the HRP and a carrier particle on which the complex is immobilized. Accordingly, a large number of fluorescent substances are immobilized on the carrier particle (positive particle in FIG. 1(D)). At this time, since radicals react only with substances in the vicinity, fluorescent tyramide is not immobilized on a carrier particle which does not capture the complex (negative particle in FIG. 1(D)). Thereafter, the carrier particles are passed through a flow cytometer, and the fluorescence intensity of the carrier particles is measured one by one. The number of the positive particles is counted, and the analyte is subjected to quantitative determination.

In the case of using tyramide having biotin (hereinafter, also referred to as "biotinylated tyramide") and a fluorescent substance having avidin, the method of the present embodiment can be carried out, for example, by the following steps. First, when a plurality of carrier particles on each of which a first capture antibody is immobilized, a sample containing an antigen, and a second capture antibody labeled with HRP are mixed with one another, a complex containing one molecule of antigen and capture antibodies on the carrier particle is formed. Next, biotinylated tyramide is mixed. The biotinylated tyramide added in an excess amount is successively radicalized by HRP. The radicalized biotinylated tyramide is immobilized on a complex containing the HRP and a carrier particle on which the complex is immobilized. A large number of fluorescent substances are immobilized on the carrier particle by bringing the carrier particle on which biotinylated tyramide is immobilized into contact with the fluorescent substance having avidin. Since radicals react only with substances in the vicinity, biotinylated tyramide is not immobilized on a carrier that does not capture the complex. Therefore, the fluorescent substance having avidin is also not immobilized. Thereafter, the carrier particles are passed through a flow cytometer, and the fluorescence intensity of the carrier particles is measured one by one. The number of the positive particles is counted, and the analyte is subjected to quantitative determination.

As a further embodiment, the case where an antigen is detected as an analyte with use of an antibody as a capture substance, HRP as a catalyst, biotinylated tyramide as a substrate, and fluorescent particles having avidin as detection particles, will be described with reference to the schematic diagram of FIG. 2. In FIG. 2, a carrier particle is represented by a black circle; an antibody is represented by a Y shape; an antigen is represented by a hollow triangle; HRP is represented by a black diamond; a substrate is represented by a white circle; a fluorescent particle is represented by a gray circle; and a radical is represented by an asterisk (*).

When a plurality of carrier particles on each of which a first capture antibody is immobilized, a sample containing an antigen, and a second capture antibody labeled with HRP are mixed with one another (FIG. 2(A)), a complex containing one molecule of antigen and capture antibodies on the carrier particle is formed (FIG. 2(B)). Next, biotinylated tyramide is mixed. The biotinylated tyramide added in an excess amount is successively radicalized by HRP (FIG. 2(C)). The radicalized biotinylated tyramide is immobilized on a complex containing the HRP and a carrier particle on which the complex is immobilized. Accordingly, a large number of biotinylated tyramides are immobilized on the carrier particle (carrier particle on the right in FIG. 2(D)). At this time, since radicals react only with substances in the vicinity, biotinylated tyramide is not immobilized on a carrier particle which does not capture the complex (carrier particle on the left in FIG. 2(D)). Here, when fluorescent particles having avidin are added (FIG. 2(D)), the fluorescent particles are further immobilized on the carrier particle on which the biotinylated tyramide is immobilized via the binding between biotin and avidin (positive particle in FIG. 2(E)). Thereafter, the carrier particles are passed through a flow cytometer, and the fluorescence intensity of the carrier particles is measured one by one. The number of the positive particles is counted, and the analyte is subjected to quantitative determination.

In the above embodiment, the biotinylated tyramide and the fluorescent particles having avidin may be previously bound to obtain tyramide to which the fluorescent particles are bound, and this may be brought into contact with the carrier particle on which the complex is immobilized. Alternatively, biotinylated tyramide and fluorescent particles having avidin may be added substantially simultaneously to the carrier particle on which the complex is immobilized.

As a further embodiment, the case where an antigen is detected as an analyte with use of an antibody as a capture substance, HRP as a catalyst, and a multi-substrate obtained by binding a plurality of tyramide molecules to a support having fluorescent substances as a substrate, will be described with reference to the schematic diagram of FIG. 3. In FIG. 3, a carrier particle is represented by a black circle; an antibody is represented by a Y shape; an antigen is represented by a hollow triangle; HRP is represented by a black diamond; a substrate molecule is represented by a white circle; a support is represented by a hollow square; and a radical is represented by an asterisk (*).

When a plurality of carrier particles on each of which a first capture antibody is immobilized, a sample containing an antigen, and a second capture antibody labeled with HRP are mixed with one another (FIG. 3(A)), a complex containing one molecule of antigen and capture antibodies on the carrier particle is formed (FIG. 3(B)). Next, a multi-substrate containing a plurality of tyramides is mixed. The tyramide in the multi-substrate added in an excess amount is successively radicalized by HRP (FIG. 3(C)). In the figure, one molecule of tyramide in the multi-substrate is radicalized, but two or more molecules of tyramide may be radicalized. The multi-substrate is immobilized on a complex containing the HRP and a carrier particle on which the complex is immobilized via the radicalized tyramide. Accordingly, a large number of multi-substrates are immobilized on the carrier particle (carrier particle on the right in FIG. 3(D)). At this time, since radicals react only with substances in the vicinity, a multi-substrate is not immobilized on a carrier particle which does not capture the complex (carrier particle on the left in FIG. 3(D)). Here, a tyramide molecule which does not contribute to immobilization is present in the above complex or the multi-substrate immobilized on the carrier particle. Since tyramide itself is also an aromatic compound, radicalized tyramide contained in another multi-substrate can bind to the tyramide molecule which does not contribute to immobilization. As described above, the multi-substrate tyramide is successively radicalized by HRP. Therefore, another multi-substrate containing radicalized tyramide is further immobilized on the tyramide molecule of the multi-substrate immobilized on the carrier particle. In this way, the multi-substrate can successively bind using as a scaffold the tyramide molecule of another multi-substrate previously immobilized (positive particle in FIG. 3(E)). At this time, since the radicalized tyramide reacts only with substances in the vicinity, the multi-substrate is not immobilized on a carrier particle which does not capture the complex (negative particle in FIG. 3(E)). Thereafter, the carrier particles are passed through a flow cytometer, and the fluorescence intensity of the carrier particles is measured one by one. The number of the positive particles is counted, and the analyte is subjected to quantitative determination.

Unreacted free components may be removed during each step. Generally, this operation separates a molecule (B) immobilized on a solid phase and a free molecule (F) not immobilized on a solid phase, and thus is called B/F separation. For example, after forming a complex on a carrier particle, B/F separation can be performed for the purpose of removing an unreacted second capture substance before mixing with a labeled substrate. Furthermore, after reaction between the labeled substrate and a catalyst, B/F separation can be performed for the purpose of removing an unreacted labeled substrate, before detection of carrier particles. B/F separation can be performed by a method often used in the art. For example, B/F separation can be performed by centrifuging carrier particles and removing the supernatant containing unreacted free components. In the case where carrier particles are magnetized, B/F separation can be performed by collecting the carrier particles by a magnet (hereinafter, also referred to as "magnetism collection") and removing liquid components.

According to the method of the present embodiment, it is also possible to detect two or more kinds of analytes. This is generally referred to as multiplex detection. In the detection step, in order to distinctly detect at least two kinds of analytes from each other, a capture substance capable of specifically binding to each of at least two kinds of analytes is used, as the first capture substance and/or the second capture substance. As an example, a case of detecting two kinds of analytes, a first analyte and a second analyte of a different kind of the first analyte, will be described. In this case, a carrier particle on which a first capture substance that captures a first analyte is immobilized (hereinafter, referred to as "carrier particle A") and a carrier particle on which a third capture substance that captures a second analyte is immobilized (hereinafter, referred to as "carrier particle B") can be used. A second capture substance that captures a first analyte is bound to the first analyte captured by the carrier particle A to form a first complex on the carrier particle A. A fourth capture substance that captures a second analyte is bound to the second analyte captured by the carrier particle B to form a second complex on the carrier particle B. In order to distinctly detect two kinds of analytes from each other, it is preferable in the detection step that a carrier particle that captures one molecule of the first analyte (hereinafter, referred to as "positive particle A") and a carrier particle that captures one molecule of the second analyte (hereinafter, referred to as "positive particle B") generate mutually distinguishable signals. In the case of distinctly detecting the positive particle A and the positive particle B from each other, different kinds of catalysts and/or substrates may be used so that the positive particle A and the positive particle B generate mutually distinguishable signals. Different kinds of labels may also be used. This makes it possible to generate the above mutually distinguishable signals from the reaction product of the catalyst and the substrate. Specifically, in the formation step of the complex, a second capture substance having a first catalyst and a fourth capture substance having a second catalyst different from the first catalyst can be used. Moreover, in the immobilization step, a first substrate corresponding to the first catalyst and a second substrate corresponding to the second catalyst are used as substrates. Here, fluorescent dyes capable of generating mutually distinguishable fluorescence wavelengths may be used as different kinds of labels. For example, the first substrate may have a first fluorescent dye, and the second substrate may have a second fluorescent dye which generates a different fluorescence wavelength to the extent distinguishable from the first fluorescent dye. Accordingly, the first fluorescent dye is immobilized on the carrier particle A that captures one molecule of the first analyte, and the second fluorescent dye is immobilized on the carrier particle B that captures one molecule of the second analyte. Moreover, in the detection step, as signals distinguishable from each other, fluorescence from the first fluorescent dye and that from the second fluorescent dye immobilized on the carrier particle can be detected. The carrier particle A that captures one molecule of the first analyte and the carrier particle B that captures one molecule of the second analyte can be distinctly detected from each other by a difference in fluorescence wavelength. The method of the present embodiment may further include a step of determining which analyte has been detected based on the mutually distinguishable signals.

Fluorescent dyes capable of generating fluorescence with different intensities to the extent mutually distinguishable when irradiated with the same excitation light may be used as different kinds of labels. In this case, since each fluorescent dye can be distinguished from each other by a difference in fluorescence intensity, each fluorescent dye may generate the same or similar fluorescence wavelength. In the above example, the first substrate may have a first fluorescent dye, and the second substrate may have a second fluorescent dye that generates fluorescence of a different intensity to the extent distinguishable from the first fluorescent dye. As signals distinguishable from each other, fluorescence from the first fluorescent dye and that from the second fluorescent dye immobilized on the carrier particle can be detected. The carrier particle A that captures one molecule of the first analyte and the carrier particle B that captures one molecule of the second analyte can be distinctly detected from each other by a difference in fluorescence intensity.

In the present embodiment, it is also possible to detect at least two kinds of analytes by using carrier particles having different average particle sizes. The average particle sizes are preferably different to the extent that each of groups of carrier particles having an average particle size can be distinguished by optical information. Specifically, it is possible to use different kinds of carrier particles having average particle sizes different from each other by 100 nm or more, preferably by 200 nm or more, and more preferably by 500 nm or more. The number of kinds of the carrier particles is preferably the same as the number of kinds of the analytes. For example, in the case of detecting the first analyte and the second analyte, first carrier particles having an average particle size of 500 nm and second carrier particles having an average particle size of 1 μm can be used. Here, it is preferable that a first capture substance that captures the first analyte is immobilized on each of the first carrier particles, and a third capture substance that captures the second analyte is immobilized on each of the second carrier particles. The first carrier particles and the second carrier particles can be distinguished from each other by signals based on the average particle size of the carrier particles. For example, when the first carrier particles and the second carrier particles are irradiated with light, respectively, scattered lights having different intensities are generated from the first carrier particles and the second carrier particles due to the difference in the average particle size. Therefore, based on the scattered light intensity, the first carrier particles and the second carrier particles can be distinctly detected from each other. Then, negative particles and positive particles can be distinguished by detecting the carrier particles on each of which the reaction product is immobilized, in each of the group of the first carrier particles and the group of the second carrier particles that are distinguished from each other.

At least two kinds of analytes can be detected by using carrier particles of mutually different materials. For example, in the case of detecting two kinds of a first analyte and a second analyte, a first carrier particle having magnetism and a second carrier particle having no magnetism can be used. In this case, it is preferable that a first capture substance that captures the first analyte is immobilized on the first carrier particle, and a third capture substance that captures the second analyte is immobilized on the second carrier particle. By separating the first carrier particle and the second carrier particle using a magnet before the detection, the first carrier particle and the second carrier particle can be distinctly detected from each other. Then, negative particles and positive particles can be distinguished by detecting the carrier particles on each of which the reaction product is immobilized, in each of the group of the first carrier particles and the group of the second carrier particles that are separated from each other.

Even when there are three or more kinds of analytes, each of analytes can be detected from one another by the same principle as above.

Carrier particles, a first capture substance, a second capture substance, a catalyst and a labeled substrate can be provided as a reagent kit to carry out the method of the present embodiment. It is preferable that the carrier particles, the first capture substance, the second capture substance, the catalyst and the labeled substrate are each stored in separate containers. The catalyst and the labeled substrate need to be stored in separate containers, but others may be stored in one container. As described above, the catalyst and the second capture substance may be previously bound to each other. The carrier particle and the first capture substance may be previously bound to each other. The substrate may be a labeled substrate containing a support and a plurality of tyramide molecules. The label may be contained in the tyramide molecule or in the support.

Any of the provided reagents is preferably a liquid reagent. As a solvent, water or a buffer solution widely used in the art can be used. For example, a buffer such as phosphate buffer, Tris buffer, triethylamine buffer or MES buffer can be used.

In the present embodiment, a container storing the above-described various reagents may be packed in a box and provided to the user. This box may contain a package insert of the reagent kit. For example, the constitution of the reagent kit, the detection protocol of an analyte and the like are preferably described in this package insert. FIG. 12A shows an example of the reagent kit of the present embodiment. In FIG. 12A, reference numeral 10 denotes a reagent kit, 11 denotes a first container storing carrier particles, 12 denotes a second container storing a first capture substance, 13 denotes a third container storing a second capture substance, 14 denotes a fourth container storing a catalyst, 15 denotes a fifth container storing a labeled substrate, 16 denotes a package insert, and 17 denotes a packing box.

FIG. 12B shows an example of a reagent kit of a further embodiment. In FIG. 12B, reference numeral 20 denotes a reagent kit, 21 denotes a first container storing carrier particles, a first capture substance and a second capture substance, 22 denotes a second container storing a catalyst, 23 denotes a third container storing a labeled substrate, 24 denotes a package insert, and 25 denotes a packing box.

FIG. 12C shows an example of a reagent kit of a further embodiment. In FIG. 12C, reference numeral 30 denotes a reagent kit, 31 denotes a first container storing carrier particles, 32 denotes a second container storing a first capture substance, 33 denotes a third container storing a second capture substance to which a catalyst is previously bound, 34 denotes a fourth container storing a labeled substrate, 35 denotes a package insert, and 36 denotes a packing box.

FIG. 12D shows an example of a reagent kit of a further embodiment. In FIG. 12D, reference numeral 40 denotes a reagent kit, 41 denotes a first container storing carrier particles to each of which a first capture substance is previously bound, 42 denotes a second container storing a second capture substance, 43 denotes a third container storing a catalyst, 44 denotes a fourth container storing a labeled substrate, 45 denotes a package insert, and 46 denotes a packing box.

FIG. 12E shows an example of a reagent kit of a further embodiment. In FIG. 12E, reference numeral 50 denotes a reagent kit, 51 denotes a first container storing carrier particles to each of which a first capture substance is previously bound, 52 denotes a second container storing a second capture substance to which a catalyst is previously bound, 53 denotes a third container storing a labeled substrate, 54 denotes a package insert, and 55 denotes a packing box.

The reagent kit of the present embodiment may contain detection particles, in addition to the carrier particles, the first capture substance, the second capture substance, the catalyst and the substrate. FIG. 17A is an example of the reagent kit of this embodiment. In FIG. 17A, reference numeral 60 denotes a reagent kit, 61 denotes a first container storing carrier particles, 62 denotes a second container storing a first capture substance, 63 denotes a third container storing a second capture substance, 64 denotes a fourth container storing a catalyst, 65 denotes a fifth container storing a substrate, 66 denotes a sixth container storing detection particles, 67 denotes a package insert, and 68 denotes a packing box.

FIG. 17B shows an example of a reagent kit of a further embodiment. In FIG. 17B, reference numeral 70 denotes a reagent kit, 71 denotes a first container storing carrier particles, a first capture substance and a second capture substance, 72 denotes a second container storing a catalyst, 73 denotes a third container storing a substrate, 74 denotes a fourth container storing detection particles, 75 denotes a package insert, and 76 denotes a packing box.

FIG. 17C shows an example of a reagent kit of a further embodiment. In FIG. 17C, reference numeral 80 denotes a reagent kit, 81 denotes a first container storing carrier particles, 82 denotes a second container storing a first capture substance, 83 denotes a third container storing a second capture substance to which a catalyst is previously bound, 84 denotes a fourth container storing a substrate, 85 denotes a fifth container storing detection particles, 86 denotes a package insert, and 87 denotes a packing box.

FIG. 17D shows an example of a reagent kit of a further embodiment. In FIG. 17D, reference numeral 90 denotes a reagent kit, 91 denotes a first container storing carrier particles to each of which a first capture substance is previously bound, 92 denotes a second container storing a second capture substance, 93 denotes a third container storing a catalyst, 94 denotes a fourth container storing a substrate, 95 denotes a fifth container storing detection particles, 96 denotes a package insert, and 97 denotes a packing box.

FIG. 17E shows an example of a reagent kit of a further embodiment. In FIG. 17E, reference numeral 100 denotes a reagent kit, 101 denotes a first container storing carrier particles to each of which a first capture substance is previously bound, 102 denotes a second container storing a second capture substance to which a catalyst is previously bound, 103 denotes a third container storing a substrate, 104 denotes a fourth container storing detection particles, 105 denotes a package insert, and 106 denotes a packing box.

The reagent kit of the present embodiment may be provided as a reagent kit for performing the multiplex detection described above. For example, a reagent kit for detecting a first analyte and a second analyte may contain carrier particles, a first capture substance, a second capture substance, a third capture substance, a fourth capture substance, a catalyst, and a labeled substrate. As described above, the catalyst and the labeled substrate may be a combination capable of generating mutually distinguishable signals. For example, the reagent kit may contain a first catalyst and a first labeled substrate corresponding to the first catalyst, and a second catalyst and a second labeled substrate corresponding to the second catalyst. The first labeled substrate and the second labeled substrate may have a fluorescent dye capable of generating fluorescence wavelength or intensity mutually distinguishable as a label. Each reagent may be stored in separate containers. The first catalyst and the second capture substance may be previously bound to each other, and the second catalyst and the fourth capture substance may be previously bound to each other. The reagent kit may contain first carrier particles and second carrier particles having a different average particle size to the extent distinguishable from the first carrier particles. The reagent kit may contain first carrier particles having magnetism and second carrier particles not having magnetism. The first carrier particle and the first capture substance may be previously bound to each other, and the second carrier particle and the third capture substance may be previously bound to each other. In the case where the capture substance is bound to the carrier particle in use, it is preferable that the first carrier particles and the second carrier particles are stored in separate containers.

The present invention includes use of the reagent kit described above for the detection of an analyte. The detection of an analyte is as described above. The present invention also includes use for producing a reagent kit of the above-described various reagents. The various reagents and reagent kit are as described above.

EXAMPLES

Hereinafter, the present embodiment will be described with reference to examples. The particle sizes referred to in the examples are all the above-described average particle sizes.

(Example 1) Detection of Carrier Particles by Flow Cytometer (1) Preparation of Magnetic Particles As magnetic particles, magnetic particles having an average particle size of 200 nm (FG beads COOH beads, manufactured by Tamagawa seiki Co., Ltd), magnetic particles having an average particle size of 500 nm (SiMAG-COOH, manufactured by Chemicell GmbH), magnetic particles having an average particle size of 2 μm (micromer M-COOH, manufactured by micromod Partikeltechnologie GmbH) and magnetic particles having an average particle size of 4 μm (micromer M-COOH, manufactured by micromod Partikeltechnologie GmbH) were prepared. A solution (200 μL) prepared by mixing a 200 mM N-hydroxysuccinimide (NHS, manufactured by KISHIDA CHEMICAL Co., Ltd.) solution and a water-soluble carbodiimide (WSC, manufactured by DOJINDO LABORATORIES) solution at 1:1 (NHS/WSC mixed solution) was prepared. Each of $10^6$ to $10^8$ magnetic particles was added to the NHS/WSC mixed solution, and the mixture was caused to react at room temperature for 2 hours. After magnetism collection, the supernatant was removed. A phosphate buffer solution (500 μL) (hereinafter, also referred to as PBS) (pH 6.0) was added to the magnetic particles, and the mixture was stirred with a vortex mixer. The operation of magnetism collection, removal of the supernatant, addition of the phosphate buffer and stirring was further performed four times. After magnetism collection, 800 µL of a solution of 0.1 mM biotin-bound BSA (manufactured by Sysmex Corporation) was added, and the mixture was caused to react in a shaking thermostat (Shaking Incubator SI-300C, manufactured by AS ONE Corporation) set at 1600 rpm and 25° C. for 1 hour. The particle suspension was taken out from the shaking thermostat, and after magnetism collection, the supernatant was removed, 500 µL of PBS (pH 7.5) was added, and the mixture was stirred with a vortex mixer. In this way, a particle suspension containing magnetic particles on each of which biotin was immobilized was obtained.

(2) Immobilization of HRP on Magnetic Particles

HRP to which streptavidin was bound (Streptavidin Poly-HRP 80 Conjugate, manufactured by Stereospecific Detection Technologies) was diluted with PBS (pH 7.4) to prepare each of HRP solutions at concentrations of 0 pg/mL, 10 pg/mL, and 100 pg/mL. Each of the HRP solutions (20 µL) was added to 80 µL of each of the particle suspensions prepared in the above (1). The mixture was caused to react in a thermostat set at 1600 rpm and 25° C. for 1 hour. The particle suspension was taken out from the shaking thermostat, and after magnetism collection, the supernatant was removed, 80 µL of PBS (pH 7.4) was added, and the mixture was stirred with a vortex mixer. The magnetism collection, removal of the supernatant, PBS addition and stirring were performed one more time.

(3) Enzymatic Reaction

30% $H_2O_2$ of TSA kit #22 with HRP, Streptavidin and Alexa Fluor 488 tyramide (product number T20932, manufactured by Life Technologies) was diluted with an Amplification buffer to prepare a 0.005% substrate buffer. Tyramide-Alexa Fluor 488 was diluted 20-fold with the substrate buffer. The diluted Tyramide-Alexa Fluor 488 (20 µL each) was added to the particle suspension prepared in the above (2) to disperse the magnetic particles. An enzymatic reaction was carried out in a shaking thermostat set at 1000 rpm and 25° C. for 30 minutes. After magnetism collection, the supernatant was removed. Thereto was added 80 µL of PBS (pH 7.4), and the mixture was stirred with a vortex mixer. The magnetism collection, removal of the supernatant, PBS addition and stirring were performed one more time. After magnetism collection, the supernatant was removed. Thereto was added 500 µL of PBS (pH 7.4), and the mixture was stirred with a vortex mixer.

(4) Detection by Flow Cytometer

The particle suspension obtained in (3) was caused to flow to FACS VERSE (manufactured by Becton Dickinson), and the fluorescence intensity of each carrier particle was measured. Here, the maximum fluorescence intensity when measuring only negative particles was used as a threshold value, and magnetic particles each having a fluorescence intensity equal to or greater than this threshold value were counted as positive particles. The total number of magnetic particles (negative particles) and positive particles each having a fluorescence intensity less than this threshold value was counted as all particles. The number of all particles represents the total number of magnetic particles subjected to detection.

(5) Results

The correlation between the HRP concentration and the number of positive particles is shown in Table 2. The value of the number of positive particles shown in Table 2 is a value obtained by multiplying the proportion of positive particles to all particles subjected to detection by the number of magnetic particles ($10^6$ to $10^8$) added in the above (1). The proportion (%) of positive particles was calculated as [(number of positive particles counted by flow cytometer)/(number of all particles counted by flow cytometer)]×100.

TABLE 2

| Particle size | HRP concentration (pg/mL) | Number of positive particles |
|---|---|---|
| 200 nm | 0 | 0 |
|  | 10 | 32,400 |
|  | 100 | 370,800 |
| 500 nm | 0 | 160 |
|  | 10 | 5,140 |
|  | 100 | 98,200 |
| 2 µm | 0 | 60 |
|  | 10 | 9,564 |
|  | 100 | 49,080 |
| 4 µm | 0 | 200 |
|  | 10 | 280 |
|  | 100 | 340 |

As shown in Table 2, it was found that one molecule detection is possible using carrier particles having any particle size of 200 nm, 500 nm, 2 µm and 4 µm. As the particle size of the carrier particle became smaller, a large number of positive particles could be detected.

(Example 2) Detection of Carrier Particles by Microscope (1) Preparation of Magnetic Particle on which Antibody is Immobilized As magnetic particles, magnetic particles having an average particle size of 1 µm (Dynabeads Myone-COOH, manufactured by Life Technologies), magnetic particles having an average particle size of 2 µm (micromer M-COOH, manufactured by micromod Partikeltechnologie GmbH) and magnetic particles having an average particle size of 4 µm (micromer M-COOH, manufactured by micromod Partikeltechnologie GmbH) were prepared. An antibody binding to an HBs antigen (manufactured by Sysmex Corporation) (hereinafter, also referred to as an "anti-HBs antibody") was immobilized on each of 1 µm magnetic particles, using Dynabeads Antibody-Coupling kit (manufactured by Life Technologies) according to the attached instruction, to obtain a particle suspension. Similarly, an anti-HBs antibody was immobilized on each of 2 µm magnetic particles and each of 4 µm magnetic particles to obtain particle suspensions. The number of magnetic particles used here was $10^6$, respectively.

(2) Capture of HBs Antigen

The particle suspension prepared in the above (1) was magnetically collected, and the supernatant was removed. Thereto was added 80 µL of PBS (pH 7.4) to disperse the magnetic particles. Thereto was added 20 µL of CO (0 IU/mL) or C1 (0.25 IU/mL) of HISCL (registered trademark) HBsAg calibrator (manufactured by Sysmex Corporation). Antigen-antibody reaction was carried out in a shaking thermostat set at 1600 rpm and 42° C. for 40 minutes. The particle suspension was taken out from the shaking thermostat, and after magnetism collection, the supernatant was removed. Thereto was added 80 µL of PBS (pH 7.4), and the mixture was stirred with a vortex mixer. The operation of magnetism collection, removal of the supernatant, PBS addition and stirring was performed one more time.

(3) Binding of Second Capture Antibody

After magnetism collection, the supernatant was removed. Thereto was added 100 μL of a 1 μg/mL biotinylated anti-HBs antibody (manufactured by Sysmex Corporation) solution to disperse the magnetic particles. The epitope of this second capture antibody is different from the epitope of the first capture antibody. Antigen-antibody reaction was carried out in a shaking thermostat set at 1600 rpm and 42° C. for 20 minutes. The particle suspension was taken out from the shaking thermostat, and after magnetism collection, the supernatant was removed. Thereto was added 80 μL of PBS (pH 7.4), and the mixture was stirred with a vortex mixer. The operation of magnetism collection, removal of the supernatant, PBS addition and stirring was performed one more time.

(4) Binding of HRP

After magnetism collection, the supernatant was removed. Thereto was added 100 μL of 1 μg/mL Streptavidin Poly-HRP 80 Conjugate to disperse the magnetic particles. The mixture was caused to react in a shaking thermostat set at 1600 rpm and 25° C. for 10 minutes. The particle suspension was taken out from the shaking thermostat, and after magnetism collection, the supernatant was removed. Thereto was added 80 μL of PBS (pH 7.4), and the mixture was stirred with a vortex mixer. The operation of magnetism collection, removal of the supernatant, PBS addition and stirring was performed one more time.

(5) Enzymatic Reaction

The enzymatic reaction was carried out in the same manner as in Example 1 (3) except that 20 μL of PBS was finally added, and the mixture was stirred with a vortex mixer.

(6) Detection by Microscope

The particle suspension (10 μL) was collected and dropped onto a microscopic slide glass for sedimentation (manufactured by Matsunami Glass Ind., Ltd.). Using a fluorescence microscope (BZX710, manufactured by KEYENCE CORPORATION) equipped with an excitation filter and a fluorescence filter of a wavelength appropriate to detect Alexa Fluor 488 as a fluorescent substance, a bright field image and a fluorescence image were imaged using a 40× objective lens. The exposure time for fluorescence image acquisition was set to 1/5 seconds. The acquired images were analyzed using image analysis software ImageJ. As the number of fluorescent positive particles in the image, the bright spots higher than the maximum fluorescence brightness of negative particles in the fluorescence image were counted. In addition, signals in the image were binarized by the threshold of ImageJ in the bright field image, and the number of all magnetic particles in the image was counted with Particle tool.

(7) Results

FIG. 4 shows the correlation between the average particle size and the number of positive particles. The vertical axis of the line graph in FIG. 4 is the proportion of positive particles to the number of all particles. The proportion (%) of positive particles to the number of all particles was calculated as [(number of positive particles counted by fluorescence microscope)/(number of all particles counted by fluorescence microscope)]×100. As shown in FIG. 4, a large number of positive particles could be detected by using magnetic particles having a smaller average particle size.

(Example 3) Correlation Between Analyte Concentration and Number of Positive Particles (1) Preparation of Magnetic Particle on which Antibody is Immobilized A suspension of magnetic particles on each of which an anti-HBs antibody was immobilized was prepared in the same manner as in Example 2 (1), except for using $1.4 \times 10^6$ magnetic particles (Dynabeads Antibody-Coupling Kit, manufactured by Life Technologies) having an average particle size of 2.8 μm, in place of the magnetic particles described in Example 2 (1).

(2) Capture of HBs Antigen

The particle suspension prepared in the above (1) was magnetically collected, and the supernatant was removed. Thereto was added 80 μL of HISCL (registered trademark) HBsAg R1 reagent (manufactured by Sysmex Corporation) to disperse the magnetic particles. Thereto was added 20 μL of any of CO (0 IU/mL), C1 (0.25 IU/mL), C2 (2.5 IU/mL) of HISCL (registered trademark) HBsAg calibrator (manufactured by Sysmex Corporation), an antigen solution obtained by diluting C1 10-fold (0.025 IU/mL) with a HISCL (registered trademark) specimen diluent, and an antigen solution obtained by diluting C1 100-fold (0.0025 IU/mL) with a HISCL (registered trademark) specimen diluent, and the mixture was incubated at 42° C. for 40 minutes. The resulting solution was magnetically collected, and the supernatant was removed, then 100 μL of a HISCL (registered trademark) washing solution (manufactured by Sysmex Corporation) was added to disperse the magnetic particles. The operation of magnetism collection, removal of the supernatant, washing solution addition and dispersion was performed one more time.

(3) Binding of Second Capture Antibody

After magnetism collection, the supernatant was removed. Thereto was added 100 μL of a second capture antibody solution prepared by diluting 1 mg/mL biotinylated anti-HBs antibody (manufactured by Sysmex Corporation) 1000-fold with a diluent for HISCL (registered trademark) HBsAg R3 reagent (manufactured by Sysmex Corporation). The epitope of this second capture antibody is different from the epitope of the first capture antibody. The magnetic particles were dispersed and caused to react at 42° C. for 20 minutes. The resulting solution was magnetically collected, and the supernatant was removed, then 100 μL of a HISCL (registered trademark) washing solution (manufactured by Sysmex Corporation) was added to disperse the magnetic particles. The operation of magnetism collection, removal of the supernatant, washing solution addition and dispersion was performed one more time.

(4) Binding of HRP

After magnetism collection, the supernatant was removed. Thereto was added 100 μL of Pierce Streptavidin Poly-HRP (manufactured by Thermo Scientific) diluted 1000-fold with PBS (pH 7.4). The magnetic particles were dispersed and caused to react at 25° C. for 10 minutes. The resulting solution was magnetically collected, and the supernatant was removed, then 100 μL of a HISCL (registered trademark) washing solution (manufactured by Sysmex Corporation) was added to disperse the magnetic particles. The operation of magnetism collection, removal of the supernatant, washing solution addition and dispersion was performed two more times.

(5) Enzymatic Reaction

30% $H_2O_2$ of TSA kit #22 with HRP, Streptavidin and Alexa Fluor 488 tyramide (product number T20932, manufactured by Life Technologies) was diluted with an Amplification buffer to prepare a 0.005% substrate buffer. Tyramide-Alexa Fluor 488 was diluted 20-fold with the substrate buffer. The diluted Tyramide-Alexa Fluor 488 (10 μL) was added to the particle suspension prepared in the above (4) to disperse the magnetic particles. An enzymatic reaction was carried out at 25° C. for 30 minutes. After magnetism collection, the supernatant was removed. Thereto was added 100 μL of a HISCL (registered trademark) washing solution (manufactured by Sysmex Corporation) to disperse the magnetic particles. The operation of magnetism collection, removal of the supernatant, washing solution addition and dispersion was performed one more time. Thereto was added 10 μL of PBS (pH 7.4) to disperse the magnetic particles.

(6) Detection by Microscope

The particle suspension (10 μL) was collected and dropped onto a microscopic slide glass for sedimentation (manufactured by Matsunami Glass Ind., Ltd.). Using a fluorescence microscope (BZX710, manufactured by KEYENCE CORPORATION) equipped with an excitation filter and a fluorescence filter of a wavelength appropriate to detect Alexa Fluor 488 as a fluorescent substance, a bright field image and a fluorescence image were imaged using a 40× objective lens. The exposure time for fluorescence image acquisition was set to ⅕ seconds. The acquired images were analyzed using image analysis software ImageJ. As the number of fluorescent positive particles in the image, the bright spots higher than the maximum fluorescence brightness of negative particles in the fluorescence image were counted. In addition, signals in the image were binarized by the threshold of ImageJ in the bright field image, and the number of all magnetic particles in the image was counted with Particle tool.

(7) Results

FIG. 5 shows the taken images. Almost all magnetic particles were negative at 0 IU/mL. On the other hand, bright spots were observed in samples containing an HBs antigen. FIG. 6 shows an enlarged view of the image taken at the detection of an HBs antigen concentration of 0.25 IU/mL. Since the magnetic particles themselves have autofluorescence, constant fluorescence is observed even for negative particles, but as indicated by the arrow, a part of the particle surface is strongly labeled in positive particles. Thus, when a fluorescence microscope was used, positive particles and negative particles could be clearly distinguished from each other. Moreover, as is clear from FIG. 5, the higher the concentration of HBs antigen was, the greater the number of bright spots was. It was suggested that the HBs antigen concentration could be subjected to quantitative determination by this method.

Example 4

In the same manner as in Example 3 (1) to (4), a suspension of magnetic particles on each of which a complex was formed was obtained. The enzymatic reaction was carried out in the same manner as in Example 3 (5), except that 5 μL of PBS (pH 7.4) was finally added to this particle suspension to disperse the magnetic particles. All particles and positive particles were counted in the same manner as in Example 3 (6).

Comparative Example 1

(1) Fabrication of Array

A cover glass (Neo cover glass 24×32 No. 1, manufactured by Matsunami Glass Ind., Ltd.) was immersed in 10 N KOH overnight. Thereafter, the cover glass was immersed and washed 10 times with deionized water. After drying on a hot plate at 180° C., the cover glass was allowed to stand at room temperature, and the temperature of the cover glass was returned to room temperature. Approximately 70 μL of CYTOP (registered trademark) (CTL-809, manufactured by ASAHI GLASS CO., LTD.) was dropped onto the cover glass and spin-coated with the following program A using a spin coater (MS-A100, manufactured by MIKASA CO., LTD.).

<Program A>
Slope 5 seconds
500 rpm 10 seconds
Slope 5 seconds
2000 rpm 30 seconds
Slope 5 seconds
END The cover glass was further heated on a hot plate at 180° C. for 1 hour. The operation of dropping of CYTOP (registered trademark), spin coating and heating were repeated three more times to form a CYTOP (registered trademark) layer having a thickness of about 4 μm on the cover glass. Photolithography was performed for forming fine wells having a diameter of several μm (hereinafter, also referred to as "microwells") in this layer. A positive type photoresist (AZ-4903, manufactured by AZ Electronic Materials) was dropped onto the CYTOP (registered trademark) layer and spin-coated with the following program B.

<Program B>
Slope 5 seconds
500 rpm 10 seconds
Slope 5 seconds
4000 rpm 60 seconds
Slope 5 seconds
END The resist remained on the edge of the cover glass was wiped off with gauze containing 100% ethanol. After baking at 55° C. for 3 minutes, the cover glass was baked at 110° C. for 5 minutes. A photomask was washed with acetone, and the resultant was set in a mask aligner (manufactured by SAN-EI ELECTRIC CO., LTD.). The cover glass coated with the photoresist was set on a sample stand of the mask aligner, the glass and the photomask were brought into contact with each other, and UV light was irradiated at a power of 256 for 35 seconds. Thereafter, the resultant was immersed in a developing solution (AZ Developer, manufactured by AZ Electronic Materials) for 5 minutes and developed. Thereafter, the resultant was rinsed with ultrapure water (MilliQ (registered trademark)). $O_2$ Plasma etching was performed using a reactive ion etching system (RIE-10NR, manufactured by SAMCO Inc.) under the following process conditions.

<Process Conditions>
O2 50 sccm, Pressure 10 Pa, Power 50 W, Time 30 minutes

Through this step, CYTOP (registered trademark) not laminated with resist was dry etched, and fine openings were formed on the cover glass substrate. The etched glass was immersed in acetone, and ultrasonic treatment was performed for 15 minutes. Subsequently, the liquid was replaced with ethanol, and ultrasonic treatment was performed for 15 minutes. Further, the liquid was replaced with ultrapure water, and ultrasonic treatment was performed for 15 minutes. Thus, a CYTOP (registered trademark) substrate having a plurality of microwells formed on the cover glass was prepared. Each microwell had a cylindrical shape with a diameter of about 5 μm and a depth of about 4 μm in diameter, and the distance between the centers of two adjacent microwells was about 10 µm.

(2) Fabrication of Top Glass

Quartz having a thickness of 3 mm on which a through hole having a diameter of 1 mm was formed was prepared. Approximately 70 µL of CYTOP (registered trademark) was dropped onto one side of the quartz and spin-coated with the above program A. The quartz was baked at 180° C. for 1 hour on a hot plate. This provided a top glass having a CYTOP (registered trademark) layer with a thickness of about 2 µm.

(3) Fabrication of Array

A double-sided tape having a thickness of 60 µm (No. 5606, manufactured by Nitto Denko Corporation) was stuck on the CYTOP (registered trademark) layer side of the CYTOP (registered trademark) substrate prepared in the above (1) to prepare an array. The double-sided tape was stuck in the "U" shape at the portion where the microwell was not formed. The CYTOP (registered trademark) substrate and the top glass were attached such that the side on which the CYTOP (registered trademark) layer was formed was on the CYTOP (registered trademark) substrate side. This formed a space between the CYTOP (registered trademark) substrate and the top glass. Upon the attachment, the through hole on the top glass was adjusted so as to be located between the portion where the microwell was formed and the portion where the double-sided tape was stuck. The microwell existed between the through hole and the "U" shaped opening, and thus it was configured such that a fluid introduced from the through hole passed through the region where the microwell was formed, and reached the "U" shaped opening.

(4) Detection

In the same manner as in Example 3 (1) to (4), a suspension of magnetic particles on each of which a complex was formed was obtained. QuantaRed Enhanced Chemifluorescent HRP Substrate kit (Catalog #15159, manufactured by Thermo Scientific) was used as a labeled substrate. The particle suspension was magnetically collected, and the supernatant was removed. Thereto was added 30 µL of a substrate solution in which QuantaRed ADHP Concentrate, QutantaRed Stable Peroxide Solution, and QutantaRed Enhanced Solution were mixed at 1:50:50. After the reaction, 30 µL of the particle suspension was introduced from the through hole into the array. On the ice-cold tube rack (IR-1, manufactured by TOWA LABO Corporation), the array into which the sample had been introduced was allowed to stand for 5 minutes, and degassing treatment was performed. Thereafter, 70 µL of a hydrophobic solvent (FC-40, manufactured by Sigma-Aldrich) was introduced into the array from the through hole. This formed microdroplets in the microwells of the array. The suspension and hydrophobic solvent leaking from the array were removed with Kimwipe each time. The array was shielded with aluminum foil and allowed to stand for 5 minutes in a thermostat (Shaking Incubator SI-300C, manufactured by AS ONE Corporation) set at 42° C. Using a fluorescence microscope (BZX710, manufactured by KEYENCE CORPORATION) equipped with an excitation filter and a fluorescence filter of a wavelength appropriate to detect QuantaRed, a bright field image and a fluorescence image were imaged using a 40× objective lens. The exposure time for fluorescent image acquisition was 1/11 seconds. The acquired images were analyzed by image analysis software ImageJ. The bright spots higher than the maximum fluorescence brightness of negative wells in which particles were enclosed in the fluorescence image were counted as positive wells. In addition, signals in the image were binarized by the threshold of ImageJ in the bright field image, and the number of all particles enclosed in the microwell was counted with Particle tool.

FIG. 7 shows the result of Example 4, and FIG. 8 shows the result of Comparative Example 1. FIG. 7 shows the correlation between the HBs antigen concentration and the proportion (%) of the number of positive particles to the number of all particles. The proportion (%) of positive particles to the number of all particles was calculated as (number of positive particles counted by fluorescence microscope)/(number of all particles counted by fluorescence microscope)×100. FIG. 8 shows the correlation between the HBs antigen concentration and the proportion (%) of the number of positive wells to the number of all particles enclosed in the microwell. The proportion (%) of the number of positive wells to the number of all particles enclosed in the microwell was calculated as (number of positive wells)/(number of all particles enclosed in microwell)×100. In both methods, the proportion of positive particles or positive wells increased with an increase in the HBs antigen concentration.

(Example 5) Detection of Carrier Particle to which HRP Polymer is Bound (1) Preparation and Detection of Magnetic Bead to which HRP Polymer is Bound The surface of each of biotinylated magnetic particles (average particle size 2.8 µm, manufactured by Sysmex Corporation) was blocked with a blocking buffer (1×PBS/1% Casein) for 2 hours, and then the biotinylated magnetic particles were dispersed in a dilution buffer (1×PBS/1% Casein/0.1% Tween 20). HRP polymers to each of which streptavidin was bound (SA-HRP polymers 50, 100, 200 and 400-mers, manufactured by Stereospecific Detection Technologies) were diluted using a dilution buffer at a concentration of 5.4 fM, and each solution and $1.5 \times 10^6$ biotinylated magnetic particles were caused to react at room temperature for 1.5 hours while stirring at 1600 rpm. As a control, the biotinylated magnetic particles were stirred with a dilution buffer (hereinafter, also referred to as "blank magnetic particles"). The biotinylated magnetic particles after the reaction were washed with a washing buffer (1×PBS/0.1% Tween 20). After washing, the biotinylated magnetic particles and 5 µM of Alexa 488 labeled tyramide (manufactured by Life Technologies) were caused to react in 20 µL of an Amplification buffer containing 0.005% hydrogen peroxide (manufactured by Life Technologies) at room temperature for 30 minutes while stirring at 1600 rpm. After washing the reacted biotinylated magnetic particles with a washing buffer, the particles were dispersed in 200 µL of a sheath liquid (FACS Flow, manufactured by Becton Dickinson), and the intensities of fluorescence and scattered light of each particle were measured using a flow cytometer (FACS Verse, manufactured by Becton Dickinson) at a Low mode flow rate, then the particles was counted. A wavelength of 488 nm was used for excitation light, and a wavelength of 527/32 nm was used for fluorescence filter.

(2) Results

FIGS. 9A and 9B show the results of measuring blank magnetic particles, and magnetic particles to each of which SA-HRP polymer 400-mer was bound by FCM. In FIGS. 9A and 9B, the horizontal axis represents fluorescence intensity, and the vertical axis represents lateral scattered light intensity (size of particles). The mean fluorescence intensity of the blank magnetic particles+5 SD was used as a threshold value. This threshold value is shown by dotted lines in FIGS. 9A and 9B, and particles having higher fluorescence intensity than the threshold value are used as positive particles, and the remaining particles are used as negative particles. When comparing FIGS. 9A and 9B, a clear increase in the number of positive particles was observed in the magnetic particles to each of which SA-HRP polymer 400-mer was bound. Therefore, it was shown that detection of a target molecule by FCM is possible. FIG. 9C shows the result of plotting the relationship between the mean fluorescence intensity value of the top 100 fluorescence intensities among the positive particles and the degree of polymerization of the HRP polymer, for the blank magnetic particles and the magnetic particles to which SA-HRP polymers each having various degrees of polymerization were bound. As shown in FIG. 9C, it was found that as the degree of polymerization increases, the fluorescence intensity of the positive particles also increases, and the rate of change is almost 1. It was found that the accumulation amount of fluorescence-labeled tyramide on the particle increases in proportion to the degree of polymerization of the HRP polymer. FIG. 9D shows the result of plotting the relationship between the proportion of positive particles and the degree of polymerization of the HRP polymer. The proportion (%) of positive particles was calculated as [(number of positive particles counted by flow cytometer)/(number of all particles counted by flow cytometer)]×100. As shown in FIG. 9D, it was found that as the degree of polymerization increases, the number of positive particles also increases. From the above results, it was suggested that, by using a polymer to which a plurality of HRPs is bound as a catalyst, digital detection not requiring compartmentalization by FCM can be realized.

(Example 6) Detection of Analyte Using Fluorescent Substance Containing Aromatic π Conjugated Polymer Structure (1) Preparation of Magnetic Particle on which Antibody is Immobilized An antibody binding to an HBs antigen (manufactured by Sysmex Corporation) (hereinafter, also referred to as an "anti-HBs antibody") was immobilized on each of magnetic particles having a diameter of 2.8 μm, using Dynabeads Antibody-Coupling kit (manufactured by Life Technologies) according to the attached instruction, to obtain a particle suspension.

(2) Capture of HBs Antigen

The magnetic particles in the particle suspension prepared in the above (1) were magnetically collected, and the supernatant was removed. To the magnetic particles was added 80 μL of a diluent (0.1 M MES, 0.15 M NaCl, 0.1% BSA, pH 6.5) to disperse the magnetic particles. The number of the magnetic particles used was $10^6$. To the resulting particle suspension was added 20 μL of any of antigen solutions of 0.1 IU/mL, 0.033 IU/L, 0.011 IU/mL, 0.004 IU/mL and 0.001 IU/mL prepared by diluting C1 (0.25 IU/mL) of HISCL (registered trademark) HBsAg calibrator (manufactured by Sysmex Corporation) with a diluent (0.1 M MES, 0.15 M NaCl, 0.1% BSA, pH 6.5), and the mixture was caused to react in a shaking thermostat set at 1600 rpm and 25° C. for 2 hours. The particle suspension was taken out from the shaking thermostat, the magnetic particles were magnetically collected, and the supernatant was removed. Thereto was added 200 μL of a HISCL (registered trademark) washing solution (manufactured by Sysmex Corporation), and the mixture was stirred with a vortex mixer. The operation of magnetism collection, removal of the supernatant, HISCL washing solution addition and stirring was performed one more time.

(3) Binding of Second Capture Antibody

The magnetic particles in the particle suspension obtained in the above (2) were magnetically collected, and the supernatant was removed. To the magnetic particles was added 100 μL of a second capture antibody solution prepared by diluting 1 mg/mL biotinylated anti-HBs antibody (manufactured by Sysmex Corporation) 5000-fold with a diluent for HISCL (registered trademark) HBsAg R3 reagent (manufactured by Sysmex Corporation). The epitope of this second capture antibody is different from the epitope of the first capture antibody. The magnetic particles were dispersed and caused to react in a shaking thermostat set at 1600 rpm at 25° C. for 45 minutes. The magnetic particles were magnetically collected, and the supernatant was removed, then 200 μL of a HISCL (registered trademark) washing solution (manufactured by Sysmex Corporation) was added to disperse the magnetic particles. The operation of magnetism collection, removal of the supernatant, washing solution addition and dispersion was performed one more time.

(4) Binding of HRP Monomer

The magnetic particles in the particle suspension obtained in the above (3) were magnetically collected, and the supernatant was removed. To the magnetic particles was added 100 μL of 50 pM Streptavidin-HRP monomeric (SDT) diluted with 1% BSA/0.1% Tween 20/PBS (pH 7.4). The magnetic particles were dispersed and caused to react in a shaking thermostat set at 1600 rpm at 25° C. for 1 hour. The magnetic particles were magnetically collected, and the supernatant was removed, then 200 μL of a HISCL (registered trademark) washing solution (manufactured by Sysmex Corporation) was added to disperse the magnetic particles. The operation of magnetism collection, removal of the supernatant, washing solution addition and dispersion was performed two more times.

(5) Enzymatic Reaction

The magnetic particles in the particle suspension obtained in the above (4) were magnetically collected, and the supernatant was removed. To the magnetic particles was added 50 μL each of solutions prepared by diluting a Biotin Amplification Reagent solution of TSA Plus Biotin Kit (product number NEL749B001KT, manufactured by Perkin Elmer) 20-fold with 1× Plus Amplification Diluent to disperse the magnetic particles. An enzymatic reaction was carried out in a shaking thermostat set at 1600 rpm and 25° C. for 30 minutes. The magnetic particles were magnetically collected, and the supernatant was removed. To the magnetic particles was added 200 μL of a HISCL (registered trademark) washing solution (manufactured by Sysmex Corporation) to disperse the magnetic particles. The operation of magnetism collection, removal of the supernatant, washing solution addition and dispersion was performed one more time.

(6) Fluorescent Label

The magnetic particles in the particle suspension obtained in the above (5) were magnetically collected, and the supernatant was removed. To the magnetic particles was added 20 μL each of a Brilliant Violet (trademark) 421 Streptavidin (manufactured by BioLegend, Inc.) solution diluted 20-fold with 1% BSA/0.1% Tween 20/PBS (pH 7.4) to disperse magnetic particles. The mixture was caused to react in a shaking thermostat set at 1300 rpm and 25° C. for 30 minutes. The magnetic particles were magnetically collected, and the supernatant was removed. To the magnetic particles was added 200 μL of a HISCL (registered trademark) washing solution (manufactured by Sysmex Corporation) to disperse the magnetic particles. The operation of magnetism collection, removal of the supernatant, washing solution addition and dispersion was performed one more time. The magnetic particles were magnetically collected, the supernatant was removed, and 10 µL of 0.1% Tween/PBS (pH 7.4) was added.

(7.1) Detection by Flow Cytometer

The particle suspension obtained in the above (6) was dispensed in an amount of 5 µL, and 200 µL of PBS (pH 7.4) was added to disperse the magnetic particles. The resulting particle suspension was passed through a flow cytometer (FACS Verse, manufactured by Becton Dickinson), and the fluorescence intensity of each magnetic particle was measured. A wavelength of 408 nm was used for excitation light, and a filter for BD Horizon V450 was used for the detector optical filter. Here, the maximum fluorescence intensity +5SD when measuring only negative particles was used as a threshold value, and magnetic particles each having a fluorescence intensity equal to or greater than this threshold value were counted as positive particles. The total number of magnetic particles (negative particles) and positive particles each having a fluorescence intensity less than this threshold value was counted as all particles. The number of all particles represents the total number of magnetic particles subjected to detection.

(7.2) Detection by Fluorescence Microscope

The particle suspension obtained in the above (6) was taken out in an amount of 5 µL, and dropped onto a microscopic slide glass for sedimentation (manufactured by Matsunami Glass Ind., Ltd.). Using a fluorescence microscope (BZ-X710, manufactured by KEYENCE CORPORATION) equipped with an excitation filter and a fluorescence filter of a wavelength appropriate to detect a fluorescent substance Brilliant Violet (trademark) 421, a bright field image and a fluorescence image were acquired using a 20× objective lens. The exposure time for fluorescent image acquisition was set to 200 milliseconds.

(8) Results

FIG. 10 shows the fluorescence microscopic images of magnetic particles fluorescence-labeled using Brilliant Violet (trademark) 421. As shown in FIG. 10, the number of bright spots increased in an HBs antigen concentration-dependent manner. FIG. 11 shows the measurement result by the flow cytometer. The proportion (%) of positive particles was calculated as [(number of positive particles counted by flow cytometer)/(number of all particles counted by flow cytometer)]×100. As shown in FIG. 11, it was confirmed that the proportion of the positive particles increases in an antigen concentration-dependent manner.

(Example 7) Investigation of Carrier Particle Concentration (1) Preparation of Magnetic Particle on which Antibody is Immobilized An anti-HBs antibody (manufactured by Sysmex Corporation) was immobilized on each of magnetic particles having a diameter of 2.8 µm, using Dynabeads Antibody-Coupling kit (manufactured by Life Technologies) according to the attached instruction, to obtain a particle suspension.

(2) Capture of HBs Antigen

The magnetic particles in the particle suspension prepared in the above (1) were magnetically collected, and the supernatant was removed. To the magnetic particles was added 80 µL of a diluent for HISCL (registered trademark) HBsAg R1 reagent (manufactured by Sysmex Corporation) to disperse the magnetic particles. The number of the magnetic particles was $5 \times 10^6$. To the resulting particle suspension was added 20 µL of C1 (0.25 IU/mL) of HISCL (registered trademark) HBsAg calibrator (manufactured by Sysmex Corporation), and the mixture was caused to react in a shaking thermostat set at 1600 rpm at 25° C. for 2 hours. The particle suspension was taken out from the shaking thermostat, the magnetic particles were magnetically collected, and the supernatant was removed. Thereto was added 200 µL of a HISCL (registered trademark) washing solution (manufactured by Sysmex Corporation), and the mixture was stirred with a vortex mixer. The operation of magnetism collection, removal of the supernatant, HISCL washing solution addition and stirring was performed one more time.

(3) Binding of Second Capture Antibody

The magnetic particles in the particle suspension obtained in the above (2) were magnetically collected, and the supernatant was removed. To the magnetic particles was added 100 µL of a second capture antibody solution prepared by diluting 1 mg/mL biotinylated anti-HBs antibody (manufactured by Sysmex Corporation) 5000-fold with a diluent for HISCL (registered trademark) HBsAg R3 reagent (manufactured by Sysmex Corporation). The epitope of this second capture antibody is different from the epitope of the first capture antibody. The magnetic particles were dispersed and caused to react in a shaking thermostat set at 1600 rpm at 25° C. for 45 minutes. The magnetic particles were magnetically collected, and the supernatant was removed, then 200 µL of a HISCL (registered trademark) washing solution (manufactured by Sysmex Corporation) was added to disperse the magnetic particles. The operation of magnetism collection, removal of the supernatant, washing solution addition and dispersion was performed one more time.

(4) Binding of HRP Monomer

The magnetic particles in the particle suspension obtained in the above (3) were magnetically collected, and the supernatant was removed. To the magnetic particles was added 100 µL of 50 pM Streptavidin-HRP monomeric (SDT) diluted with 1% BSA/0.1% Tween 20/PBS (pH 7.4). The magnetic particles were dispersed and caused to react in a shaking thermostat set at 1600 rpm at 25° C. for 1 hour. The magnetic particles were magnetically collected, and the supernatant was removed, then 200 µL of a HISCL (registered trademark) washing solution (manufactured by Sysmex Corporation) was added to disperse the magnetic particles. The operation of magnetism collection, removal of the supernatant, washing solution addition and dispersion was performed two more times.

(5) Enzymatic Reaction

The magnetic particles in the particle suspension obtained in the above (4) were magnetically collected, and the supernatant was removed. To the magnetic particles was added a solution prepared by diluting a Biotin Amplification Reagent solution of TSA Plus Biotin Kit (product number NEL749B001KT, manufactured by Perkin Elmer) to 20-fold with 1× Plus Amplification Diluent so that the concentration of magnetic particles are $20 \times 10^6$ counts/mL, $200 \times 10^6$ counts/mL, $1000 \times 10^6$ counts/mL or $5000 \times 10^6$ counts/mL. The magnetic particles were dispersed, and the enzymatic reaction was carried out in a shaking thermostat set at 1600 rpm at 25° C. for 30 minutes. The magnetic particles were magnetically collected, and the supernatant was removed. To the magnetic particles was added 200 µL of a HISCL (registered trademark) washing solution (manufactured by Sysmex Corporation) to disperse the magnetic particles. The operation of magnetism collection, removal of the supernatant, washing solution addition and dispersion was performed one more time.

(6) Fluorescent Label

The magnetic particles in the particle suspension obtained in the above (5) were magnetically collected, and the supernatant was removed. To the magnetic particles was added 20 µL each of a Brilliant Violet (trademark) 421 Streptavidin (manufactured by BioLegend, Inc.) solution diluted 20-fold with 0.1% Tween 20/PBS (pH 7.4). The magnetic particles were dispersed and caused to react in a shaking thermostat set at 1300 rpm at 25° C. for 30 minutes. The magnetic particles were magnetically collected, and the supernatant was removed. To the magnetic particles was added 200 µL of a HISCL (registered trademark) washing solution (manufactured by Sysmex Corporation) to disperse the magnetic particles. The operation of magnetism collection, removal of the supernatant, washing solution addition and dispersion was performed one more time. The magnetic particles were magnetically collected, the supernatant was removed, and 10 µL of 0.1% Tween/PBS (pH 7.4) was added.

(7) Detection by Flow Cytometer

The particle suspension obtained in (6) above was added to 200 µL of PBS (pH 7.4) to disperse the magnetic particles. The resulting particle suspension was passed through a flow cytometer (FACS Verse, manufactured by Becton Dickinson), and the fluorescence intensity of each magnetic particle was measured. A wavelength of 408 nm was used for excitation light, and a filter for BD Horizon V450 was used for the detector optical filter. Here, the maximum fluorescence intensity +5SD when measuring only negative particles was used as a threshold value, and magnetic particles each having a fluorescence intensity equal to or greater than this threshold value were counted as positive particles. The total number of magnetic particles (negative particles) and positive particles each having a fluorescence intensity less than this threshold value was counted as all particles. The number of all particles represents the total number of magnetic particles subjected to detection.

(8) Results

As shown in FIG. 13, when the particle concentration was in the range of $20 \times 10^6$ to $1000 \times 10^6$ counts/mL, the proportion of positive particles was substantially constant. However, when the particle concentration was $5000 \times 10^6$ ($5 \times 10^9$) counts/mL, the proportion of positive particles sharply increased. It is considered due to the fact that the particle concentration is too high, and thus the distance between the particles becomes very close and the signal is diffused. That is, it is considered that the radicalized tyramide is bound not only to the carrier particle that captures an HBs antigen but also to the carrier particle that does not capture an HBs antigen. Therefore, when causing the enzyme to react with the substrate, the particle concentration is preferably less than $5 \times 10^9$ counts/mL.

(Example 8) Detection of Analyte Using Fluorescent Particles and HRP Polymer (1) Antigen-Antibody Reaction on Carrier Particle Using magnetic particles having an average particle size of 1 µm (Dynabeads Myone-COOH, manufactured by Life Technologies) according to the attached instruction, an anti-HBs antibody (manufactured by Sysmex Corporation) as a first capture antibody was immobilized on each of the magnetic particles. The resulting magnetic particles ($1.5 \times 10^6$ particles) were blocked with 1% BSA/PBS at room temperature for 2 hours. The magnetic particles were magnetically collected, and the supernatant was removed. Thereto was added 80 µL of HISCL (registered trademark) HBsAg R1 reagent (manufactured by Sysmex Corporation) to disperse the magnetic particles. Thereto was added 20 µL of C0 (0 IU/mL) of HISCL (registered trademark) HBsAg calibrator (manufactured by Sysmex Corporation), or an antigen solution obtained by diluting C1 10-fold (0.025 IU/mL) with a HISCL (registered trademark) specimen diluent. The magnetic particles were dispersed and caused to react in a shaking thermostat set at 1600 rpm at 25° C. for 2 hours. The magnetic particles were magnetically collected, and the supernatant was removed, then 200 µL of a HISCL (registered trademark) washing solution (manufactured by Sysmex Corporation) was added to disperse the magnetic particles. The operation of magnetism collection, removal of the supernatant, washing solution addition and dispersion was performed one more time.

The magnetic particles were magnetically collected, the supernatant was removed, and then 100 µL of a 1.3 nM biotinylated anti-HBs antibody (manufactured by Sysmex Corporation) was added as a second capture antibody. The epitope of this second capture antibody is different from the epitope of the first capture antibody. The magnetic particles were dispersed and caused to react in a shaking thermostat set at 1600 rpm at 25° C. for 30 minutes. The magnetic particles were magnetically collected, and the supernatant was removed, then 200 µL of a HISCL (registered trademark) washing solution (manufactured by Sysmex Corporation) was added to disperse the magnetic particles. The operation of magnetism collection, removal of the supernatant, washing solution addition and dispersion was performed one more time.

An HRP polymer having a degree of polymerization of 400 to which streptavidin was bound (Streptavidin Poly-HRP 80 Conjugate, manufactured by Stereospecific Detection Technologies) was diluted with 1% BSA/0.1% Tween 20/PBS (pH 7.4) to prepare a 51 pM enzyme solution. The magnetic particles were magnetically collected, the supernatant was removed, and then 300 µL of the enzyme solution was added. The magnetic particles were dispersed and caused to react in a shaking thermostat set at 1600 rpm at 25° C. for 1 hour. The magnetic particles were magnetically collected, and the supernatant was removed, then 200 µL of a HISCL (registered trademark) washing solution (manufactured by Sysmex Corporation) was added to disperse the magnetic particles. The operation of magnetism collection, removal of the supernatant, washing solution addition and dispersion was performed one more time.

(2) Enzymatic Reaction

A Biotin Tyramide solution of TSA Biotin System (product number NEL700001KT, manufactured by Perkin Elmer) was diluted 20-fold with Amplification Diluent. The magnetic particles were magnetically collected, the supernatant was removed, and then 50 µL of the diluted Biotin Tyramide solution was added. The magnetic particles were dispersed and caused to react in a shaking thermostat set at 1300 rpm at 25° C. for 30 minutes. The magnetic particles were magnetically collected, and the supernatant was removed. To the magnetic particles was added 200 µL of a HISCL (registered trademark) washing solution (manufactured by Sysmex Corporation) to disperse the magnetic particles. The operation of magnetism collection, removal of the supernatant, washing solution addition and dispersion was performed one more time.

(3) Immobilization of Fluorescent Particles

Streptavidin-modified fluorescent particles (F1-XC 030, manufactured by Merck KGaA) having an average particle size of 300 nm were used as detection particles. The fluorescent particles were diluted 100-fold with a diluent for HISCL (registered trademark) HBsAg R3 reagent (manufactured by Sysmex Corporation). The magnetic particles were magnetically collected, the supernatant was removed, and then 50 μL of a suspension of the fluorescent particles was added to disperse the magnetic particles. The suspension of the magnetic particles was caused to react in a shaking thermostat set at 1300 rpm and 25° C. for 20 minutes while being shielded. The magnetic particles were magnetically collected, and the supernatant was removed. To the magnetic particles was added 200 μL of a HISCL (registered trademark) washing solution (manufactured by Sysmex Corporation) to disperse the magnetic particles. The operation of magnetism collection, removal of the supernatant, washing solution addition and dispersion was performed one more time.

(4) Detection by Flow Cytometer

The magnetic particles were magnetically collected, the supernatant was removed, and then 20 μL of PBS (pH 7.4) was added to disperse the magnetic particles. The resulting particle suspension (10 μL) was diluted with 200 μL of FACS Flow (manufactured by Becton Dickinson). The resulting particle suspension was passed through a flow cytometer (FACS Verse, manufactured by Becton Dickinson), the fluorescence intensity of each magnetic particle was measured, and the particles were counted. A wavelength of 488 nm was used for excitation light, and a filter for FITC detection was used for the detector optical filter.

(5) Results

FIG. 14 shows a histogram created from the measurement results. In FIG. 14, the vertical axis represents the number of particles, and the horizontal axis represents the fluorescence intensity of particles. In addition, the solid line represents a histogram when diluted C1 (antigen concentration 0.025 IU/mL) is added, and the broken line represents a histogram when C0 (antigen concentration 0 IU/mL) is added. Since the calibrator C0 does not contain antigens, the broken line peak in FIG. 14 shows negative particles on each of which an HBs antigen that is a test substrate is not immobilized. In the histogram shown by the solid line in FIG. 14, a peak with low fluorescence intensity and a plurality of peaks with high fluorescence intensity were observed. The peak with low fluorescence intensity is considered to show negative particles because the peak almost overlaps with the broken line peak. On the other hand, a plurality of peaks with high fluorescence intensity is considered to show positive particles on which an HBs antigen is immobilized. It is considered that the presence of the plurality of peaks is due to the difference in the number of fluorescent particles bound to the carrier particles. As shown in FIG. 14, it was found that even when fluorescent particles were used in place of labeling with a fluorescent dye, positive particles could be detected while distinguished from negative particles.

(Example 9) Detection of Analyte Using Fluorescent Particles and HRP Monomer (1) Antigen-Antibody Reaction on Carrier Particle An anti-HBs antibody (manufactured by Sysmex Corporation) was immobilized on each of magnetic particles having an average particle size of 1 μm (Dynabeads Myone-COOH, manufactured by Life Technologies) in the same manner as in Example 8. The resulting magnetic particles ($1.5 \times 10^6$ particles) were blocked with 1% BSA/PBS at room temperature for 2 hours. The magnetic particles were magnetically collected, and the supernatant was removed. Thereto was added 80 μL of HISCL (registered trademark) HBsAg R1 reagent (manufactured by Sysmex Corporation) to disperse the magnetic particles. Thereto was added 20 μL of any of C0 (0 IU/mL) of HISCL (registered trademark) HBsAg calibrator (manufactured by Sysmex Corporation), an antigen solution obtained by diluting C1 10-fold (0.025 IU/mL) with a HISCL (registered trademark) specimen diluent and an antigen solution obtained by diluting C1 100-fold (0.0025 IU/mL) with a HISCL (registered trademark) specimen diluent. The magnetic particles were dispersed and caused to react in a shaking thermostat set at 1600 rpm at 25° C. for 2 hours. Then, the washing operation of the magnetic particles using a HISCL (registered trademark) washing solution (manufactured by Sysmex Corporation) was performed twice in the same manner as in Example 8.

The magnetic particles were magnetically collected, the supernatant was removed, and then 100 μL of a 1.3 nM biotinylated anti-HBs antibody (manufactured by Sysmex Corporation) was added as a second capture antibody. The epitope of this second capture antibody is different from the epitope of the first capture antibody. The magnetic particles were dispersed and caused to react in a shaking thermostat set at 1600 rpm at 25° C. for 30 minutes. Then, the washing operation of the magnetic particles using a HISCL (registered trademark) washing solution (manufactured by Sysmex Corporation) was performed twice in the same manner as in Example 8.

HRP monomers to each of which streptavidin was bound (Streptavidin HRP Conjugate, manufactured by Stereospecific Detection Technologies) were diluted with 1% BSA/ 0.1% Tween 20/PBS (pH 7.4) to prepare a 51 pM enzyme solution. The magnetic particles were magnetically collected, the supernatant was removed, and then 300 μL of the enzyme solution was added. The magnetic particles were dispersed and caused to react in a shaking thermostat set at 1600 rpm at 25° C. for 1 hour. Then, the washing operation of the magnetic particles using a HISCL (registered trademark) washing solution (manufactured by Sysmex Corporation) was performed twice in the same manner as in Example 8.

(2) Enzymatic Reaction

A Biotin Tyramide solution of TSA Biotin System (product number NEL700001KT, manufactured by Perkin Elmer) was diluted 20-fold with Amplification Diluent. The magnetic particles were magnetically collected, the supernatant was removed, and then 50 μL of the diluted Biotin Tyramide solution was added. The magnetic particles were dispersed and caused to react in a shaking thermostat set at 1300 rpm at 25° C. for 30 minutes. Then, the washing operation of the magnetic particles using a HISCL (registered trademark) washing solution (manufactured by Sysmex Corporation) was performed twice in the same manner as in Example 8.

(3) Immobilization of Fluorescent Particles

Fluorescent particles (F1-XC 030, manufactured by Merck KGaA) modified with streptavidin and having an average particle size of 300 nm were diluted 100-fold with a diluent for HISCL (registered trademark) HBsAg R3 reagent (manufactured by Sysmex Corporation). The magnetic particles were magnetically collected, the supernatant was removed, and then 50 μL of a suspension of the fluorescent particles was added to disperse the magnetic particles. The suspension of the magnetic particles was caused to react in a shaking thermostat set at 1300 rpm and 25° C. for 20 minutes while being shielded. Then, the washing operation of the magnetic particles using a HISCL (registered trademark) washing solution (manufactured by Sysmex Corporation) was performed twice in the same manner as in Example 8.

(4) Detection by Flow Cytometer

The magnetic particles were magnetically collected, the supernatant was removed, and then 20 μL of PBS (pH 7.4) was added to disperse the magnetic particles. The resulting particle suspension (10 μL) was diluted with 200 μL of FACS Flow (manufactured by Becton Dickinson). The resulting particle suspension was passed through a flow cytometer (FACS Verse, manufactured by Becton Dickinson), the fluorescence intensity of each magnetic particle was measured, and the particles were counted. A wavelength of 488 nm was used for excitation light, and a filter for FITC detection was used for the detector optical filter. Here, the maximum fluorescence intensity +5SD when measuring only negative particles was used as a threshold value, and magnetic particles each having a fluorescence intensity equal to or greater than this threshold value were counted as positive particles. The total number of magnetic particles (negative particles) and positive particles each having a fluorescence intensity less than this threshold value was counted as all particles. The number of all particles represents the total number of magnetic particles subjected to detection.

(5) Results

FIG. 15 shows the correlation between the HBs antigen concentration and the proportion (%) of the number of positive particles to the number of all particles. The proportion (%) of positive particles was calculated as [(number of positive particles counted by flow cytometer)/(number of all particles counted by flow cytometer)]×100. As shown in FIG. 15, the proportion of positive particles increased in an antigen concentration-dependent manner. Therefore, in the case of binding the fluorescent particles to the carrier particles, it was found that an antigen concentration-dependent signal can be acquired even when an HRP monomer is used as the catalyst.

(Example 10) Investigation of Particle Size of Fluorescent Particles (1) Antigen-Antibody Reaction on Carrier Particle An anti-HBs antibody (manufactured by Sysmex Corporation) was immobilized on each of magnetic particles in the same manner as in Example 8, except for using magnetic particles having an average particle size of 2.8 μm (manufactured by Life Technologies) in place of the magnetic particles described in Example 8. The resulting magnetic particles (1.5×10⁶ particles) were blocked with 1% BSA/ PBS at room temperature for 2 hours. The magnetic particles were magnetically collected, and the supernatant was removed. Thereto was added 80 μL of HISCL (registered trademark) HBsAg R1 reagent (manufactured by Sysmex Corporation) to disperse the magnetic particles. Thereto was added 20 μL of C0 (0 IU/mL) or C1 (0.25 IU/mL) of HISCL (registered trademark) HBsAg calibrator (manufactured by Sysmex Corporation). The magnetic particles were dispersed and caused to react in a shaking thermostat set at 1600 rpm at 25° C. for 2 hours. Then, the washing operation of the magnetic particles using a HISCL (registered trademark) washing solution (manufactured by Sysmex Corporation) was performed twice in the same manner as in Example 8.

The magnetic particles were magnetically collected, the supernatant was removed, and then 100 μL of a 1.3 nM biotinylated anti-HBs antibody (manufactured by Sysmex Corporation) was added as a second capture antibody. The epitope of this second capture antibody is different from the epitope of the first capture antibody. The magnetic particles were dispersed and caused to react in a shaking thermostat set at 1600 rpm at 25° C. for 30 minutes. Then, the washing operation of the magnetic particles using a HISCL (registered trademark) washing solution (manufactured by Sysmex Corporation) was performed twice in the same manner as in Example 8.

HRP monomers to each of which streptavidin was bound (Streptavidin HRP Conjugate, manufactured by Stereospecific Detection Technologies) were diluted with 1% BSA/ 0.1% Tween 20/PBS (pH 7.4) to prepare a 51 pM enzyme solution. The magnetic particles were magnetically collected, the supernatant was removed, and then 300 μL of the enzyme solution was added. The magnetic particles were dispersed and caused to react in a shaking thermostat set at 1600 rpm at 25° C. for 1 hour. Then, the washing operation of the magnetic particles using a HISCL (registered trademark) washing solution (manufactured by Sysmex Corporation) was performed twice in the same manner as in Example 8.

(2) Enzymatic Reaction

A Biotin Tyramide solution of TSA Biotin System (product number NEL700001KT, manufactured by Perkin Elmer) was diluted 20-fold with Amplification Diluent. The magnetic particles were magnetically collected, the supernatant was removed, and then 50 μL of the diluted Biotin Tyramide solution was added. The magnetic particles were dispersed and caused to react in a shaking thermostat set at 1300 rpm at 25° C. for 30 minutes. Then, the washing operation of the magnetic particles using a HISCL (registered trademark) washing solution (manufactured by Sysmex Corporation) was performed twice in the same manner as in Example 8.

(3) Immobilization of Fluorescent Particles

As the streptavidin-modified fluorescent particles, fluorescent particles having average particle sizes of 160 nm, 200 nm, 300 nm, 400 nm and 500 nm (all manufactured by Merck KGaA) were prepared. These fluorescent particles have average particle sizes of 5.7%, 7.1%, 10.7%, 14.3% and 17.8%, respectively, with respect to the average particle size (2.8 μm) of the magnetic particles. These fluorescent particles were each diluted 100-fold with a diluent for HISCL (registered trademark) HBsAg R3 reagent (manufactured by Sysmex Corporation). The magnetic particles were magnetically collected, the supernatant was removed, and then 50 μL of a suspension of the fluorescent particles was added to disperse the magnetic particles. The suspension of the magnetic particles was caused to react in a shaking thermostat set at 1300 rpm and 25° C. for 20 minutes while being shielded. Then, the washing operation of the magnetic particles using a HISCL (registered trademark) washing solution (manufactured by Sysmex Corporation) was performed twice in the same manner as in Example 8.

(4) Detection by Flow Cytometer

The magnetic particles were magnetically collected, the supernatant was removed, and then 20 μL of PBS (pH 7.4) was added to disperse the magnetic particles. The resulting particle suspension (10 μL) was diluted with 200 μL of FACS Flow (manufactured by Becton Dickinson). The resulting particle suspension was passed through a flow cytometer (FACS Verse, manufactured by Becton Dickinson), the fluorescence intensity of each magnetic particle was measured, and the particles were counted. A wavelength of 488 nm was used for excitation light, and a filter for FITC detection was used for the detector optical filter.

(5) Results

The results of causing to react with diluted C1 (antigen concentration 0.25 IU/mL) and measuring magnetic particles to each of which fluorescent particles are bound by FCM are shown in FIGS. 16A, 16B, 16C, 16D, and 16E. In these figures, the horizontal axis represents fluorescence intensity, and the vertical axis represents forward scattered light intensity (size of particles). In these figures, a population with low fluorescence intensity and a population with high fluorescence intensity were observed. The population with low fluorescence intensity is a population of negative particles to each of which fluorescent particles are not bound and the population with high fluorescence intensity is considered to be a population of positive particles to each of which fluorescent particles are bound. As shown in these figures, it is found that negative particles and positive particles can be distinguished by setting an appropriate threshold value. In particular, it was shown that when fluorescent particles having an average particle size of 300 nm or more are used, it is possible to clearly distinguish between negative particles and positive particles.

(Example 11) Detection of Carrier Particles Using Multi-Substrate (1) Capture of HRP Biotin-bound BSA (manufactured by Sysmex Corporation) was immobilized on each of magnetic particles having an average particle size of 2 μm (micromerM-COOH, manufactured by micromod Partikeltechnologie GmbH). The resulting magnetic particles ($10^6$ particles) were dispersed in 80 μL of PBS (pH 7.4). HRP to which streptavidin was bound (Streptavidin Poly-HRP 80 Conjugate, manufactured by Stereospecific Detection Technologies) was diluted with PBS (pH 7.4) to prepare a 100 pg/mL HRP solution. In addition, PBS (pH 7.4) was used as a 0 pg/mL HRP solution. The 0 pg/mL or 100 pg/mL HRP solution (20 μL) was added to 80 μL of the above particle suspension, and the mixture was caused to react in a thermostat set at 1600 rpm and 25° C. for 1 hour. Each particle suspension was taken out from the shaking thermostat, and after magnetism collection, the supernatant was removed, 80 μL of PBS (pH 7.4) was added, and the mixture was stirred with a vortex mixer. The operation of magnetism collection, removal of the supernatant, PBS addition and stirring was performed one more time.

(2) Preparation of Multi-Substrate

Qdot (registered trademark) nanocrystal (Qdot (registered trademark) 585 Streptavidin Conjugate, manufactured by invitrogen) to which streptavidin was bound was used as a support that generates fluorescence. This nanocrystal was diluted 5-fold with an Amplification buffer in the TSA plus biotin kit (manufactured by Life technologies) to prepare a nanocrystal solution. In Qdot (registered trademark) 585 Streptavidin Conjugate, a plurality (usually 5 to 10 molecules) of streptavidin is bound to one nanocrystal. This nanocrystal solution, the biotin-tyramide in the kit and the Amplification buffer were mixed to react in a shaking thermostat set at 1600 rpm at 25° C. for 20 minutes, so that a solution containing a nanocrystal on which a plurality of tyramide molecules was immobilized (multi-substrate) was prepared.

(3) Enzymatic Reaction

The carrier particles in each particle suspension obtained in the above (1) were magnetically collected, and the supernatant was removed. Thereto was added 20 μL each of the solution containing the above multi-substrate. The carrier particles were dispersed and caused to react in a shaking thermostat set at 1300 rpm and 25° C. for 30 minutes. Each particle suspension was taken out from the shaking thermostat, and after magnetism collection, the supernatant was removed, 80 μL of PBS (pH 7.4) was added, and the mixture was stirred with a vortex mixer. The operation of magnetism collection, removal of the supernatant, PBS addition and stirring was performed one more time.

(4) Detection by Microscope

The carrier particles in each particle suspension obtained in the above (3) were magnetically collected, and the supernatant was removed. Thereto was added 50 μL of PBS (pH 7.4), and the mixture was stirred. The particle suspension (10 μL) was collected from the resulting particle suspension and dropped onto a microscopic slide glass for sedimentation (manufactured by Matsunami Glass Ind., Ltd.). Using a fluorescence microscope (BZX710, manufactured by KEYENCE CORPORATION) equipped with an excitation filter and a fluorescence filter of a wavelength appropriate to detect Qdot (registered trademark) 585 as a fluorescent substance, a bright field image and a fluorescence image were imaged using a 40× objective lens. The exposure time for fluorescent image acquisition was set to $1/10$ seconds. The acquired images were analyzed using image analysis software ImageJ. As the number of fluorescent positive particles in the image, the bright spots higher than the maximum fluorescence brightness of negative particles in the fluorescence image were counted. In addition, signals in the image were binarized by the threshold of ImageJ in the bright field image, and the number of all magnetic particles in the image was counted with Particle tool.

(5) Results

Table 3 shows the proportion (%) of the number of positive particles to the number of all particles and the proportion (%) of the area of positive particles to the area of all particles observed with a fluorescence microscope. The proportion (%) of positive particles to the number of all particles was calculated as (number of positive particles counted by fluorescence microscope)/(number of all particles counted by fluorescence microscope)×100. The proportion (%) of the area of positive particles to the area of all particles observed with a microscope is calculated as (sum of areas of fluorescent moieties in fluorescence image observed with fluorescence microscope)/(sum of areas of particles in bright field image observed with fluorescence microscope)×100. The "areas of fluorescent moieties in fluorescence image observed with fluorescence microscope" and the "areas of particles in bright field image observed with fluorescence microscope" are not the surface area of each of the particles but the area on the image. For the analysis of the values shown in Table 3, the value obtained by subtracting the signal value when PBS (HRP concentration 0 pg/mL) was added as the background from the signal value when the 100 pg/mL HRP solution was added was used.

TABLE 3

| HRP concentration (pg/mL) | Proportion (%) of number of positive particles | Proportion (%) of area of positive particles |
| --- | --- | --- |
| 100 | 18.8 | 21.7 |

As shown in Table 3, it was found that carrier particles can be detected even when using a support to which a plurality of tyramide molecules is bound as a substrate.

(Example 12) Investigation of Particle Size of Carrier Particles (1) Antigen-Antibody Reaction on Carrier Particle As magnetic particles, polymer latex particles having an average particle size of 30 μm (Micromer-COOH, manufactured by micromod Partikeltechnologie GmbH) and polymer latex particles having an average particle size of 100 μm (Micromer-COOH, manufactured by micromod Partikeltechnologie GmbH) were prepared. An anti-HBs antibody (manufactured by Sysmex Corporation) as a first capture antibody was immobilized on each of these polymer latex particles. The resulting polymer latex particles (both cases: $10^5$ particles) were blocked with 1% BSA/PBS at room temperature for 2 hours. The particle suspension was centrifuged, and the supernatant was removed. Thereto was added 80 μL of HISCL (registered trademark) HBsAg R1 reagent (manufactured by Sysmex Corporation) to disperse the polymer latex particles.

C5 of HISCL (registered trademark) HBsAg calibrator (manufactured by Sysmex Corporation) was diluted with a HISCL (registered trademark) specimen diluent to prepare antigen solutions having antigen concentrations of 0.0025 IU/mL, 0.025 IU/mL and 0.25 IU/mL. CO (0 IU/mL) of HISCL (registered trademark) HBsAg calibrator (manufactured by Sysmex Corporation) (20 μL) or 20 μL of the prepared antigen solution was added to the particle suspension. The polymer latex particles were dispersed, and the dispersion was caused to react in a shaking thermostat set at 1600 rpm and 25° C. for 1 hour. The particle suspension was centrifuged, the supernatant was removed, and then 200 μL of a HISCL (registered trademark) washing solution (manufactured by Sysmex Corporation) was added to disperse the magnetic particles.

The particle suspension was centrifuged, the supernatant was removed, and then 100 μL of a 1.3 nM biotinylated anti-HBs antibody (manufactured by Sysmex Corporation) was added as a second capture antibody. The epitope of this second capture antibody is different from the epitope of the first capture antibody. The polymer latex particles were dispersed, and the dispersion was caused to react in a shaking thermostat set at 1600 rpm and 25° C. for 1 hour. The particle suspension was centrifuged, the supernatant was removed, and then 200 μL of HISCL (registered trademark) washing solution (manufactured by Sysmex Corporation) was added to disperse the polymer latex particles.

HRP to which streptavidin was bound (Streptavidin HRP Conjugate, manufactured by Stereospecific Detection Technologies) was diluted with 1% BSA/0.1% Tween 20/PBS (pH 7.4) to prepare a 51 pM enzyme solution. The particle suspension was centrifuged, the supernatant was removed, and then 100 μL of the enzyme solution was added. The polymer latex particles were dispersed, and the dispersion was caused to react in a shaking thermostat set at 1600 rpm and 25° C. for 1 hour. The particle suspension was centrifuged, the supernatant was removed, and then 200 μL of a HISCL (registered trademark) washing solution (manufactured by Sysmex Corporation) was added to disperse the magnetic particles. The operation of centrifugal separation, removal of the supernatant, washing solution addition and dispersion was performed one more time.

(2) Enzymatic Reaction

A Biotin Tyramide solution of TSA Biotin System (product number NEL700001KT, manufactured by Perkin Elmer) was diluted 100-fold with an Amplification Diluent. The particle suspension was centrifuged, the supernatant was removed, and then 50 μL of the diluted Biotin Tyramide solution was added. The polymer latex particles were dispersed, and the dispersion was caused to react in a shaking thermostat set at 1600 rpm and 25° C. for 30 minutes. The particle suspension was centrifuged, and the supernatant was removed. To the magnetic particles was added 200 μL of a HISCL (registered trademark) washing solution (manufactured by Sysmex Corporation) to disperse the magnetic particles.

(3) Fluorescent Label

A fluorescent dye to which streptavidin was bound (Brilliant Violet (trademark) 421 Streptavidin, manufactured by BioLegend, Inc.) was diluted 100-fold with a Stain Buffer (manufactured by Becton Dickinson) to prepare a fluorescent dye solution. The particle suspension obtained in the above (2) was centrifuged, the supernatant was removed, and then 20 μL of the prepared fluorescent dye solution was added. The particle suspension was caused to react in a shaking thermostat set at 1600 rpm and 25° C. for 30 minutes while being shielded. The particle suspension was centrifuged, and the supernatant was removed. To the polymer latex particles was added 200 μL of a HISCL (registered trademark) washing solution (manufactured by Sysmex Corporation) to disperse the polymer latex particles.

(4) Detection by Microscope

Each particle suspension obtained in the above (3) was centrifuged, and the supernatant was removed. Thereto was added 20 μL of PBS (pH 7.4), and the mixture was stirred. The particle suspension (10 μL) was collected from the resulting particle suspension and dropped onto a microscopic slide glass for sedimentation (manufactured by Matsunami Glass Ind., Ltd.). Using a fluorescence microscope (BZX710, manufactured by KEYENCE CORPORATION) equipped with an excitation filter and a fluorescence filter of a wavelength appropriate to detect Brilliant Violet (registered trademark) 421, a bright field image and a fluorescence image were imaged using a 20× objective lens. The exposure time for fluorescent image acquisition was set to 1/30 seconds. The acquired images were analyzed using image analysis software ImageJ.

As the number of fluorescent positive particles in the image, the bright spots higher than the maximum fluorescence brightness of negative particles in the fluorescence image were counted. In addition, signals in the image were binarized by the threshold of ImageJ in the bright field image, and the number of all magnetic particles in the image was counted with Particle tool.

(5) Results

The results are shown in FIG. 18. In FIG. 18, the vertical axis represents the number of positive particles, and the horizontal axis represents the antigen concentration. White circles indicate data on the particle size of carrier carries having an average particle size of 30 μm, and black circles indicate data on the particle size of carrier particles having an average particle size of 100 μm. The number of positive particles was calculated as [(number of positive particles counted by fluorescence microscope)/(number of all particles counted with fluorescence microscope)]×(number of particles per assay). As shown in FIG. 18, even when the carrier particles having an average particle size of 30 μm and 100 μm were used, a signal dependent on the HBs antigen concentration could be detected.

(Example 13) Multiplex Detection (1) Antigen-Antibody Reaction on Carrier Particle An anti-IL-6 antibody (manufactured by R&D systems, Inc.) as a first capture antibody was immobilized on each of magnetic particles having an average particle size of 2.8 μm (Dynabeads, manufactured by Life Technologies). In addition, an anti-HBs antibody (manufactured by Sysmex Corporation) as a third capture antibody was immobilized on each of magnetic particles having an average particle size of 4.5 μm (Dynabeads, manufactured by Life Technologies). The resulting magnetic particles (both cases: $1\times10^7$ particles) were blocked with 1% BSA/PBS at room temperature for 2 hours. The magnetic particles were magnetically collected, and the supernatant was removed. Thereto was added 250 μL of HISCL (registered trademark) HBsAg R1 reagent (manufactured by Sysmex Corporation) to disperse the magnetic particles. The two kinds of the resulting particle suspensions were mixed to obtain a particle suspension (500 μL, the number of particles $2\times10^7$ particles) containing magnetic particles on each of which the anti-IL-6 antibody was immobilized and magnetic particles on each of which the anti-HBs antibody was immobilized.

As an analyte, a mixture of HBs antigen and recombinant human IL-6 was used. Specifically, HISCL (registered trademark) HBsAg calibrator (manufactured by Sysmex Corporation) and recombinant human IL-6 (manufactured by BioLegend, Inc.) were diluted with HISCL (registered trademark) HBsAg R1 reagent (manufactured by Sysmex Corporation) and mixed so as to have concentrations shown in Table 4 to prepare an antigen sample. HISCL (registered trademark) HBsAg R1 reagent (manufactured by Sysmex Corporation) was used as a sample containing no antigen (Antigen sample 1).

TABLE 4

|  | HBsAg (IU/mL) | IL-6 (pg/mL) |
|---|---|---|
| Antigen sample 1 | 0 | 0 |
| Antigen sample 2 | 0.013 | 0.1 |
| Antigen sample 3 | 0.13 | 1 |
| Antigen sample 4 | 1.3 | 10 |

The above particle suspension (50 μL) and Antigen sample 1, 2, 3 or 4 (50 μL each) were mixed to react in a shaking thermostat set at 1300 rpm and 25° C. for 2 hours. The magnetic particles were magnetically collected, and the supernatant was removed, then 200 μL of a HISCL (registered trademark) washing solution (manufactured by Sysmex Corporation) was added to disperse the magnetic particles. The operation of magnetism collection, removal of the supernatant, washing solution addition and dispersion was performed one more time.

The magnetic particles were magnetically collected, and the supernatant was removed. To the magnetic particles was added 100 μL of 1% BSA/0.1% Tween 20/PBS (pH 7.4) containing a biotinylated anti-HBs antibody (manufactured by Sysmex Corporation) at a concentration of 0.13 μg/mL as the second and fourth capture antibodies and a biotinylated anti-IL-6 antibody (manufactured by R&D systems, Inc.) at a concentration of 0.2 μg/mL. The magnetic particles were dispersed and caused to react in a shaking thermostat set at 1300 rpm at 25° C. for 45 minutes. The magnetic particles were magnetically collected, and the supernatant was removed, then 200 μL of a HISCL (registered trademark) washing solution (manufactured by Sysmex Corporation) was added to disperse the magnetic particles. The operation of magnetism collection, removal of the supernatant, washing solution addition and dispersion was performed one more time. The magnetic particles were magnetically collected, and the supernatant was removed. To the magnetic particles was added 100 μL of 1% BSA/0.1% Tween 20/PBS (pH 7.4) containing streptavidin-bound HRP (manufactured by Stereo specific Detection Technologies) at a concentration of 5 ng/mL. The magnetic particles were dispersed and caused to react in a shaking thermostat set at 1300 rpm at 25° C. for 1 hour. The magnetic particles were magnetically collected, and the supernatant was removed, then 200 μL of a HISCL (registered trademark) washing solution (manufactured by Sysmex Corporation) was added to disperse the magnetic particles. The operation of magnetism collection, removal of the supernatant, washing solution addition and dispersion was performed one more time.

(2) Enzymatic Reaction

A Biotin Tyramide solution of TSA Biotin System (product number NEL700001KT, manufactured by Perkin Elmer) was diluted 100-fold with an Amplification Diluent. The magnetic particles were magnetically collected, the supernatant was removed, and then 50 μL of the diluted Biotin Tyramide solution was added. The magnetic particles were dispersed and caused to react in a shaking thermostat set at 1300 rpm at 25° C. for 30 minutes. The magnetic particles were magnetically collected, and the supernatant was removed. To the magnetic particles was added 200 μL of a HISCL (registered trademark) washing solution (manufactured by Sysmex Corporation) to disperse the magnetic particles. The operation of magnetism collection, removal of the supernatant, washing solution addition and dispersion was performed one more time.

(3) Fluorescent Label

A fluorescent dye to which streptavidin was bound (Brilliant Violet (trademark) 421 Streptavidin, manufactured by BioLegend, Inc.) was diluted 100-fold with a Stain Buffer (manufactured by Becton Dickinson) to prepare a fluorescent dye solution at a concentration of 2 μg/mL. The particle suspension obtained in the above (2) was centrifuged, the supernatant was removed, and then 20 μL of the prepared fluorescent dye solution was added. The particle suspension was caused to react in a shaking thermostat set at 1600 rpm and 25° C. for 45 minutes while being shielded. The particle suspension was centrifuged, and the supernatant was removed. To the magnetic particles was added 200 μL of a HISCL (registered trademark) washing solution (manufactured by Sysmex Corporation) to disperse the magnetic particles.

(4) Detection by Flow Cytometer

The magnetic particles were magnetically collected, the supernatant was removed, and then 150 μL of FACS Flow (manufactured by Becton Dickinson) was added to disperse the magnetic particles. The resulting particle suspension was passed through a flow cytometer (FACS Verse, manufactured by Becton Dickinson), the fluorescence intensity and scattered light intensity of each magnetic particle were measured, and the particles were counted. A wavelength of 408 nm was used for excitation light, and a filter for BD Horizon V450 was used for the detector optical filter. On the two-dimensional scattergram of scattered light intensity and fluorescence intensity, the fluorescence intensities of the particles included in the population having a particle size of 2.8 μm and the population having a particle size of 4.5 μm were analyzed to calculate the proportion (%) of positive particles for each antigen.

(5) Results

The above detection was performed twice, and the results are shown in FIGS. 19A and 19B. As shown in FIG. 19A, the proportion of positive particles increased in an IL-6 concentration-dependent manner. In addition, as shown in FIG. 19B, the proportion of positive particles increased in an HBs antigen concentration-dependent manner. Therefore, it was found that two kinds of analytes can be simultaneously detected by the method of the present embodiment.

(Example 14) Detection of Exosome (1) Antigen-Antibody Reaction on Carrier Particle An anti-CD 147 antibody (manufactured by Becton Dickinson) as a first capture antibody was immobilized on each of magnetic particles having an average particle size of 2.8 μm (Dynabeads, manufactured by Life Technologies). The magnetic particles were magnetically collected, and the supernatant was removed. 1% BSA/0.1% Tween 20/PBS (pH 7.4) (80 μL) was added to the resulting magnetic particles (number of particles $1 \times 10^6$), and the mixture was blocked at 37° C. for 30 minutes.

Exosome derived from the culture supernatant of the human colon cancer cell line COLO1 was used as an analyte. Specifically, COLO-1 (Lyophilized exosomes from COLO1 cell culture supernatant, manufactured by HansaBioMed Life Sciences) was diluted with 1% BSA/0.1% Tween 20/PBS (pH 7.4) to prepare antigen solutions having exosome concentrations of 0.0015 mg/mL, 0.005 mg/mL, and 0.015 mg/mL. 1% BSA/0.1% Tween 20/PBS (pH 7.4) was used as a sample containing no antigen (exosome concentration 0 mg/mL).

The blocked magnetic particles were magnetically collected, and the supernatant was removed. Thereto was added 20 μL of the above sample. The magnetic particles were dispersed and caused to react in a shaking thermostat set at 1000 rpm at 37° C. for 1 hour. The magnetic particles were magnetically collected, and the supernatant was removed, then 200 μL of a HISCL (registered trademark) washing solution (manufactured by Sysmex Corporation) was added to disperse the magnetic particles.

The magnetic particles were magnetically collected, and the supernatant was removed. To the magnetic particles was added 100 μL of a biotinylated anti-CD9 antibody (manufactured by BioLegend, Inc.) at a concentration of 50 ng/mL. The magnetic particles were dispersed and caused to react in a shaking thermostat set at 1000 rpm at 37° C. for 1 hour. The magnetic particles were magnetically collected, and the supernatant was removed, then 200 μL of a HISCL (registered trademark) washing solution (manufactured by Sysmex Corporation) was added to disperse the magnetic particles. The operation of magnetism collection, removal of the supernatant, washing solution addition and dispersion was performed one more time.

HRP to which streptavidin was bound (Streptavidin HRP Conjugate, manufactured by Stereospecific Detection Technologies) was diluted with 1% BSA/0.1% Tween 20/PBS (pH 7.4) to prepare a 51 pM enzyme solution. The magnetic particles were magnetically collected, the supernatant was removed, and then 100 μL of the enzyme solution was added. The magnetic particles were dispersed and caused to react in a shaking thermostat set at 1000 rpm at 37° C. for 30 minutes. The magnetic particles were magnetically collected, and the supernatant was removed, then 200 μL of a HISCL (registered trademark) washing solution (manufactured by Sysmex Corporation) was added to disperse the magnetic particles.

(2) Enzymatic Reaction

A Biotin Tyramide solution of TSA Biotin System (product number NEL700001KT, manufactured by Perkin Elmer) was diluted 100-fold with an Amplification Diluent. The magnetic particles were magnetically collected, the supernatant was removed, and then 50 μL of the diluted Biotin Tyramide solution was added. The magnetic particles were dispersed and caused to react in a shaking thermostat set at 1000 rpm at 25° C. for 30 minutes. The magnetic particles were magnetically collected, and the supernatant was removed. To the magnetic particles was added 200 μL of a HISCL (registered trademark) washing solution (manufactured by Sysmex Corporation) to disperse the magnetic particles.

(3) Fluorescent Label

A fluorescent dye to which streptavidin was bound (Brilliant Violet (trademark) 421 Streptavidin, manufactured by BioLegend, Inc.) was diluted 100-fold with 0.1% Tween 20/PBS (pH 7.4) to prepare a fluorescent dye solution. The magnetic particles were magnetically collected, and the supernatant was removed, then 50 μL of the prepared fluorescent dye solution was added. The particle suspension was caused to react in a shaking thermostat set at 1000 rpm and 25° C. for 30 minutes while being shielded. The particle suspension was centrifuged, and the supernatant was removed. To the magnetic particles was added 200 μL of a HISCL (registered trademark) washing solution (manufactured by Sysmex Corporation) to disperse the magnetic particles.

(4) Detection by Flow Cytometer

The particle suspension (5 μL) obtained in the above (3) was diluted with 200 μL of FACS Flow (manufactured by Becton Dickinson). The resulting particle suspension was passed through a flow cytometer (FACS Verse, manufactured by Becton Dickinson), the fluorescence intensity of each magnetic particle was measured, and the particles were counted. A wavelength of 408 nm was used for excitation light, and a filter for BD Horizon V450 was used for the detector optical filter. Here, the maximum fluorescence intensity +5SD when measuring only negative particles was used as a threshold value, and magnetic particles each having a fluorescence intensity equal to or greater than this threshold value were counted as positive particles. The total number of magnetic particles (negative particles) and positive particles each having a fluorescence intensity less than this threshold value was counted as all particles. The number of all particles represents the total number of magnetic particles subjected to detection.

(5) Results

The results are shown in FIG. 20. As shown in FIG. 20, the proportion of positive particles increased in an exosome concentration-dependent manner. Therefore, it was found that exosome can be detected as an analyte by the method of the present embodiment.

This application relates to Japanese Patent Application No. 2015-50205 filed on Mar. 13, 2015, Japanese Patent Application No. 2015-169206 filed on Aug. 28, 2015 and Japanese Patent Application No. 2016-14744 filed on Jan. 28, 2016, and these claims, specifications, drawings and abstracts are entirely incorporated herein by reference.

REFERENCE SIGNS LIST 10, 20, 30, 40, 50, 60, 70, 80, 90, 100: Reagent kit
11, 21, 31, 41, 51, 61, 71, 81, 91, 101: First container
12, 22, 32, 42, 52, 62, 72, 82, 92, 102: Second container
13, 23, 33, 43, 53, 63, 73, 83, 93, 103: Third container
14, 34, 44, 64, 74, 84, 94, 104: Fourth container
15, 65, 85, 95: Fifth container
66: Sixth container
16, 24, 35, 45, 54, 67, 75, 86, 96, 105: Package insert
17, 25, 36, 46, 55, 68, 76, 87, 97, 106: Packing box

The invention claimed is:

1. A method for detecting an analyte in a sample, the method comprising the steps of:
forming on each of carrier particles a complex containing a first capture substance capable of binding to an analyte, one molecule of the analyte, a second capture substance capable of binding to the analyte, and a catalyst;
immobilizing a reaction product on each of the carrier particles by reacting the catalyst in the complex with a substrate; and
detecting the analyte by detecting the carrier particles on each of which the reaction product is immobilized, wherein
one molecule of the analyte is captured per one carrier particle in the formation step;
the reaction product is immobilized on the carrier particles on each of which the catalyst that has produced the reaction product is immobilized, but is not substantially immobilized on another carrier particle in the immobilization step;
the formation step comprises a step of mixing the sample and a reagent containing a plurality of the carrier particles;
each carrier particle is suspended in solution and not compartmentalized in the detection step; and
each carrier particle is not compartmentalized in the immobilization step.

2. The method according to claim 1, wherein in the immobilization step, optical properties of the carrier particles are changed by immobilizing the reaction product on each of the carrier particles, and in the detection step, the analyte is detected by detecting optical information of the carrier particles.

3. The method according to claim 1, wherein
the immobilization step is performed in a solution containing the carrier particles and the substrate, the complex being immobilized on each of carrier particles, and
the reaction between the catalyst in the complex and the substrate is carried out in a state that the carrier particles are dispersed in the solution.

4. The method according to claim 1, wherein in the immobilization step, detection particles are further immobilized on the carrier particles.

5. The method according to claim 4, wherein the detection particles are fluorescent particles.

6. The method according to claim 1, wherein the substrate contains: a support which generates a detectable signal; and a plurality of substrate molecules.

7. The method according to claim 1, wherein the detection step is performed in a solution containing a plurality of carrier particles, and each of the carrier particles is not compartmentalized in the solution.

8. The method according to claim 1, wherein
the substrate is a substrate comprising a label,
a reaction product comprising the label is generated and the reaction product comprising the label is immobilized on each of the carrier particles in the immobilization step, and
the analyte is detected based on the label of the reaction product immobilized on each of the carrier particles in the detection step.

9. The method according to claim 1, wherein in the detection step,
optical information of the carrier particles is measured, a measured value of the optical information is compared with a predetermined threshold value, and carrier particles in which the measured value is equal to or greater than the predetermined threshold are detected as carrier particles to each of which the reaction product is bound.

10. The method according to claim 4, wherein
the detection particles are immobilized to each of the carrier particles via the reaction product in the immobilization step, and
the analyte is detected by detecting the carrier particles on each of which the detection particles are immobilized in the detection step.

11. The method according to claim 1, wherein
the catalyst is a peroxidase,
the substrate is labeled tyramide,
the reaction product is radicalized tyramide,
the radicalized labeled tyramide is immobilized on each of carrier particles on each of which the peroxidase that has radicalized the labeled tyramide is immobilized, so that a fluorescence intensity of the carrier particles changes in the immobilization step, and
the analyte is detected by detecting the fluorescence intensity of the carrier particles in the detection step.

12. The method according to claim 4, wherein
the catalyst is a peroxidase,
the substrate contains detection particles and tyramide,
the reaction product is radicalized tyramide,
the detection particles are fluorescent particles,
the radicalized tyramide is immobilized on each of carrier particles on each of which the peroxidase that has radicalized the labeled tyramide is immobilized, and the fluorescent particles are further immobilized on each of the carrier particles on each of which the tyramide is immobilized, so that a fluorescence intensity of the carrier particles changes in the immobilization step, and
the analyte is detected by detecting the fluorescence intensity of the carrier particles in the detection step.

13. The method according to claim 1, wherein
the catalyst is a peroxidase,
the substrate contains a support and a plurality of tyramide molecules,
the reaction product is radicalized tyramide,
the radicalized tyramide is immobilized on each of carrier particles on each of which the peroxidase that has radicalized the tyramide is immobilized, so that a fluorescence intensity of the carrier particles changes in the immobilization step, and
the analyte is detected by detecting the fluorescence intensity of the carrier particles in the detection step.

14. The method according to claim 1, wherein the detection step comprises the steps of:
counting carrier particles to each of which the reaction product is bound; and
quantifying the analyte based on a result of the count.

15. The method according to claim 14, wherein the detection step comprises the steps of:
counting a total number of carrier particles subjected to detection; and
quantifying the analyte based on a result of counting the carrier particles to each of which the reaction product is bound.

16. The method according to claim 1, wherein each carrier particle is not compartmentalized in the formation step.

17. The method according to claim 1, wherein each carrier particle is not compartmentalized throughout the method.

18. The method according to claim 1, wherein a plurality of molecules of the reaction products are immobilized on one carrier particle on which one molecule of the analyte is immobilized.

19. A method for distinctly detecting in a sample a first analyte and a second analyte of a different kind of the first analyte, the method comprising the steps of:
- forming on first carrier particles a first complex containing a first capture substance capable of binding to a first analyte, one molecule of the first analyte, a second capture substance capable of binding to the first analyte, and a catalyst;
- forming on second carrier particles a second complex containing a third capture substance capable of binding to a second analyte, one molecule of the second analyte, a fourth capture substance capable of binding to the second analyte, and a catalyst;
- immobilizing a reaction product on each of the first and second carrier particles by reacting the respective catalyst in the respective complex with a substrate; and
- distinctly detecting the first analyte and the second analyte by detecting the first and second carrier particles on each of which the reaction product is immobilized, wherein
- the formation step comprises a step of mixing the sample and a reagent containing a plurality of the first and second carrier particles;
- one molecule of either of the first analyte and the second analyte is captured per one carrier particle of the first and second carrier particles by the formation step;
- the reaction product is immobilized on each of the first and second carrier particles on each of which the catalyst that has produced the reaction product is immobilized, but is not substantially immobilized on another carrier particle in the immobilization step;
- the first carrier particles on each of which the first analyte is immobilized and the second carrier particles on each of which the second analyte is immobilized generate mutually distinguishable signals by the catalytic reaction;
- each of the first and second carrier particles is not compartmentalized in the detection step;
- each of the first and second carrier particles is suspended in solution and not compartmentalized in the immobilization step; and
- the first analyte and the second analyte are distinctly detected in the detection step based on the mutually distinguishable signals.

20. A method of digital detection of an analyte in a sample, the method comprising the steps of:
- forming on each of carrier particles a complex containing a first capture substance capable of binding to an analyte, one molecule of the analyte, a second capture substance capable of binding to the analyte, and a catalyst;
- immobilizing a reaction product on each of the carrier particles by reacting the catalyst in the complex with a substrate; and
- detecting the analyte by digitally detecting the carrier particles on each of which the reaction product is immobilized, wherein
- one molecule of the analyte is captured per one carrier particle in the formation step;
- the reaction product is immobilized on the carrier particles on each of which the catalyst that has produced the reaction product is immobilized, but is not substantially immobilized on another carrier particle in the immobilization step;
- the formation step comprises a step of mixing the sample and a reagent containing a plurality of the carrier particles; and
- each carrier particle is suspended in solution and not compartmentalized in the detection step.

* * * * *